US011932696B2

(12) United States Patent
Yoshida et al.

(10) Patent No.: US 11,932,696 B2
(45) Date of Patent: *Mar. 19, 2024

(54) METHOD OF TREATING CANCER WITH AN ANTI-CCR8 THAT BINDS TUMOR INFILTRATING CELLS

(71) Applicants: Shionogi & Co., Ltd., Osaka (JP); Osaka University, Suita (JP)

(72) Inventors: Tetsuya Yoshida, Toyonaka (JP); Yujiro Kidani, Toyonaka (JP); Mitsunobu Matsumoto, Toyonaka (JP); Takayuki Kanazawa, Toyonaka (JP); Satomi Shinonome, Toyonaka (JP); Kanji Hojo, Toyonaka (JP); Naganari Ohkura, Suita (JP); Shimon Sakaguchi, Suita (JP); Atsushi Tanaka, Suita (JP); Hisashi Wada, Suita (JP); Atsunari Kawashima, Suita (JP); Norio Nonomura, Suita (JP)

(73) Assignees: SHIONOGI & CO., LTD., Osaka (JP); OSAKA UNIVERSITY, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/134,775

(22) Filed: Dec. 28, 2020

(65) Prior Publication Data

US 2021/0115148 A1 Apr. 22, 2021

Related U.S. Application Data

(63) Continuation of application No. 16/732,764, filed on Jan. 2, 2020, which is a continuation of application No. 16/183,216, filed on Nov. 7, 2018, now Pat. No. 10,550,191, which is a continuation of application No. PCT/JP2018/012644, filed on Mar. 28, 2018.

(30) Foreign Application Priority Data

Mar. 29, 2017 (JP) ................................. 2017-065603
Sep. 27, 2017 (JP) ................................. 2017-185935

(51) Int. Cl.
| | | |
|---|---|---|
| C07K 16/28 | (2006.01) | |
| A61K 9/00 | (2006.01) | |
| A61K 35/17 | (2015.01) | |
| A61K 39/00 | (2006.01) | |
| A61K 47/60 | (2017.01) | |
| A61K 47/64 | (2017.01) | |
| A61K 47/68 | (2017.01) | |
| A61P 35/00 | (2006.01) | |
| G01N 33/50 | (2006.01) | |

(52) U.S. Cl.
CPC ........ *C07K 16/2866* (2013.01); *A61K 9/0019* (2013.01); *A61K 35/17* (2013.01); *A61K 47/60* (2017.08); *A61K 47/6435* (2017.08); *A61K 47/6883* (2017.08); *A61P 35/00* (2018.01); *C07K 16/2818* (2013.01); *C07K 16/2827* (2013.01); *G01N 33/5011* (2013.01); *A61K 2039/505* (2013.01); *A61K 2039/507* (2013.01); *A61K 2039/572* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 10,087,259 B1 | 10/2018 | Rudensky et al. |
|---|---|---|
| 10,550,191 B2 | 2/2020 | Yoshida et al. |
| 2009/0214533 A1* | 8/2009 | Clynes .................... A61P 35/00 424/133.1 |
| 2010/0239633 A1 | 9/2010 | Strome et al. |
| 2014/0072528 A1 | 3/2014 | Gerdes et al. |
| 2018/0000931 A1 | 1/2018 | Bacac et al. |

FOREIGN PATENT DOCUMENTS

| CA | 3057274 A1 | 10/2018 | |
|---|---|---|---|
| JP | WO2018/181425 A1 | 10/2018 | |
| WO | 02/062850 A2 | 8/2002 | |
| WO | 2007/044756 A2 | 4/2007 | |
| WO | 2013/131010 A2 | 9/2013 | |
| WO | 2015/063187 A1 | 5/2015 | |
| WO | 2015/179236 A1 | 11/2015 | |
| WO | 2016/069727 A1 | 5/2016 | |
| WO | 2016/092419 A1 | 6/2016 | |
| WO | 2017/198631 A1 | 11/2017 | |
| WO | 2017/205014 A1 | 11/2017 | |
| WO | WO2017198631 * | 11/2017 | ............. C07K 14/47 |
| WO | 2018/112032 A1 | 6/2018 | |
| WO | 2018/112033 A1 | 6/2018 | |
| WO | 2018/181424 A1 | 10/2018 | |
| WO | 2019/157098 A1 | 8/2019 | |
| WO | 2021/178749 A2 | 9/2021 | |

(Continued)

OTHER PUBLICATIONS

BioLegend Corporation. Data sheet for anti-CCR8 antibody. Dec. 16, 2015. (Year: 2015).*
Plitas et al. (Abstract P4-04-11: Preferential expression of the chemokine receptor 8 (CCR8) on regulatory T cells (Treg) infiltrating human breast cancers represents a novel immunotherapeutic target. Thirty-Eighth Annual CTRC-AACR San Antonio Breast Cancer Symposium; Dec. 2010, San Antonio, TX. (Year: 2010).*
Biolegend product sheet for an anti CCR8 antibody (revision date Dec. 16, 2015). (Year: 2015).*
Hoelzinger et al. Blockade of CCL1 inhibits T regulatory cell suppressive function enhancing tumor immunity without affecting T effector responses. J. Immunol. 184: 6833-6842, 2010. (Year: 2010).*

(Continued)

*Primary Examiner* — Elly-Gerald Stoica
(74) *Attorney, Agent, or Firm* — Morgan, Lewis & Bockius LLP

(57) ABSTRACT

The present invention provides a pharmaceutical composition for cancer treatment comprising an antibody against CCR8.

7 Claims, 21 Drawing Sheets

(56) References Cited

FOREIGN PATENT DOCUMENTS

WO  2022/136649 A1  6/2022

OTHER PUBLICATIONS

Shinkawa et al. The absence of fucose but not the presence of galactose or bisecting N-acetylglucosamine of human IGg1 complex-type oligosaccharides shows the critical role of enhancing antibody-dependent cellular cytotoxicity. J. Biol. Chem. 278, 3466-3473, 2003. (Year: 2003).*
Iida et al., "Nonfucosylated therapeutic IgG1 antibody can evade the inhibitory effect of serum Immunoglobulin G on antibody-dependent cellular cytotoxicity through its high binding to FcγRIIIa," Clinical Cancer Research, 12 (9): 2879-2887 (2006).
Irani et al., "Molecular Properties of Human IgG Subclasses and their Implications for Designing Therapeutic Monoclonal Antibodies against Infectious Diseases," Molecular Immunology, 67: 171-182 (2015).
Josephs et al., "IgE Immunotherapy: A Novel Concept with Promise for the Treatment of Cancer," mAbs, 6 (1): 54-72 (2013).
Robertson et al., "NKT Cell Networks in the Regulation of Tumor Immunity," Frontiers in Immunology, 5 (article 543): 1-12 (2014).
Tan et al., "Crystal Clear: Visualizing the Intervention Mechanism of the PD-1/PD-L1 Interaction by Two Cancer Therapeutic Monoclonal Antibodies," Protein Cell, 7 (12): 866-877 (2016).
Zingoni et al., "Cutting Edge: The Chemokine Receptor CCR8 Is Preferentially Expressed in Th2 But Not Th1 Cells," Journal of Immunology, 161: 547-551 (1998).
Brüggemann et al., "Immunoglobulin heavy chain locus of the rat: Striking homology to mouse antibody genes," PNAS, 83: 6075-6079 (1986).
Kim et al., "Regulatory T cells prevent catastrophic autoimmunity throughout the lifespan of mice," Nature Immunology, 8 (2): 191-197 (2007).
Liang et al., "Depletion of regulatory T cells by targeting folate receptor 4 enhances the potency of a GM-CSF-secreting tumor cell immunotherapy," Clinical Immunology, 148: 287-298 (2013).
Lo et al., "Effector Attenuating Substitutions that Maintain Antibody Stability and Reduce Toxicity in Mice," The American Society for Biochemistry and Molecular Biology, Inc., JBC Papers in Press, M116.767749 (2017).
Onizuka et al., "Tumor Rejection by in Vivo Administration of Anti-CD25 (Interleukin-2 Receptor α) Monoclonal Antibody," Cancer Research, 59: 3128-3133 (1999).
Teng et al., "Multiple Antitumor Mechanisms Downstream of Prophylactic Regulatory T-Cell Depletion," Microenvironment and Immunology, American Association for Cancer Research, 70(7): 2665-2674 (2010).
BioLegend: APC antimouse CD198(CCR8) Antibody, Anti-CCR8 antibody data sheet (2018).
Angelova et al., "Characterization of the immunophenotypes and antigenomes of colorectal cancers reveals distinct tumor escape mechanisms and novel targets for immunotherapy," Genome Biology, 16 (64): 3-17 (2015).
Barsheshet et al., "CCR8+FOXp3+ Treg cells as master drivers of immune regulation," PNAS, 114 (23): 6086-6091 (2017).
Bates et al., "Quantification of Regulatory T Cells Enables the Identification of High-Risk Breast Cancer Patients and Those at Risk of Late Relapse," Journal of Clinical Oncology, 24 (34): 5373-5380 (2006).
Curiel et al., "Specific recruitment of regulatory T cells in ovarian carcinoma fosters immune privilege and predicts reduced survival," Nature Medicine, 10 (9): 942-949 (2004).
de Simone et al., "Transcriptional Landscape of Human Tissue Lymphocytes Unveils Uniqueness of Tumor-Infiltrating T Regulatory Cells," Immunity, 45 (5): 1135-1147 (2016).

Eruslanov et al., "Expansion of CCR8+ inflammatory myeloid cells in cancer patients with urothelial and renal carcinomas," Clinical Cancer Research, 19 (7): 1670-1680 (2013).
Finotello et al., "New strategies for cancer immunotherapy: targeting regulatory T cells," Genome Medicine, 9 (10): 1-3 (2017).
Fu et al., "Positive intratumoral chemokine (C-C motif) receptor 8 expression predicts high recurrence risk of post-operation clear-cell renal cell carcinoma patients," Oncotarget, 7 (7): 8413-8421 (2015).
Gao et al., "Intratumoral Balance of Regulatory and Cytotoxic T Cells Is Associated With Prognosis of Hepatocellular Carcinoma After Resection," Journal of Clinical Oncology, 25 (18): 2586-2593 (2007).
Gutierrez et al., "Analysis of Post-translational CCR8 Modifications and Their Influence on Receptor Activity," The Journal of Biological Chemistry, 279 (15):14726-14733 (2004).
Halim et al., "An Atlas of Human Regulatory T Helper-like Cells Reveals Features of Th2-like Tregs that Support a Tumorigenic Environment," Cell Reports, 20 (3): 757-770 (2017).
Hoelzinger et al., "Blockade of CCL1 Inhibits T Regulatory Cell Suppressive Function Enhancing Tumor Immunity without Affecting T Effector Responses", The Journal of Immunology, 184 (12): 6833-6842 (2010).
Iellem et al., "Unique Chemotactic Response Profile and Specific Expression of Chemokine Receptors CCR4 and CCR8 by CD4+ CD25+ Regulatory T Cells," Journal of Experimental Medicine, 194 (6): 847-853 (2001).
International Search Report issued in PCT/JP2018/012644 dated Jun. 26, 2018.
Li et al., "Efficient Treg depletion induces T-cell infiltration and rejection of large tumors," European Journal of Immunology, 40: 3325-3335 (2010).
McCully et al., "CCR8 Expression Defines Tissue-Resident Memory T Cells in Human Skin," The Journal of Immunology, 200: 1639-1650 (2018).
Napolitano et al., "Molecular Cloning of TER1, a Chemokine Receptor-Like Gene Expressed by Lymphoid Tissues," The Journal of Immunology, 157: 2759-2763 (1996).
Oshio et al., "Chemokine Receptor CCR8 Is Required for Lipopolysaccharide-Triggered Cytokine Production in Mouse Peritoneal Macrophages", PLoS One, 9 (4): 1-12 (2014).
Perrone et al., "Intratumoural FOXP3-positive regulatory T cells are associated with adverse prognosis in radically resected gastric cancer," European Journal of Cancer, 44: 1875-1882 (2008).
Petersen et al., "Tumor Infiltrating FOXP3+ Regulatory T-cells Are Associated With Recurrence in Pathologic Stage I NSCLC Patients," Cancer, 107 (12): 2866-2872 (2006).
Plitas et al., "Regulatory T Cells Exhibit Distinct Features in Human Breast Cancer," Immunity, 45 (5): 1122-1134 (2016).
Plitas et al, "Abstract P4-04-11: Preferential expression of the chemokine receptor 8 (CCR8) on regulatory T cells (Treg) infiltrating human breast cancers represents a novel immunotherapeutic target," Cancer Research, 76 (4): 5 pages (2016).
Roos et al., "Identification of CCR8, the Receptor for the Human CC Chemokine I-309," The Journal of Biological Chemistry, 272 (28): 17251-17254 (1997).
Shah et al., "A reversed CD4/CD8 ratio of tumor-infiltrating lymphocytes and a high percentage of CD4+FOXP3 regulatory T cells are significantly associated with clinical outcome in squamous cell carcinoma of the cervix," Cellular & Molecular Immunology, 8: 59-66 (2011).
Sugiyama et al., "Anti-CCR4 mAb selectively depletes effector-type FoxP3+CD4+ regulatory T cells, evoking antitumor immune responses in humans," PNAS, 110 (44): 17945-17950 (2013).
Villarreal et al., "Targeting CCR8 Induces Protective Antitumor Immunity and Enhances Vaccine-Induced Responses in Colon Cancer," Cancer Research, 78 (18): 5340-5348 (2018).
Villarreal et al., "Targeting of CCR8 induces antitumor activity as a monotherapy that is further enhanced in combination with a Listeria-based immunotherapy", ASCO, 1 page (2018).
Wang et al., "Optimal Population of FoxP3+ T Cells in Tumors Requires an Antigen Priming-Dependent Trafficking Receptor Switch," PLoS One, 7 (1): 1-12 (2012).

(56) References Cited

OTHER PUBLICATIONS

Written Opinion (PCT/ISA/237) issued in PCT/JP2018/012644, dated Jun. 26, 2018.
Zou, "Regulatory T cells, tumour immunity and immunotherapy," Nature Reviews: Immunology, 6: 295-307 (2006).
Karin, "Chemokines and cancer: new immune checkpoints for cancer therapy," Current Opinion in Immunology, 51: 140-145 (2018).
Van Glnderachter, et al., https://cris.vub.be/en/projects/blockade-of-the-ccr8-chemokine-receptor-as-novel-cancer-therapy(0869ab0e-ebdf-4039-9236-5082675cdc15).html, Jul. 10, 2020.
Edwards et al., "The Remarkable Flexibility of the Human Antibody Repertoire; Isolation of Over One Thousand Different Antibodies to a Single Protein," Journal of Molecular Biology, 334: 103-118 (2003).
Teilaude et al., Monoclonal Antibodies Reveal the Structural Basis of Antibody Diversity, Science, (222): 721-726 (1983).
Lloyd et al., "Modelling the human immune response: performance of a 10 11 human antibody repertoire against a broad panel of therapeutically relevant antigens," Protein Engineering, Design & Selection, 22 (3): 159-168 (2009).
Kawashima et al., "Identification of CCR8 as a specific marker of tumor tissue-infiltrating regulatory T cells and its possibility as a therapeutic target in renal cell carcinoma," Eur Urol Supplement, 18 (11): e3557 (2019).
Coghill et al., "CC chemokine receptor 8 potentiates donor Treg survival and is critical for the prevention of murine graft-versus-host disease," Blood 122(5): 825-836 (2013).
Van Ginderachter et al., "Blockade of the CCR8 chemokine receptor as novel cancer therapy," VUB Project Information (2017-2020).
Supporting evidence for date of VUB project, Carbon Dating The Web (2017) (https://cris.vub.be/en/prodects/blockade-of-the-ccr8-chemokine-receptor-as-novel-cancer-therpy).
Arkin et al., "Combined Nivolumab and Ipilimumab or Monotherapy in Untreated Melanoma," The New England Journal of Medicine, 373: 23-34 (2015).
Onishi et al., "Immunotherapy Approaches Targeting Regulatory T-Cells," Anticancer Research, 32: 997-1004 (2012).
Simpson et al., "Fc-dependent depletion of tumor-infiltrating regulatory T cells co-defines the efficacy of anti-CTLA-4 therapy against melanoma," JEM, 210(9): 1695-1710 (2013).
Product description for PE anti-mouse CD279 (PD-1) Antibody (2016).
Takeuchi et al., "Roles of regulatory T cells in cancer immunity," International Immunology, 28(8): 401-409 (2016).
Kurose et al., "Phase la Study of FoxP3+ CD4 Treg Depletion by Infusion of a Humanized Anti-CCR4 Antibody, KW-0761, in Cancer Patients," Clinical Cancer Research, 21(19) 4327-4336 (2015).
Opposition against European Patent No. 3431105 dated Oct. 1, 2020.
Bos et al., "Transient regulatory T cell ablation deters oncogene-driven breast cancer and enhances radiotherapy," JEM, 210(11): 2435-2446 (2013).
Kim et al., "Cutting Edge: Depletion of Foxp3+ Cells Leads to Induction of Autoimmunity by Specific Ablation of Regulatory T Cells in Genetically Targeted Mice," The Journal of Immunology, 183: 7631-7634 (2009).
Dietze et al., "Transient depletion of regulatory T cells in transgenic mice reactivates virus-specific CD8+ T cells and reduces chronic retroviral set points," PNAS, 108(6) 2420-2425 (2011).
Zelinskyy et al., "The regulatory T-cell response during acute retroviral infection is locally define and controls the magnitude and duration of the virus-specific cytotoxic T-cell response," Blood, 114(15) 3199-3207 (2009).
Dannull et al., "Enhancement of vaccine-mediated antitumor immunity in cancer patients after depletion of regulatory T cells," The Journal of Clinical Investigation, 115(12): 3623-3633 (2005).
Spain et al., "Management of toxicities of immune checkpoint inhibitors," Cancer Treatment Reviews, 44: 51-60 (2016).
Communication 94(3) EP17725914.0 (WO2017/198631) dated Jan. 15, 2020.
Day et al., "Preclinical Mouse Cancer Models: A Maze of Opportunities and Challenges," Cell 163: 39-53 (2015).
Debes et al., "CCL8 and skin T cells-an allergic attraction," Nature Immunology, 12(2): 111-112 (2011).
Howard et al., "LEC induces chemotaxis and adhesion by interacting with CCR1 and CCR8," Blood, 96(3): 840-845 (2000).
Islam et al., "Identification of human CCR8 as a CCL 18 receptor," JEM 210(10): 1889-1898 (2013).
Depis et al., Abstract 4532: Preclinical evaluation of JTX-1811, an anti-CCR8 antibody with enhanced ADCC activity, for preferential depletion of tumor-infiltrating regulatory T cells, Cancer Research (2020).
Klages et al., "Selective Depletion of Foxp3+ Regulatory T Cells Improves Effective Therapeutic Vaccination against Established Melanoma," Cancer Research 70(20) 7788-7799 (2010).
Shipman, "Interrogating intratumoral Treg cells," Nature Reviews Immunology, 12/5 (2016).
Stallard, "New Approach Could Boost Immunotherapy for Breast Cancer," Memorial Sloan Kettering Cancer Center (2016).
Klarenbeek et al., "Targeting chemokines and chemokine receptors with antibodies," Drug Discovery Today, 9(4): e237-e244 (2012).
Vela et al., "Chemokine receptor-specific antibodies in cancer immunotherapy: achievements and challenges," Frontiers in Immunology, 6(12): 1-15 (2015).
Rajasekaran et al., "Enhancement of antibody-dependent cell mediated cytotoxicity: a new era in cancer treatment," ImmunoTargets and Therapy, 5(4): 91-100 (2015).
Technical Manual: mFcgmmaRIV ADCC Reporter Bioassay, Core Kit (Promega) (2017).
Review InvivoGen: Immunoglobulin G (2011).
Bruhns, "Properties of mouse and human lgG receptors and their contribution to disease models," Blood, 119(24): 5640-5649 (2012).
Technical Data Sheet, BV421 Mouse Anti-Human CCR8 (CD198), 433H data sheet, BD Biosciences (2016).
Kim et al., "Immune escape to PD-L1/PD-1 blockade: seven steps to success (or failure)," Annals of Oncology 27(8) 1492-1504 (2016).
Experimental Data Report cited in Opposition against EP 3431105/ 18775737.2 dated Oct. 2020.
Das et al., "Tumor cell entry into the lymph node is controlled by CCL1 chemokine expressed by lymph node lymphatic sinuses," JEM, 210(8): 1509-1528 (2013).
Jung et al., "Combination therapy of chemokine receptor inhibition plus PDL-1 blockade potentiates anti-tumor effects In a murine model of breast cancer," Journal of Immuno Therapy of Cancer, 3 (supplement 2): P227 (2015).
Excerpt from ClinicalTrials.gov, "study of Mogamulizumab + MEDI4736 (Durvalumab) and Mogamulizumab + Tremelimumab in Subjects w/ Advanced Solid Tumors," downloaded from htts:// clinicaltrials.gov/ct2/study/NCT02301130 (2016).
Yamamoto et al., "Anti-CC-chemokine receptor 4 (CCR4) antibody mogamulizumab (Moga) and nivolumab (Nivo) combination phase I study in patients with advanced or metastatic solid tumors," ESMO 28 (supplement 5) (2017).
Mutalithas et al., "Expression of CCR8 is increased in asthma," Clinical & Experimental Allergy, 40(8): 1175-1185 (2010).
Kipps et al., "Importance of Immunoglobulin Isotype in Human Antibody-Dependent, Cell-Mediated Cytotoxicity Directed by Murine Monoclonal Antibodies," Journal of Experimental Medicine, 161: 1-17 (1985).
Dempke et al., "Second- and third-generation drugs for immuno-oncology treatment—The more the better?" European Journal of Cancer, 74, 55-72 (2017).
Vargas et al., "Fc-Optimized Anti-CD25 Depletes Tumor-Infiltrating Regulatory T Cells and Synergizes with PD-1 Blockade to Eradicate Established Tumors," Immunity 46: 577-586 (2017).
Grounds of Opposition filed in European Patent 3431105 dated Oct. 1, 2020.
Statement of Facts and Arguments in Support of Opposition filed in European Patent 3431105 dated Oct. 2020.

(56) References Cited

OTHER PUBLICATIONS

Notice of Opposition Facts and Arguments in accordance with Article 100 EPC in respect of Opposition against European Patent 3431105 dated Oct. 2020.
Notice of Opposition filed in European Patent No. 3431105 dated Oct. 1, 2020.
Ruckes et al., "Autocrine antiapoptotic stimulation of cultured adult T-cell leukemia cells by overexpression of the chemokine I-309," Blood, 98 (4): 1150-1159 (2001).
Louahed et al., "CCR8-dependent activation of the RAS/MAPK pathway mediates anti-apoptotic activity of I-309/CCL1 and vMIP-I," European Journal of Immunology, 33: 494-501 (2003).
Robertson et al., "NKT cell networks in the regulation of tumor immunity," Frontiers in Immunology, 5: 543 (2014).
Fisher et al., "Transient Treg depletion enhances therapeutic anti-cancer vaccination," Immunity, Inflammation and Disease, 5 (1): 16-28 (2017).
Dhodapkar et al., "Type II Nkt Cells and Their Emerging Role in Health and Disease," The Journal of Immunology, 198: 1015-1021 (2017).
Whiteside et al., "CCR8 marks highly suppressive Treg cells within tumours but is dispensable for their accumulation and suppressive function," Immunology, 163: 512-520 (2021).
Campbell et al., "Fc-Optimized Anti-CCR8 Antibody Depletes Regulatory T Cells in Human Tumor Models," Cancer Research, 81: 2983-2994 (2021).
Van Damme et al., "Therapeutic depletion of CCR8+ tumor-infiltrating regulatory T cells elicits antitumor immunity and synergizes with anti-PD-1 therapy," Journal for ImmunoTherapy of Cancer, 9: e001749 (2021).
NCT02476123 "Study of Combination Therapy With Mogamulizumab (KW-0761) and Nivolumab (ONO-4538/ BMS-936558) in Subjects With Advanced Solid Tumors" (2015).
NCT02705105 "Study of Mogamulizumab + Nivolumab in Subjects w/Locally Advanced or Metastatic Solid Tumors" (2016).
NCT02301130 "Study of Mogamulizumab + MEDI4736 and Mogamulizumab + Tremelimumab in Subjects wl Advanced Solid Tumors" (2016).
Griffith et al., "Inhibition of Murine Prostate Tumor Growth and Activation of Immunoregulatory Cells with Recombinant Canarypox Viruses," Journal of the National Cancer Institute, 93 (13): 998-1007 (2001).
NCT01929486 "Phase la/lb Multicenter Trial of Mogamulizumab for Advanced or Recurrent Cancer" (2016).
Expert statement of Prof. Dr. Jo Van Ginderachter (Oct. 13, 2021).
Expert statement of Dr. Helge Roider (Oct. 14, 2021).
Ishii et al., "Defucosylated Humanized Anti-CCR4 Monoclonal Antibody KW-0761 as a Novel Immunotherapeutic Agent for Adult T-cell Leukemia/Lymphoma," Clinical Cancer Research, 16 (5): 1520-1531 (2010).
Shuptrine et al., "Monoclonal antibodies for the treatment of cancer," Seminars in Cancer Biology, 22: 3-13 (2013).
R&D 191704 data sheet (2007).
Zahavi et al., "Enhancing antibody-dependent cell-mediated cytotoxicity: a strategy for improving antibody-based Immunotherapy," Antibody Therapeutics, 1 (1): 7-12 (2018).
Nelson et al., "Antibody fragments: Hope and hype," mAbs, 2 (1): 77-83 (2010).
Mordant et al., "Bioluminescent Orthotopic Mouse Models of Human Localized Non-Small Cell Lung Cancer: Feasibility and Identification of Circulating Tumour Cells, " PLOS One, 6 (1): e26073 (2011).
Pyszniak et al., "Percentages of NKT cells in the tissues of patients with non-small cell lung cancer who underwent surgical treatment," Kardiochirurgia I Torakochirugia Polska, 11 (1): 34-39 (2014).
Tahir et al., "Loss of IFN-y Production by Invariant NK T Cells in Advanced Cancer," Journal of Immunology, 167: 4046-4050 (2001).

Penaloza-Macmaster et al., "Interplay between regulatory T cells and PD-1 in modulating T cell exhaustion and viral control during chronic LCMV infection," Journal of Experimental Medicine, 211 (9): 1905-1918 (2014).
Tanaka et al., "Regulatory T cells in cancer immunotherapy," Cell Research, 27: 109-118 (2017).
PlumX Metrics-Reguratory T Cells Exhibit Distinvt Features in Human Breast Cancer (2016).
Chiu et al., "Engineering antibody therapeutics," Current Opinion in Structural Biology, 38: 163-173 (2016).
Seidel et al., "Natural killer cell mediated antibody-dependent cellular cytotoxicity in tumor immunotherapy with therapeutic antibodies," Frontiers in Immunology, 4: 76 (2013).
Redman et al., "Mechanisms of Action of Therapeutic Antibodies for Cancer," Molecular Immunology, 67 (2000): 28-45 (2015).
ARC0956 (Abnova) dada sheet (2020).
Email from Thermofisher (2020).
Thermofisher Scienfitic Web Chat (2020).
BioLegend anti-CCR8 list (2021).
EBioscience anti-CCR8 list (2021).
Experimental Report provided by DYC (2) (2021).
Experimental Report provided by DYC (1) (2021).
Scott et al., "Antibody therapy of cancer," Nature Reviews: Cancer, 12: 278-287 (2012).
Haij et al., "In vivo Cytotoxicity of Type I CD20 Antibodies Critically Depends on Fc Receptor ITAM Signaling," Cancer Research, 70 (8): 3209-3217 (2010).
Tida et al., "Two mechanisms of the enhanced antibody-dependent cellular cytotoxicity (ADCC) efficacy of non- fucosylated therapeutic antibodies in human blood," BMC Cancer, 9: 58 (2009).
Trastuzumab Summary of Product Characteristics (2021).
Rituximab Summary of Product Characteristics (2021).
Macmillan: Side effects of cancer treatment (2021).
263G8 (BioLegend) data sheet (2015).
mFcyR ADCC Reporter Bioassay Core Kit Manual (2017).
Stallard, "FDA Approves 'Game Changer' Immunotherapy Drug for Bladder Cancer," Memorial Sloan Kettering Cancer Center, (2016).
Tontonoz et al., "Immunotherapy Pioneered at MSK Received FDA Approval for Advanced Kidney Cancer," Memorial Sloan Kettering Cancer Center, (2015).
Tontonoz et al., "Combination Immunotherapy Shows New Promise for Lung Cancer," Memorial Sloan Kettering Cancer Center, (2016).
Rosenberg et al., "Eosinophils: changing perspectives in health and disease," Nature Reviews: Immunology, 13 (2013).
Ganguly et al., "The role of dendritic cells in autoimmunity," Nat Rev Immunol., 13 (8): 566-577 (2013).
Slauenwhite et al., "Regulation of NKT Cell localization in homeostatis and infection," Frontiers in Immunology, 6: 255 (2015).
Wilcox, "Mogamulizumab: 2 birds, 1 stone," Blood, 125 (12): 1847-1848 (2015).
Chen et al., "Anti-PD-1/PD-L1 therapy of human cancer: past, present, and future," Journal of Clinical Investigation, 125 (9): 3384-3391 (2015).
Laurence, "Location, movement and survival: the role of chemokines in haematopoiesis and malignancy," British Journal of Haematology, 132: 255-267 (2005).
Kim et al., "Immunopathogenesis and therapy of cutaneous T cell lumphoma," Journal of Clinical Investigation, 115 (4): 798-812 (2005).
Ali et al., "An apparent paradox: Chemokine receptor agonists can be used for anti-inflammatory therapy," Molecular Immunology, 44: 1477-1482 (2007).
Gupta et al., "Antibodies against G-protein coupled receptors: novel uses in screening and drug development," Comb Chem High Throughput Screen, 11 (6): 463-467 (2008).
Han et al., "Monoclonal Antibodies as Cancer Therapeutics," North American Journal of Medicine and Science, 3 (3): 146-147 (2010).
Suzuki et al., "Current status of immunotherapy," Japanese Journal of Clinical Oncology, 46 (3): 191-203 (2016).
Opposition response to patentee's response filed in corresponding European Patent No. 3431105 dated Nov. 22, 2021.

(56) References Cited

OTHER PUBLICATIONS

Opposition response to patentee's response filed in corresponding European Patent No. 3431105 dated Oct. 14, 2021.
Opposition response to patentee's response filed in corresponding European Patent No. 3431105 dated Oct. 8, 2021.
Opposition filed in corresponding European Patent No. 3616720 Nov. 16, 2021.
Opposition filed in corresponding European Patent No. 3616720 Nov. 15, 2021.
Opposition filed in corresponding European Patent No. 3616720 dated Nov. 2021.
Opposition filed in corresponding European Patent No. 3616720 dated Nov. 17, 2021.
Opposition filed in corresponding European Patent No. 3616720 Nov. 17, 2021.
Opposition filed in corresponding European Patent No. 3616720 dated Nov. 16, 2021.
AbbVie Communication filed in Opposition to EP3431105 dated Nov. 30, 2022.
AbbVie-D Center for Drug Evaluation and Research cited in AbbVie Communication of Nov. 30, 2022.
AbbVie email to EPO dated Sep. 23, 2022.
Gevers Written Submission to the Summons to Attend Oral Proceedings in Opposition to EP3431105 dated Nov. 30, 2022.
Sagittarius Response to Summons to Attend Oral Proceedings in Opposition to EP3431105 dated Nov. 30, 2022.
J A Kemp Final Written Submission in Opposition to EP3431105 dated Nov. 2022.
Konig Szynka Tilmann von Renesse Patentanwalte Partnerschaft mbB written submission in Opposition to EP3431105 dated Nov. 30, 2022.
KSTR Advaxis Inc Presentations and Publications cited Konig Szynka Tilmann von Renesse Patentanwalte Partnerschaft mbB written submission in Opposition to EP3431105 dated Nov. 30, 2022.
Topalian et al., "Targeting the PD-1/B7-H1 (PD-L1) pathway to activate anti-tumor immunity," Curr Opin Immunol., 24 (2): 207-212 (2012).
Schiweck Weinzierl Koch Patentanwalte Partnerschaft mbB preparation to oral proceedings in response to the communication and update of opposition dated Nov. 30, 2022.
Teng et al., "Classifying Cancers Based on T-cell Infiltration and PD-L1," Cancer Research, 75 (11): 2139-2145 (2015).
Su et al., "Blocking the recruitment of naive CD4+ T cells reverses immunosuppression in breast cancer," Cell Research, 27: 461-482 (2017).
Harner et al., "Cord Blood Valpha24Vbeta11+ Natural Killer T cells Display a Th2-Chemokine Receptor Profile and Cytokine Responses," PLOS One, 6 (1): e15714 (2011).
Liu et al., "Neuron-mediated generation of regulatory T cells from encephalitogenic T cells suppresses EAE," nature Medicine, 12 (5): 518-525 (2006).
Berzofsky et al., "The Contrasting Roles of NKT cells in Tumor Immunity," Curr Mol Med., 9 (6): 667-672 (2009).
Experimental Report ADCC Deficient Anti-CCR8 Antibody vs Isotype Control cited in Shionogi response to Opposition submission dated Nov. 30, 2022.
Shionogi response to Opposition submission dated Nov. 30, 2022.
Third Party Observations filed in European Patent Application No. 18775737.2 dated Nov. 9, 2022.
Supplemental Information from Vargas et al. FC Optimized Anti-CD25 Depletes Tumor Infiltrating, Immunity, 46: 577 (2017).
Grosso et al., "CTLA-4 blockade in tumor models: an overview of preclinical and translational research," Cancer Immunity, 13 (5) (2013).
Datasheet for R&D Systems Anti-CCR8 antibody clone 1055C (2018).
Datasheet for Invitrogen anti-CCR8 antibody clone ARC0956.
Thermo Fisher Scientific Web Chat regarding antibody clone ARC0956.
Email from Thermo Fisher Scientific regarding antibody clone ARC0956 dated Aug. 21, 2020.
Certified Copy of Priority Document U.S. Appl. No. 62/626,885, filed Feb. 6, 2018.
Business Wire news article "Data Highlighting Advaxis" Antigen Delivery Platform Accepted for Multiple Presentations at 2018 Keystone Symposia Conference on Cancer Immunotherapies (Jan. 29, 2018).
Information Disclosure Statement filed in U.S. Appl. No. 16/183,216, filed Nov. 7, 2018.
Meeting Book for Cancer Immunotherapy: Combinations, organised by Keystone Symposia and held at Fairmont The Queen Elizabeth in Montreal QC Canada from Mar. 23-27, 2018.
Addendum to the Meeting Book for Cancer Immunotherapy: Combinations, organised by Keystone Symposia and held at Fairmont The Queen Elizabeth in Montreal QC Canada from Mar. 23-27, 2018.
BioLegend Purified anti-mouse CD198 (CCR8) antibody, SA214G2, Catalog# 150302, Version: 1, Dec. 16, 2015, pp. 1-2 (Year: 2015).

\* cited by examiner

[Figure 1]
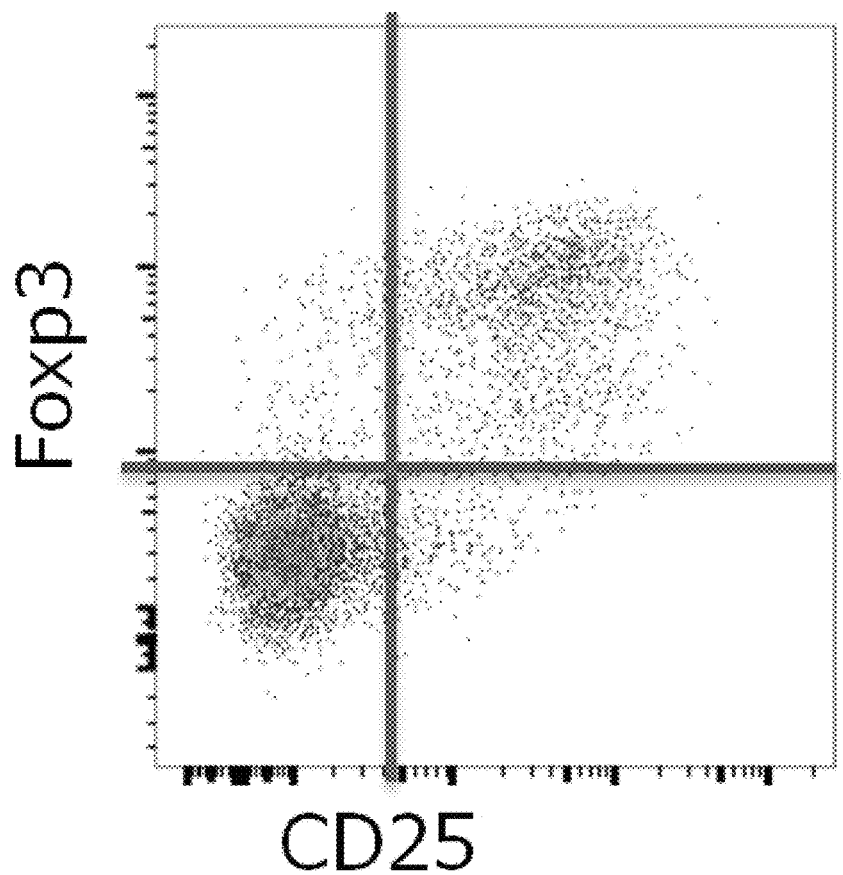
[Figure 2]
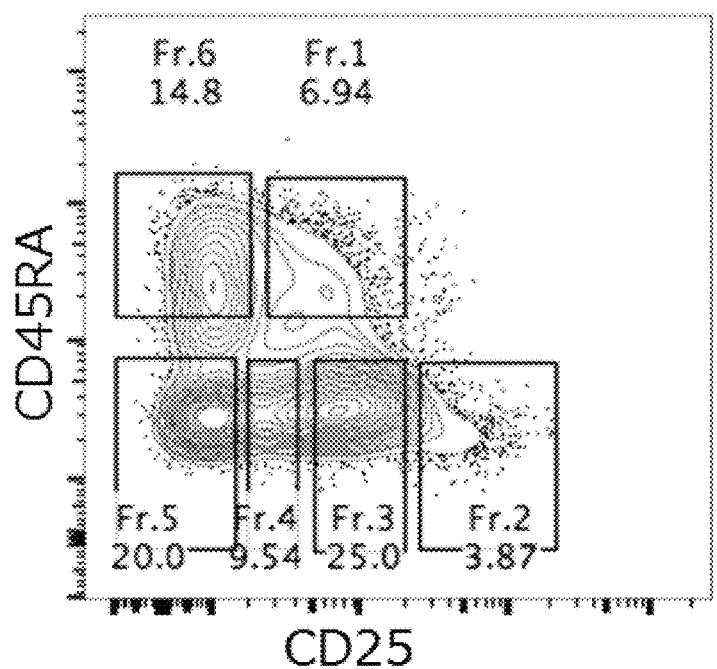

[Figure 3]
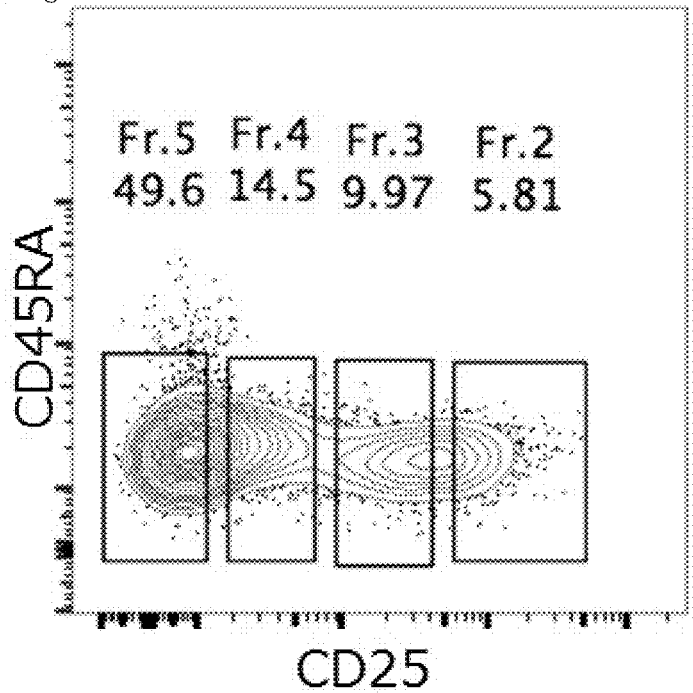
[Figure 4]
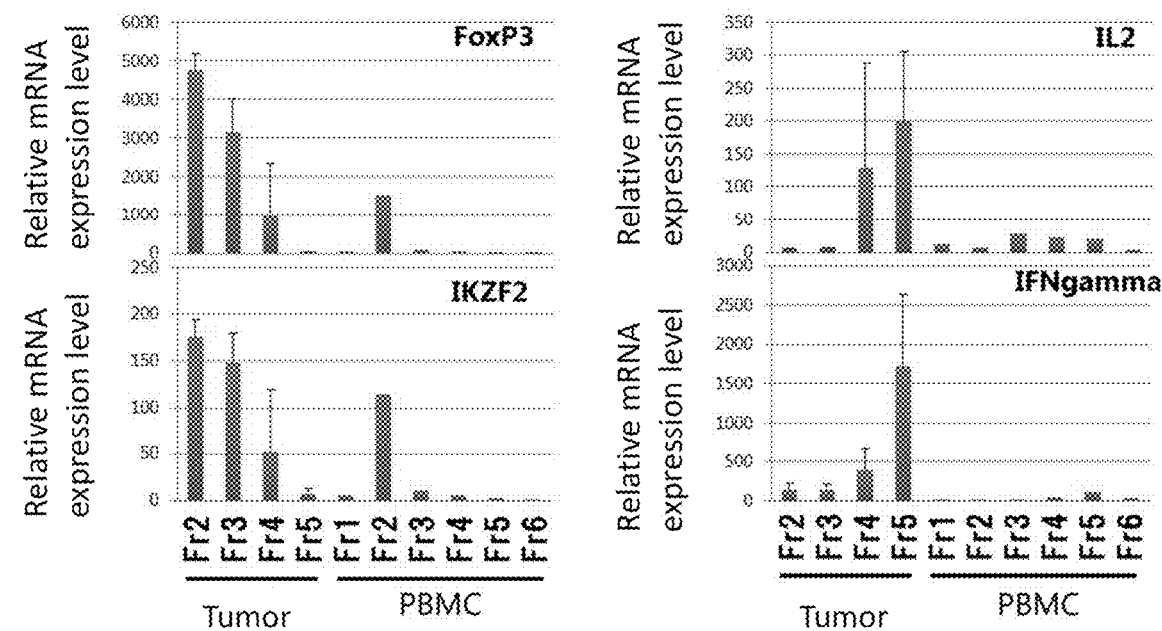

[Figure 5]
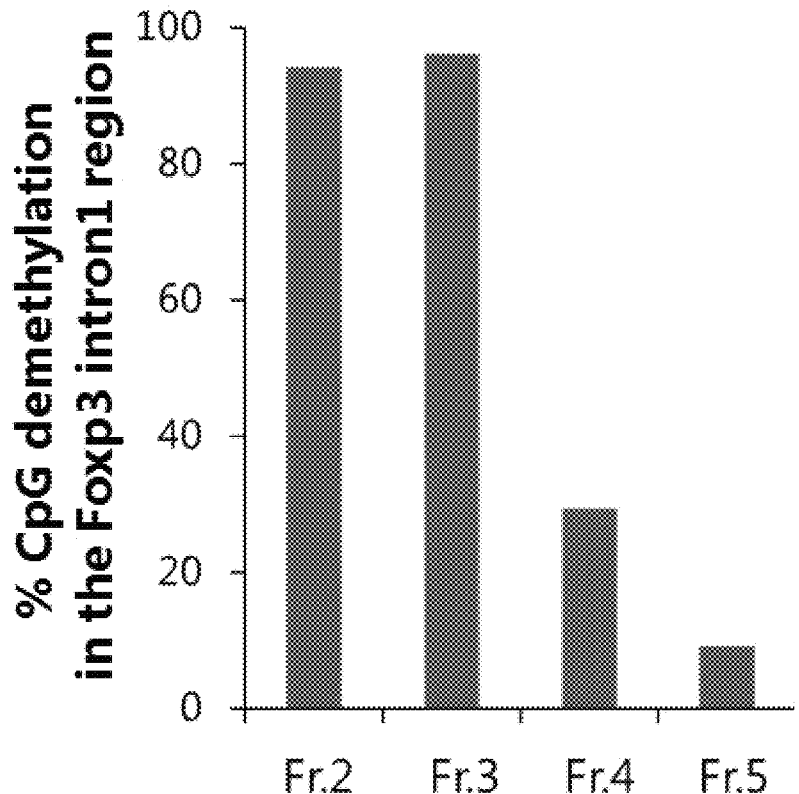
[Figure 6]
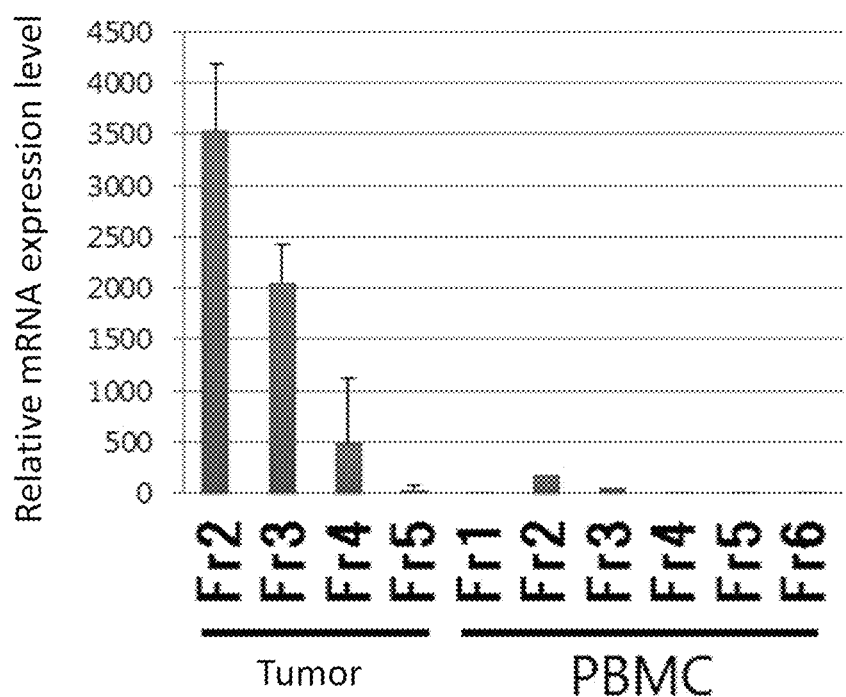

[Figure 7]
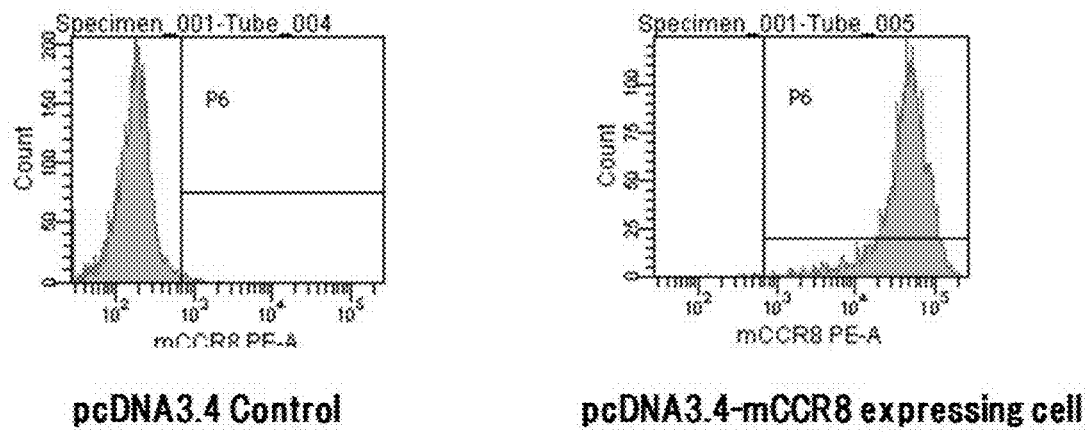
[Figure 8]
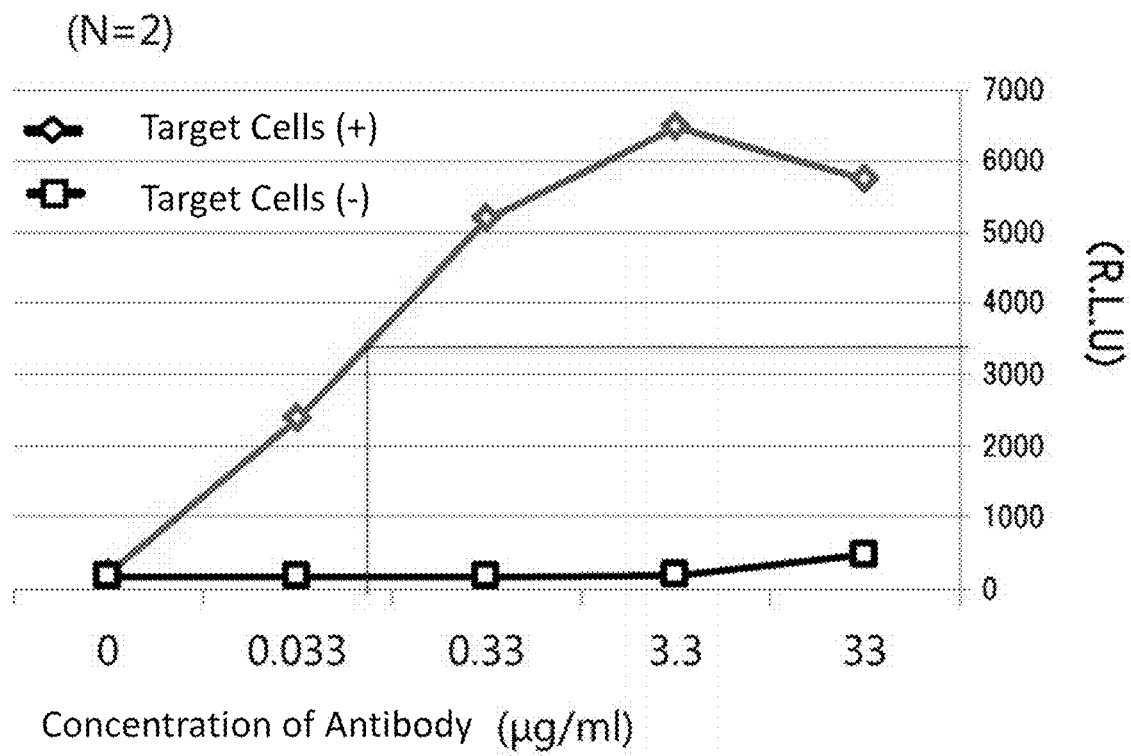

[Figure 9]
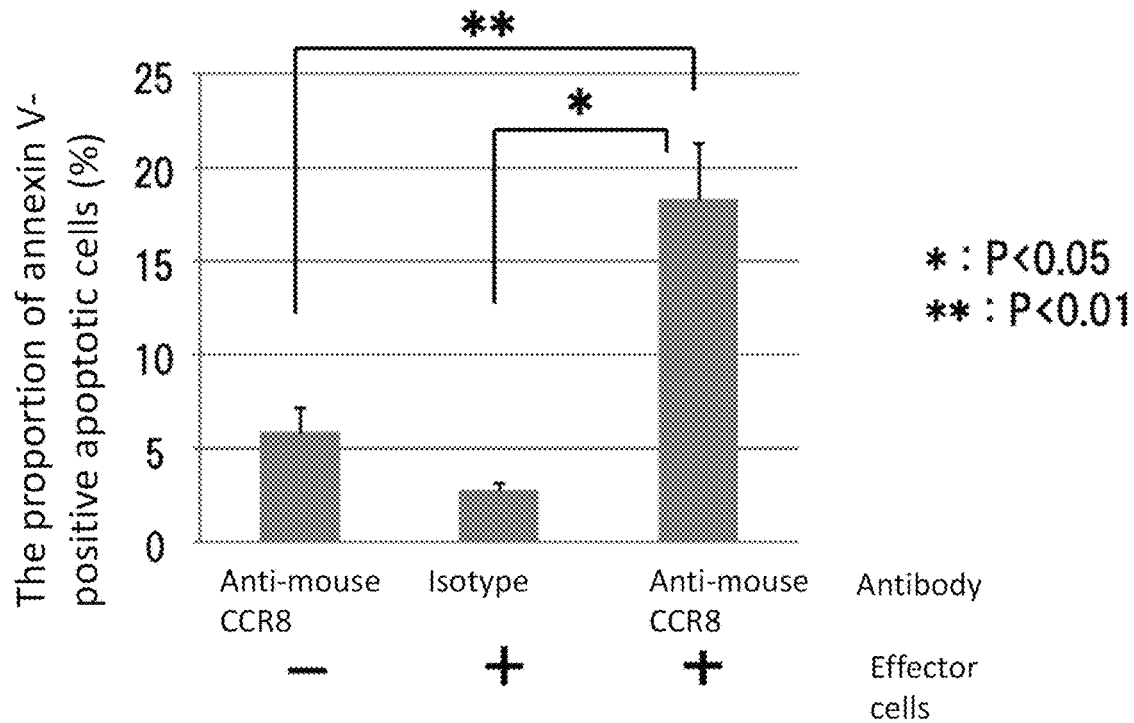
[Figure 10]
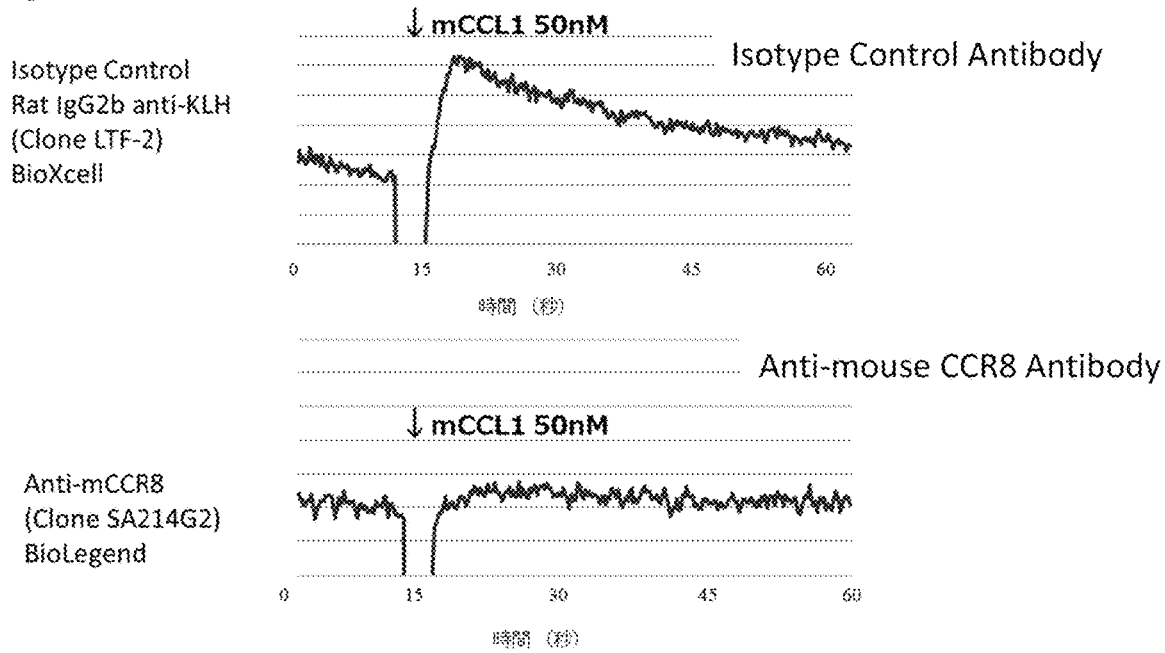

[Figure 11]
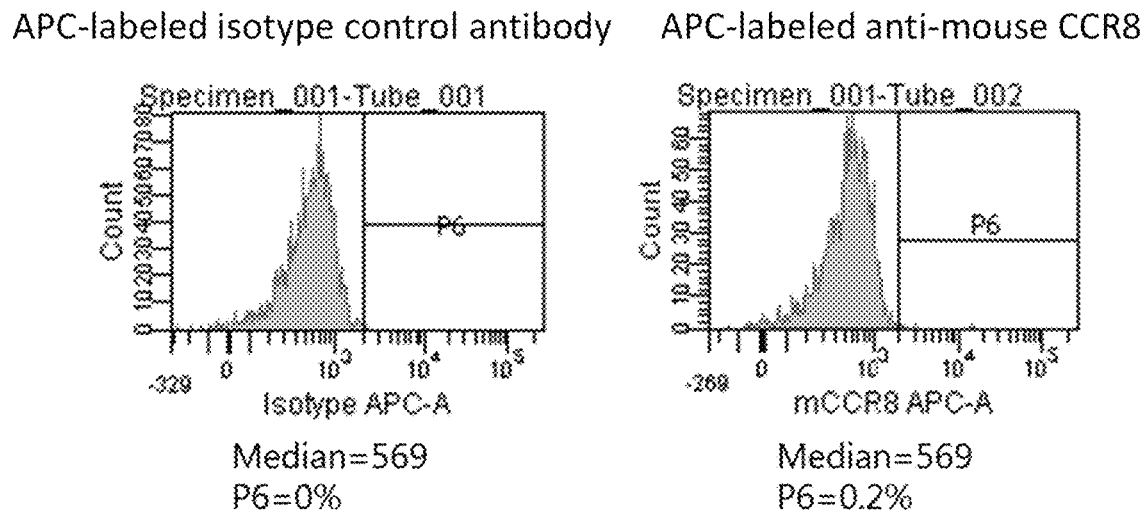
[Figure 12]
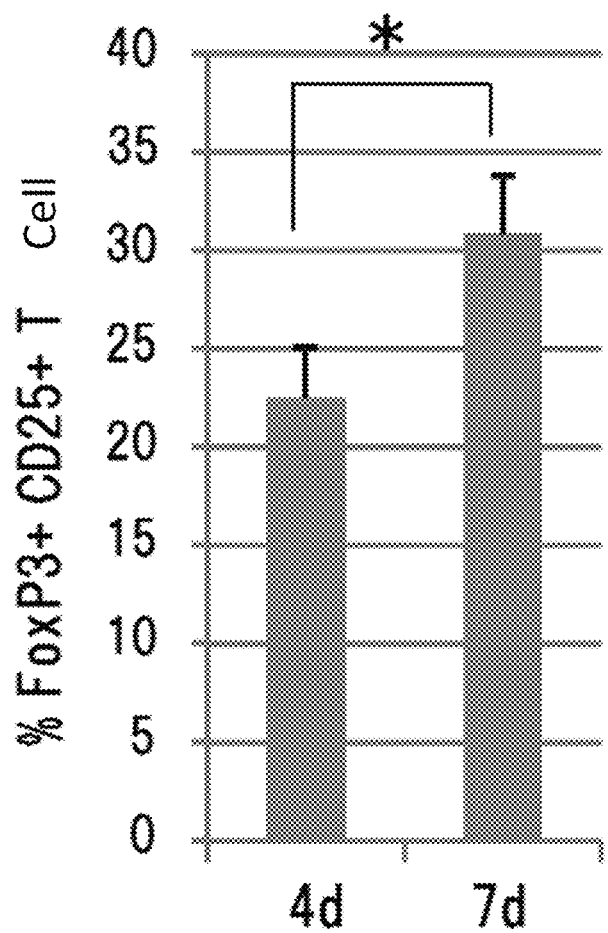

[Figure 13]
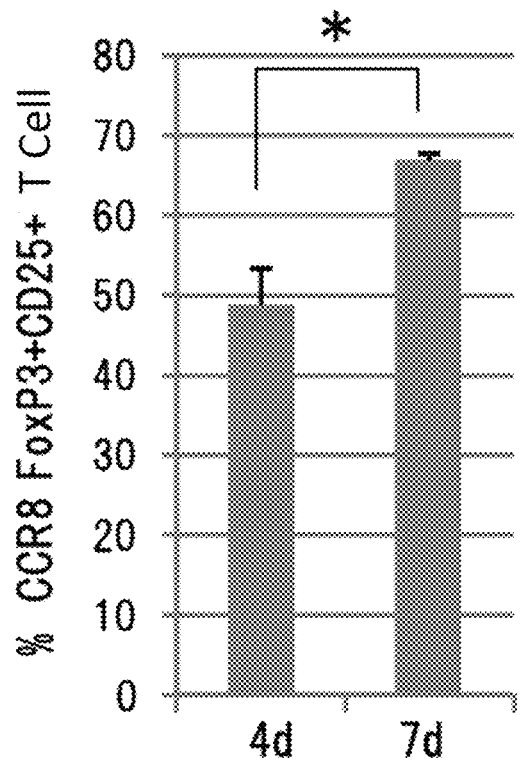
[Figure 14]
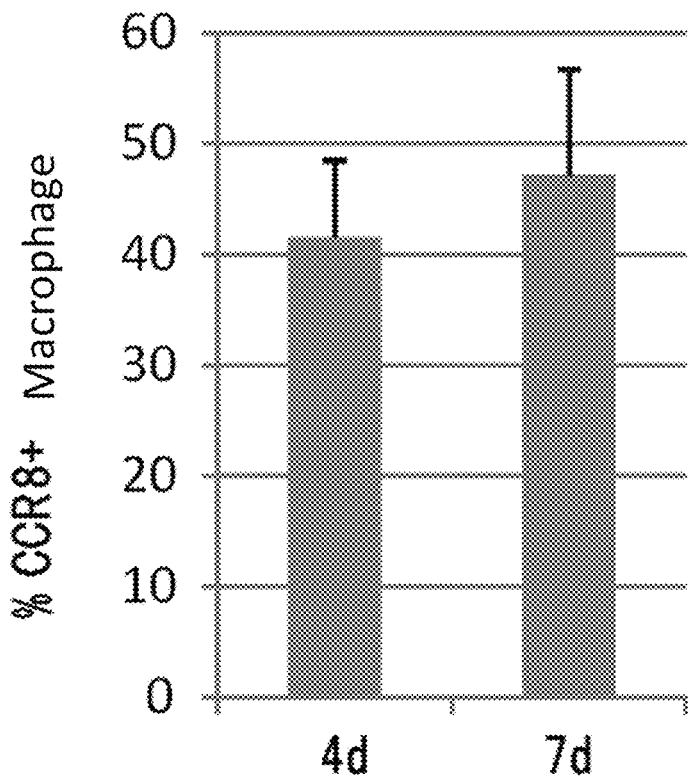

[Figure 15]
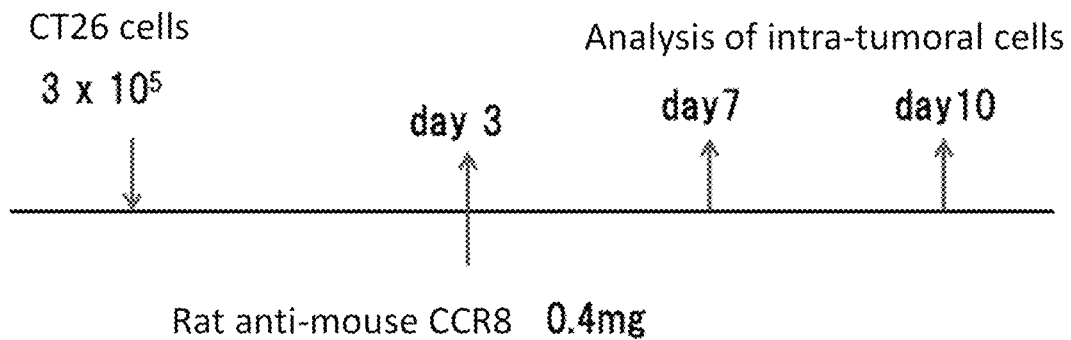
[Figure 16]
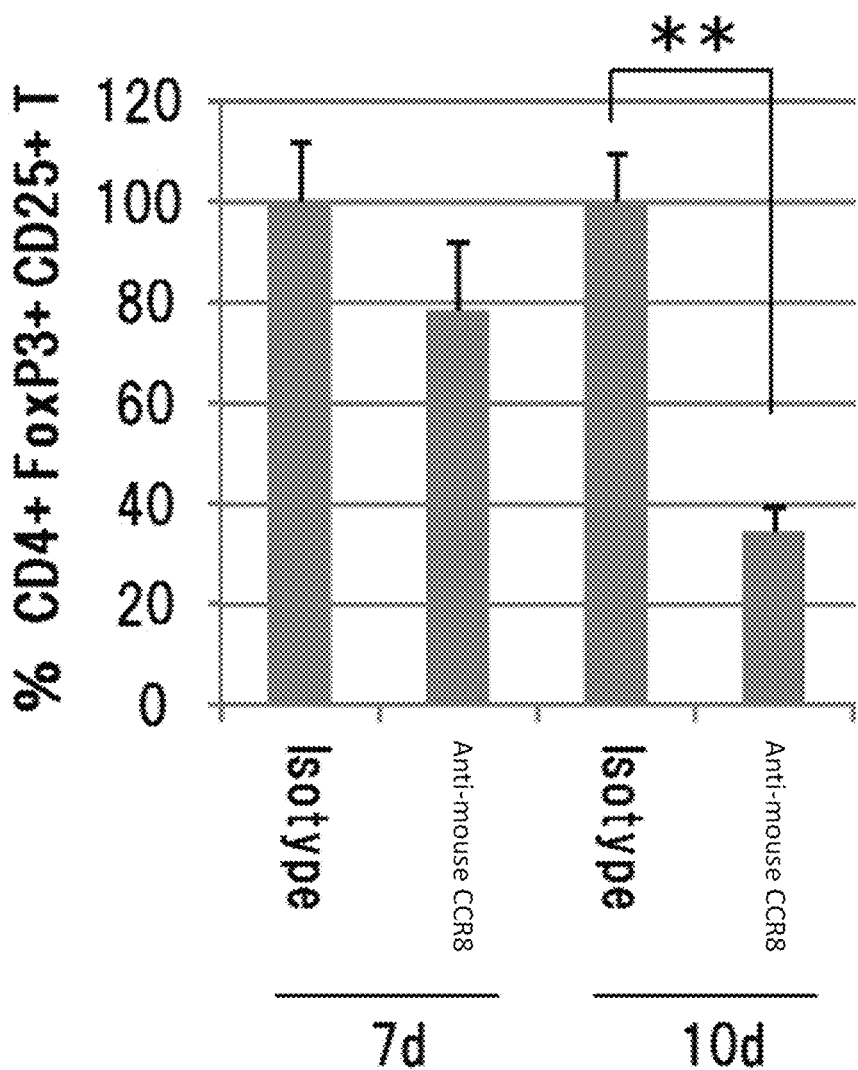

[Figure 17]
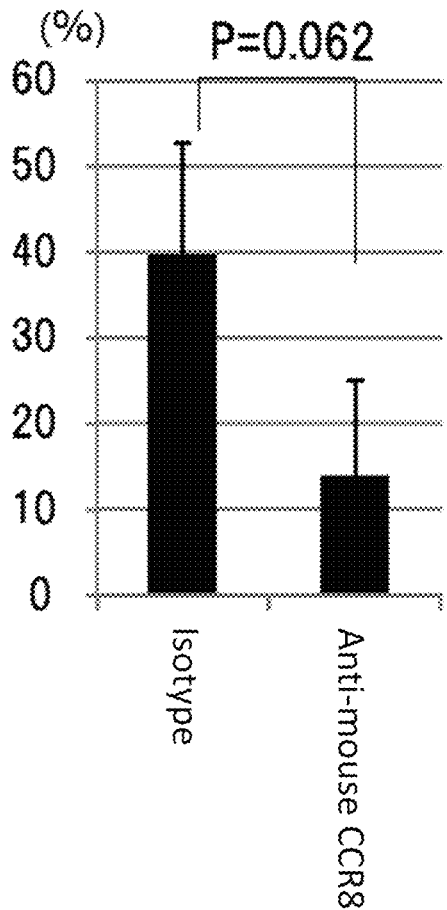
[Figure 18]
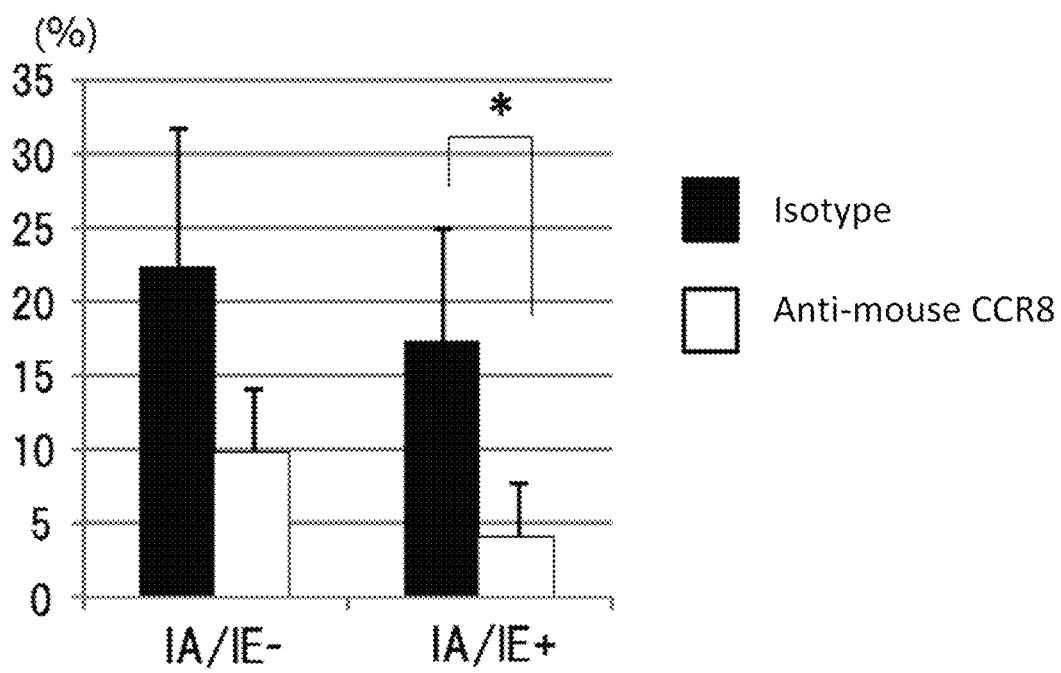

[Figure 19]
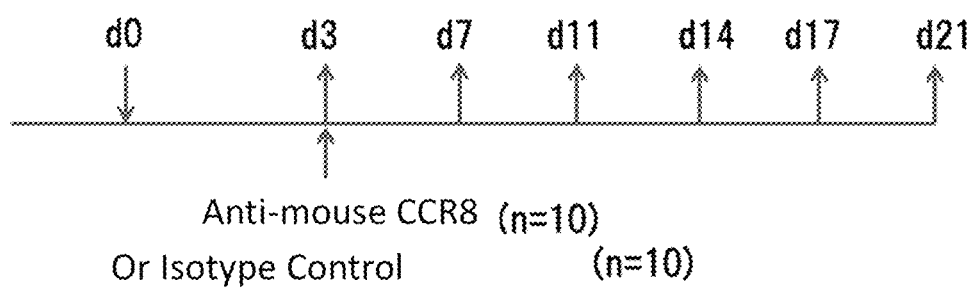
[Figure 20]
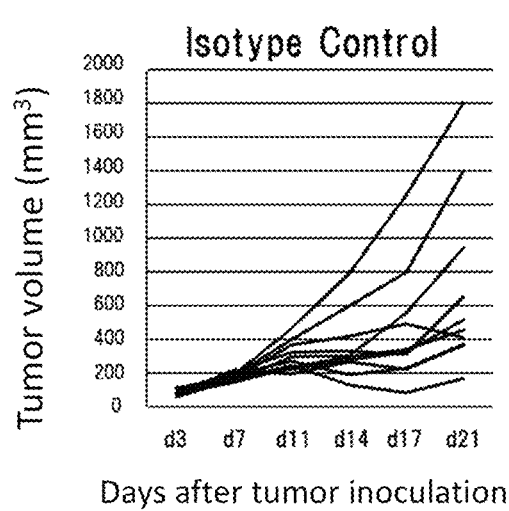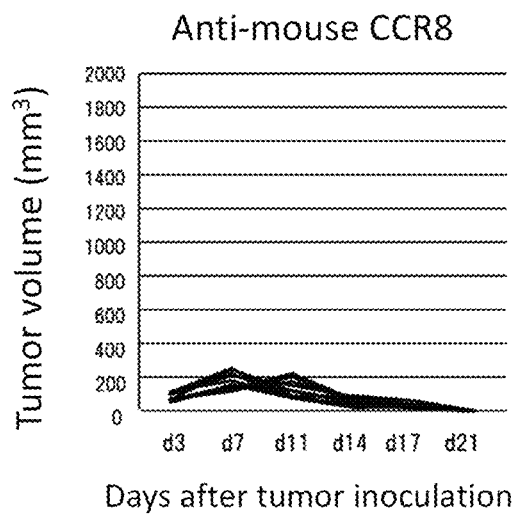

[Figure 21]
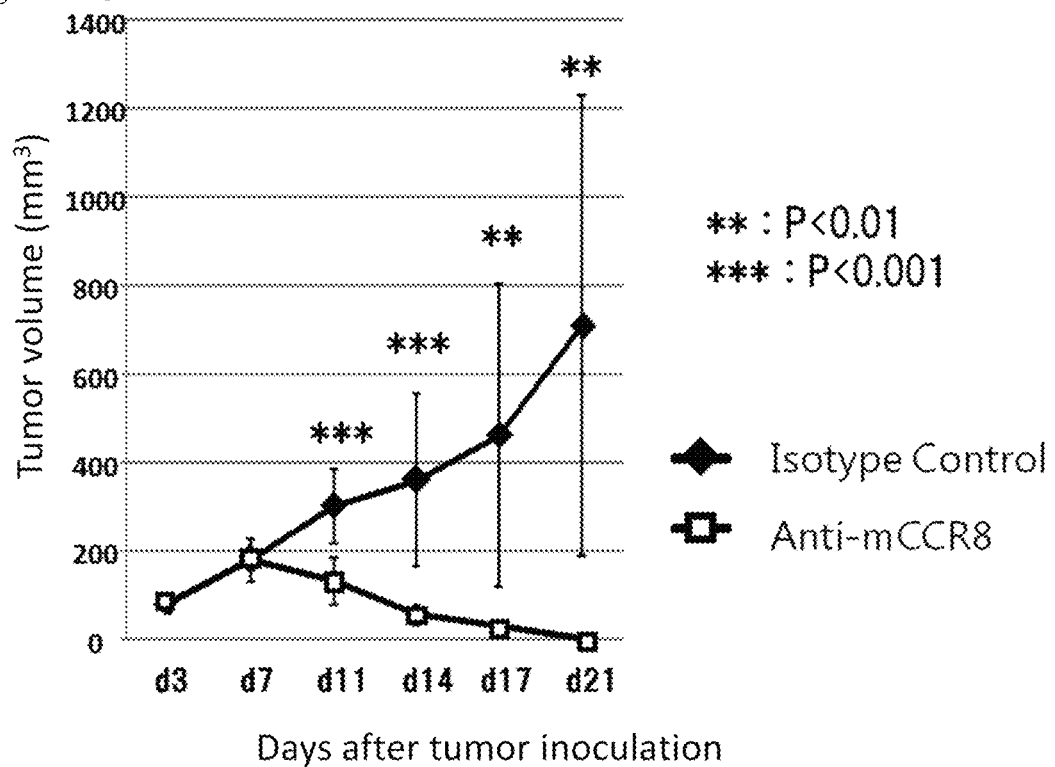
[Figure 22]
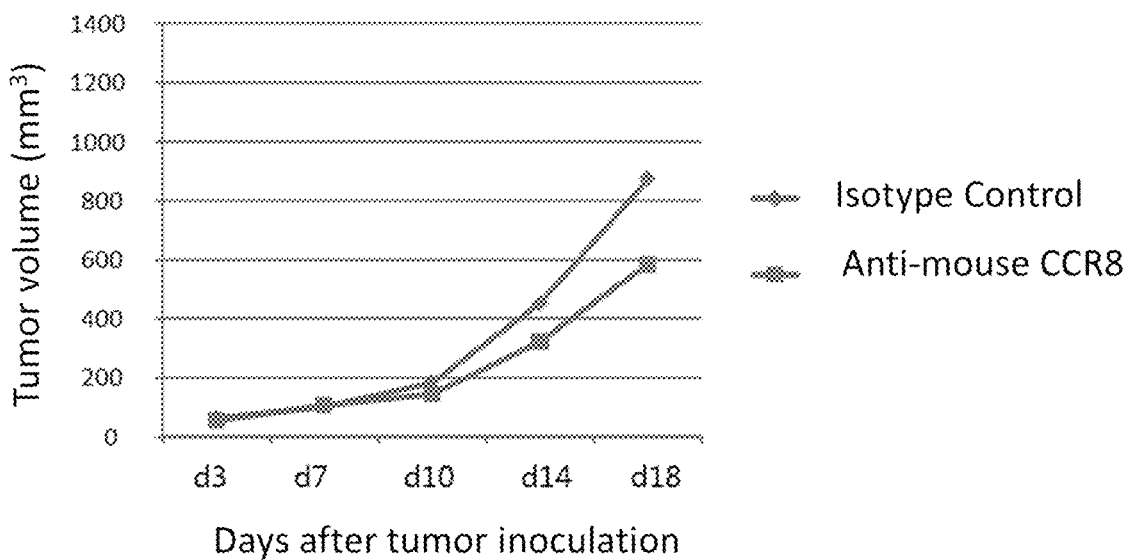

[Figure 23]
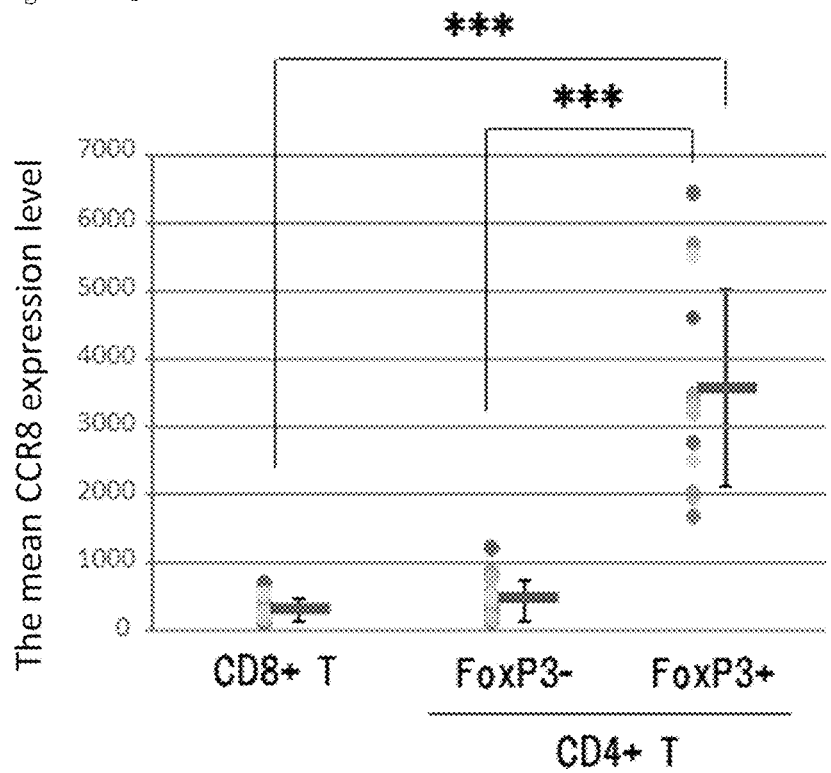
[Figure 24]
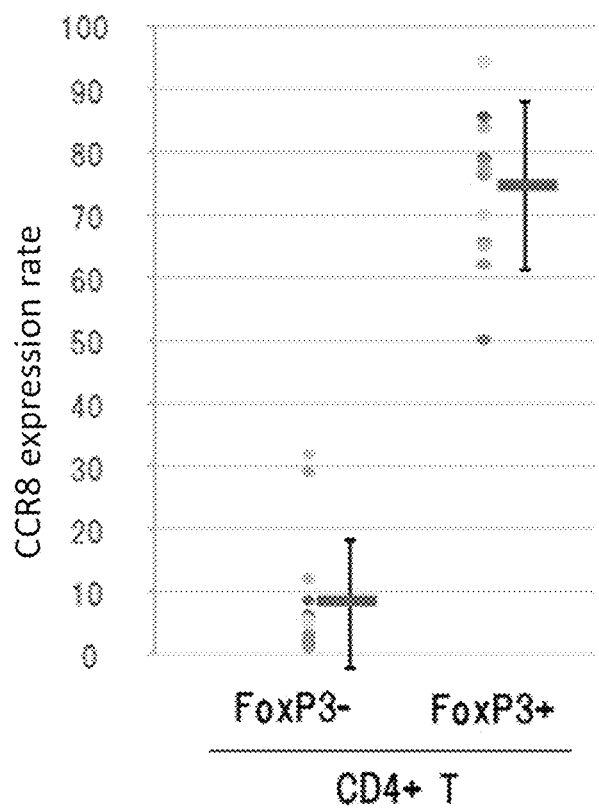

[Figure 25]
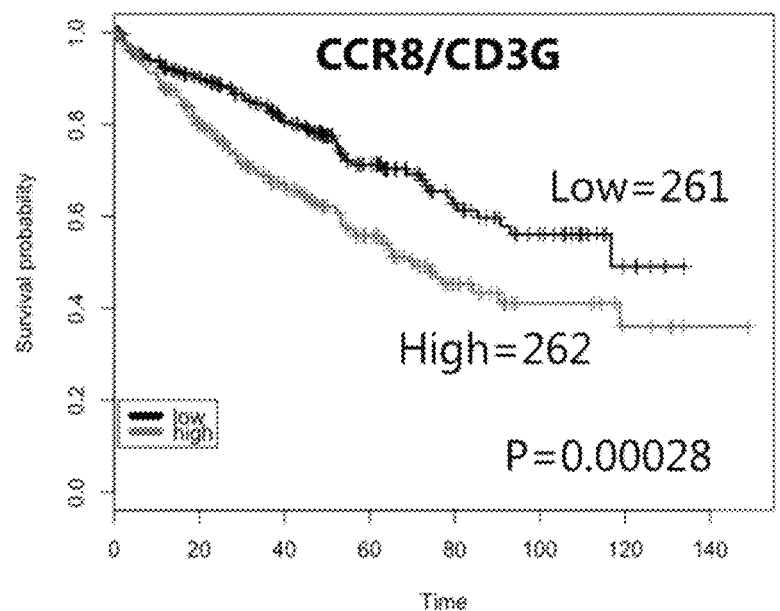
[Figure 26]
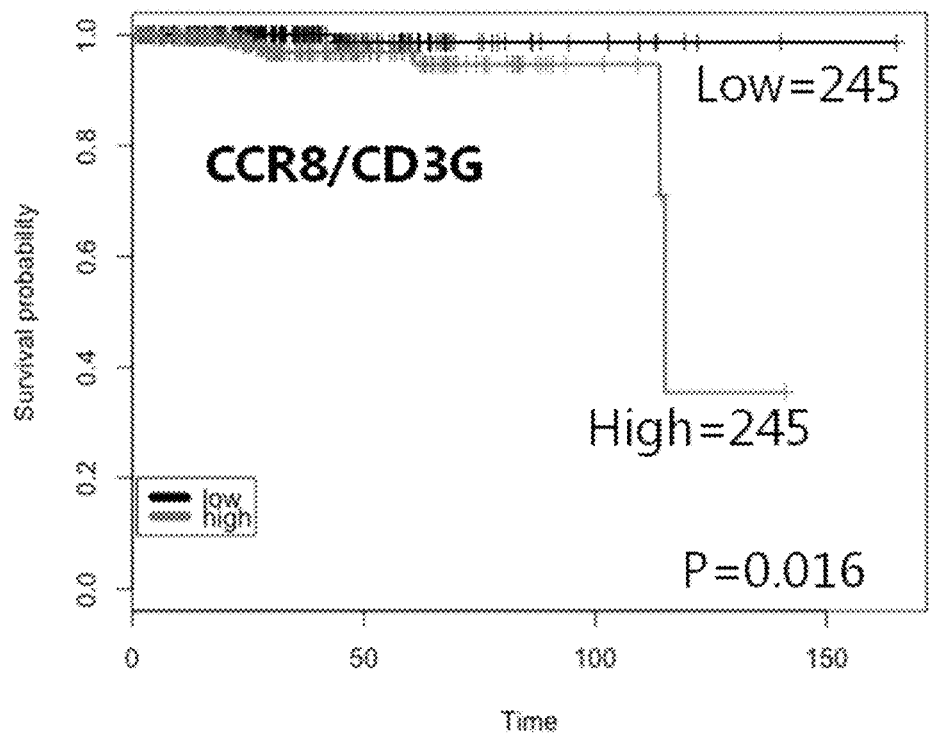

[Figure 27]
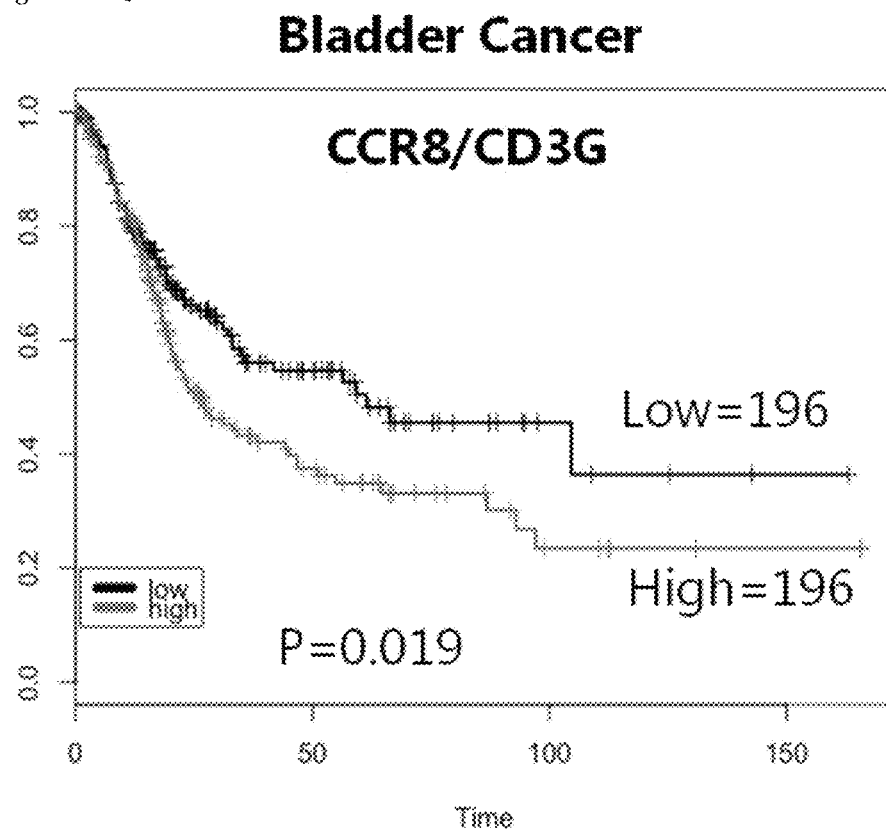
[Figure 28]
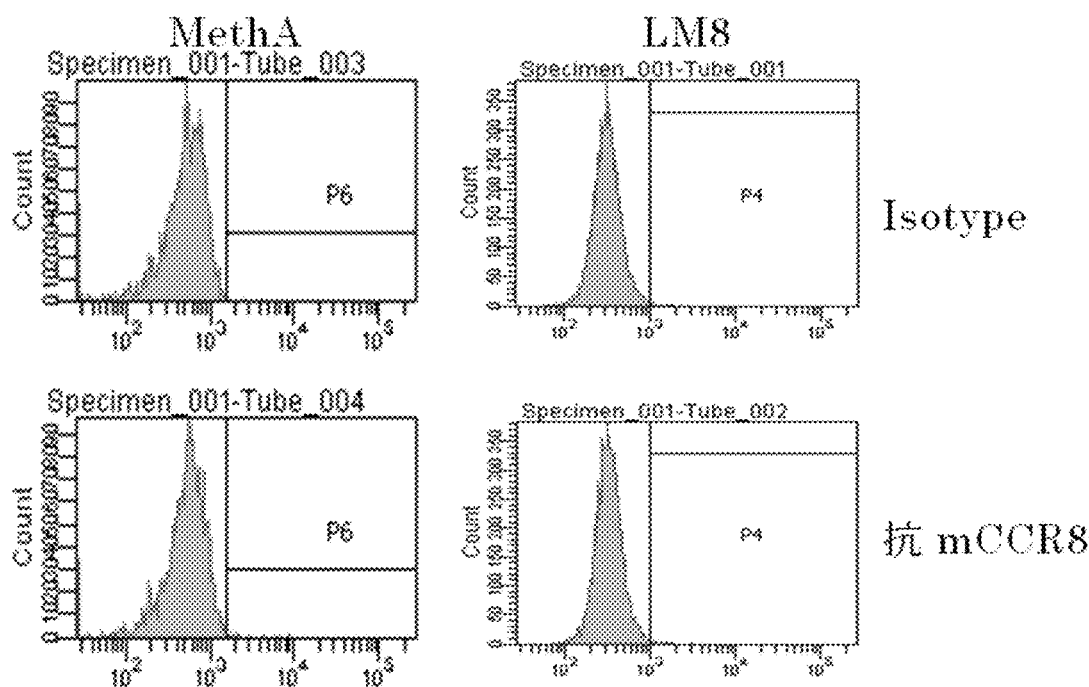

[Figure 29]
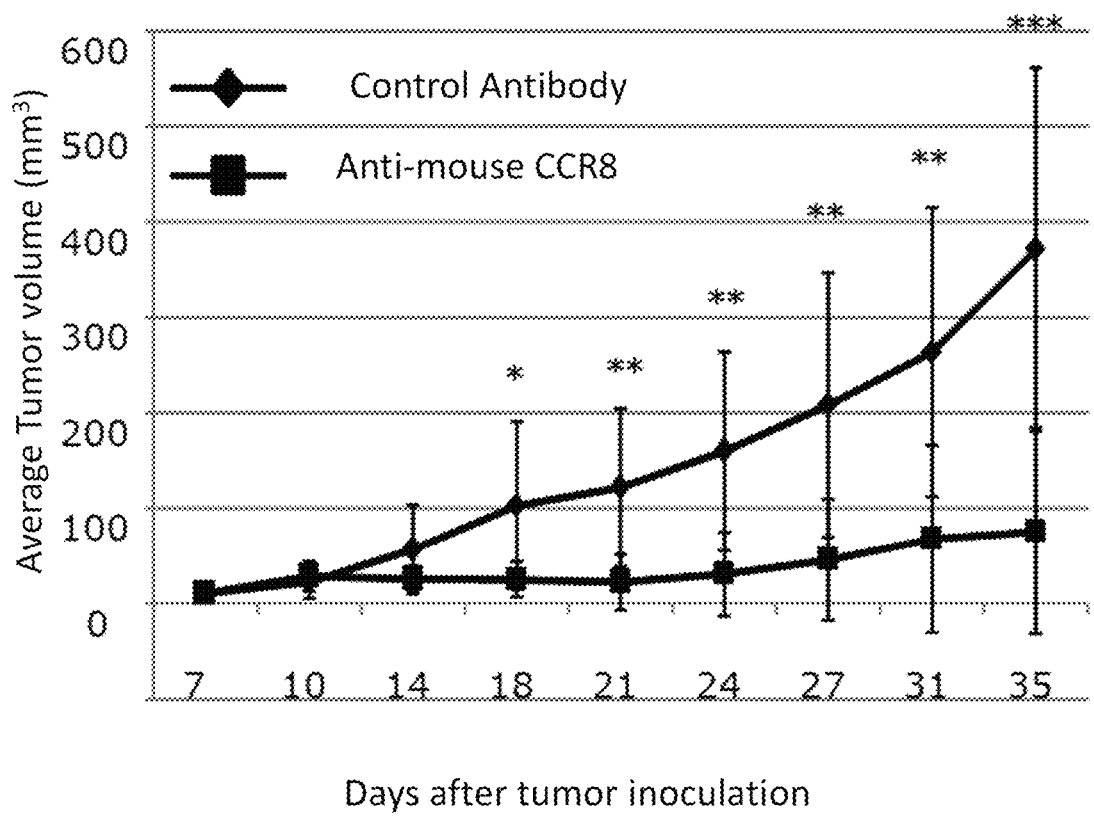
Days after tumor inoculation

[Figure 30]
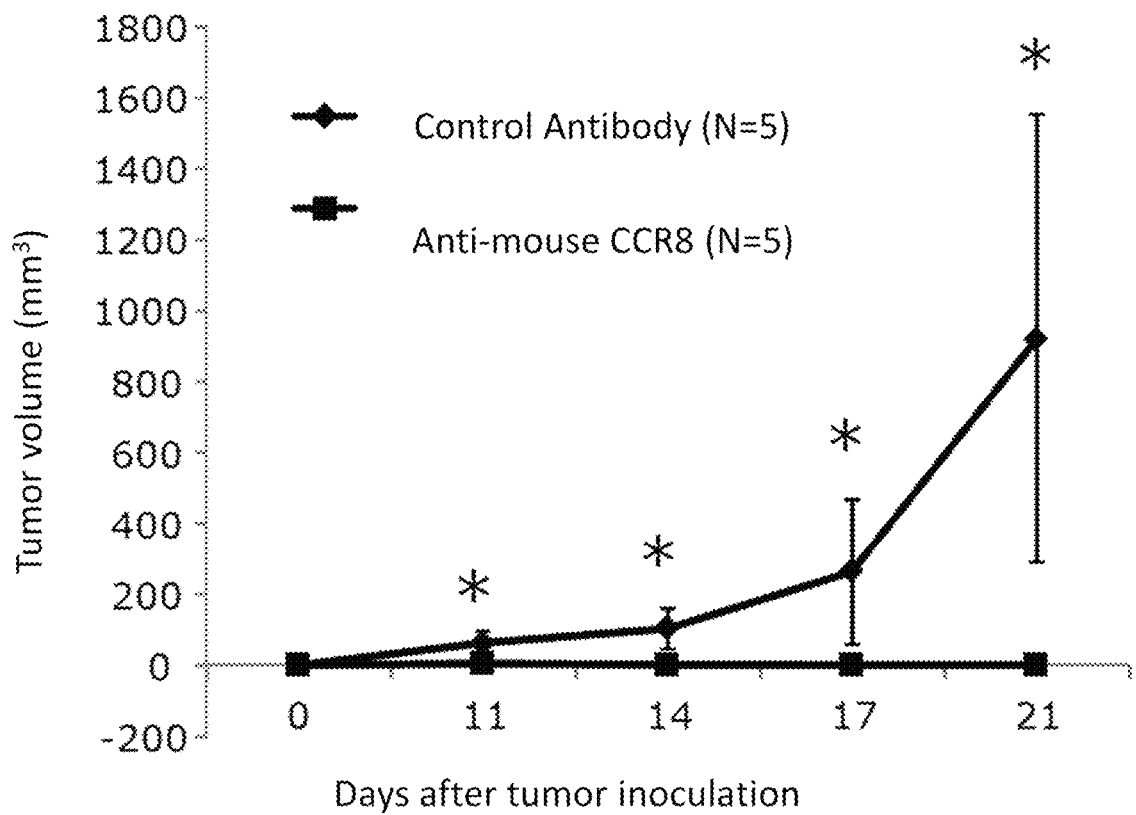
[Figure 31]
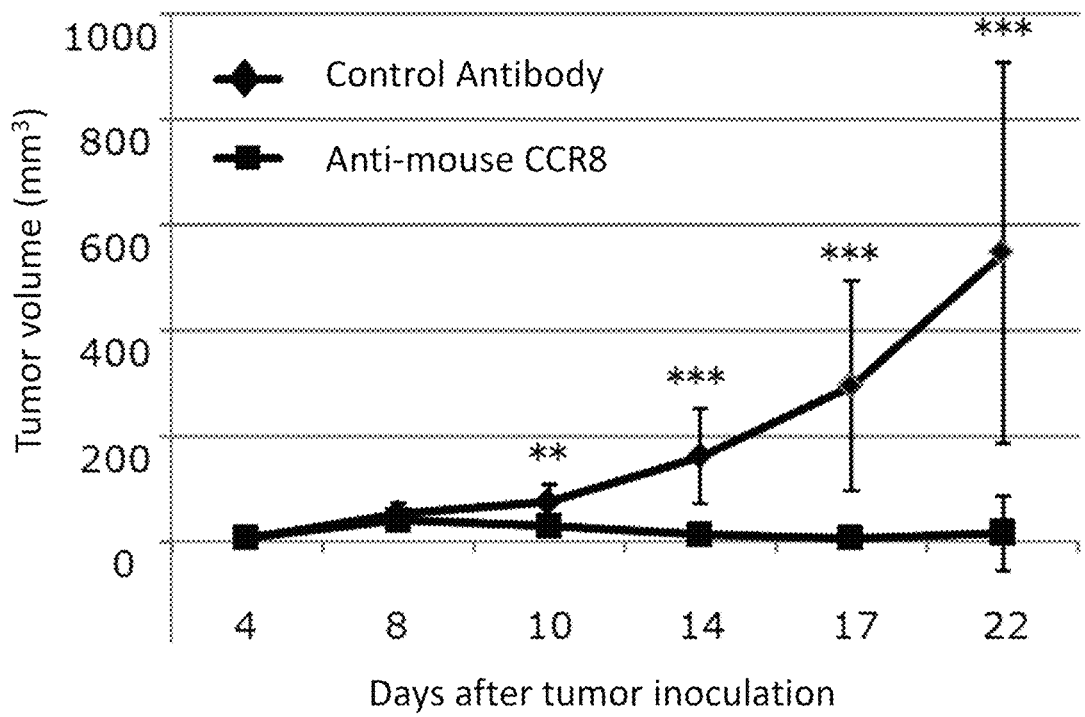

[Figure 32]
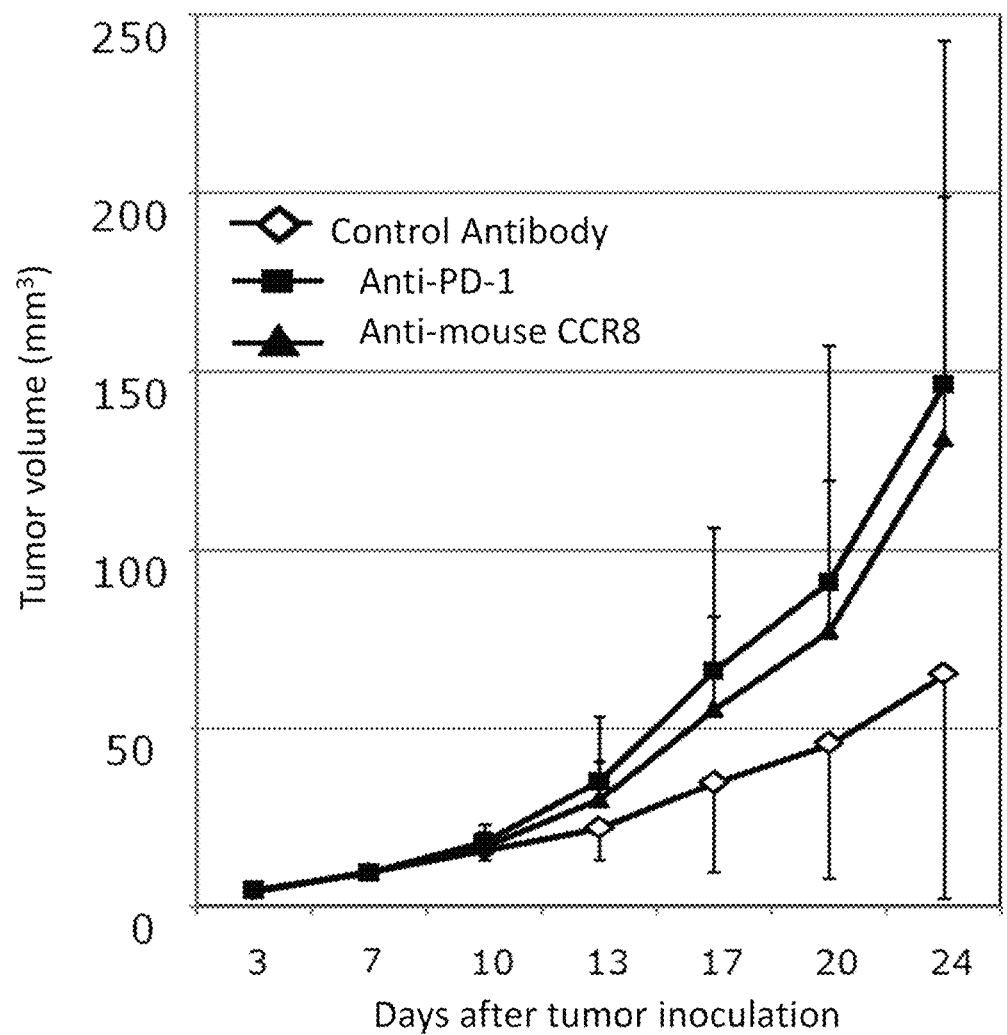

[Figure 33]
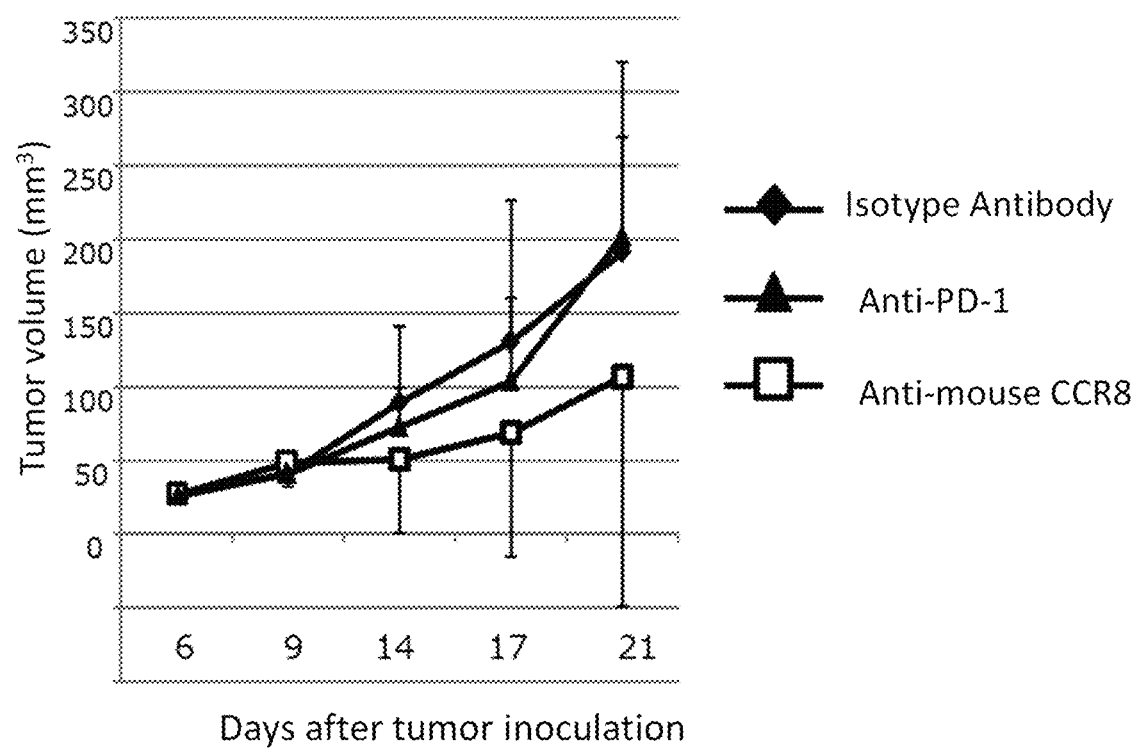

[Figure 34]
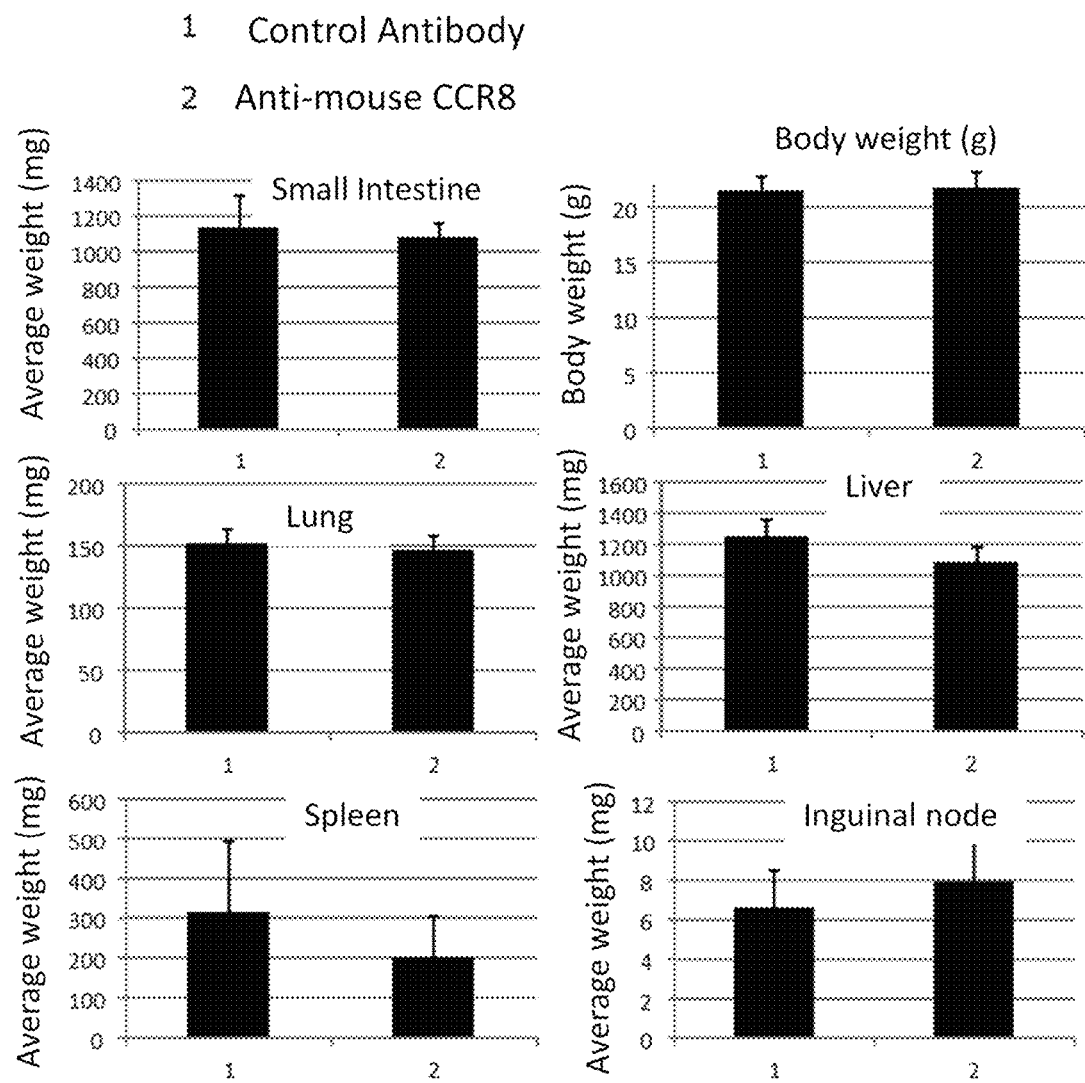

[Figure 35]
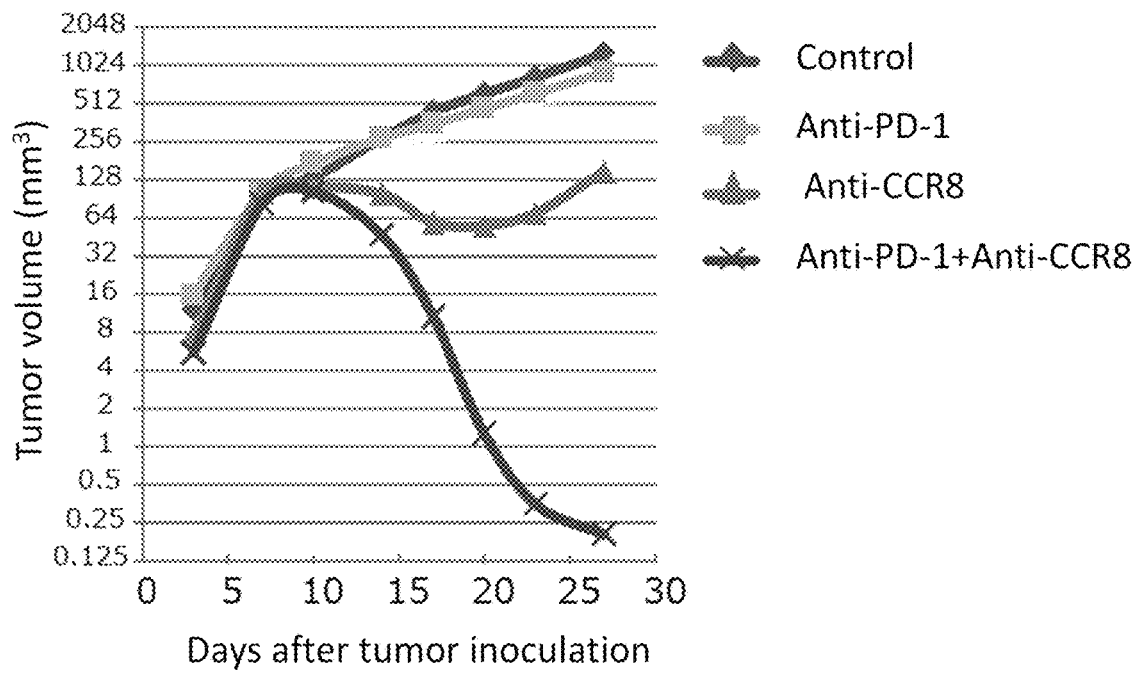
[Figure 36]
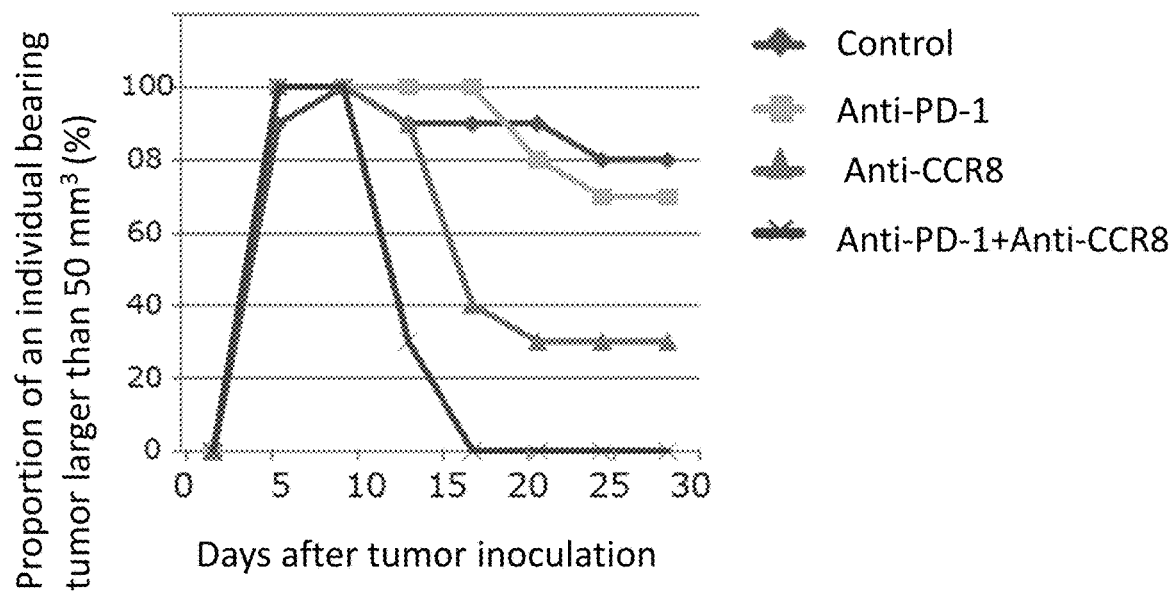

[Figure 37]
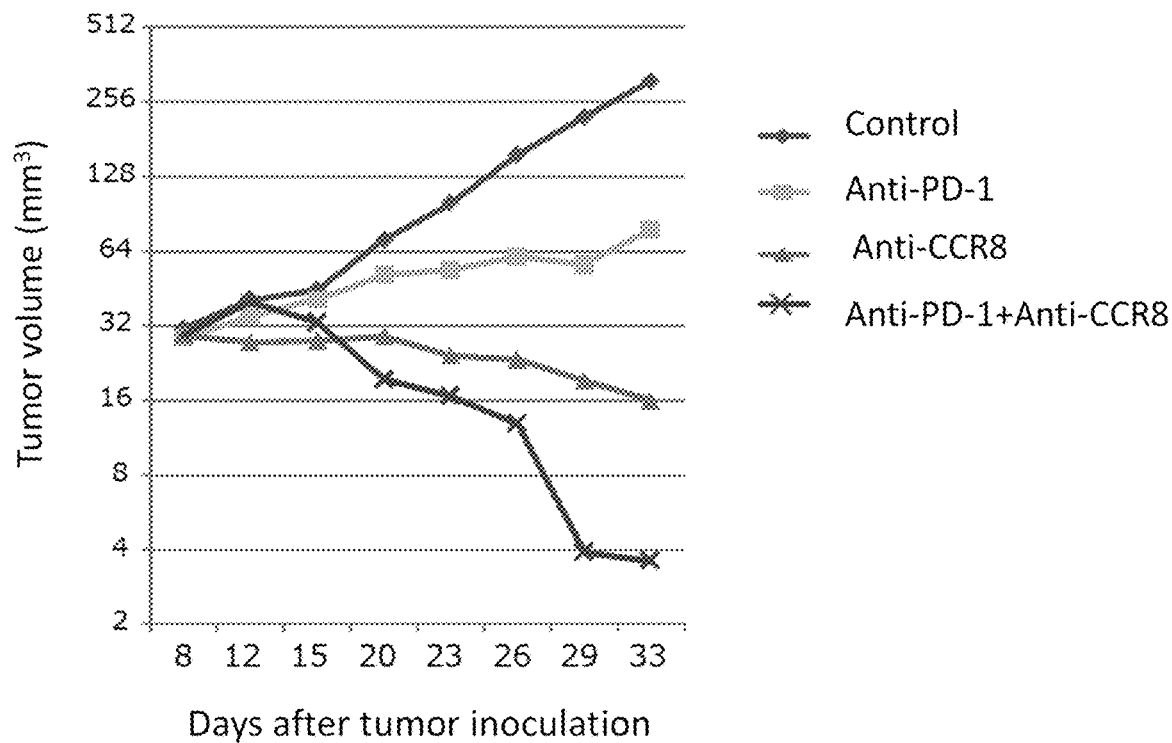
[Figure 38]
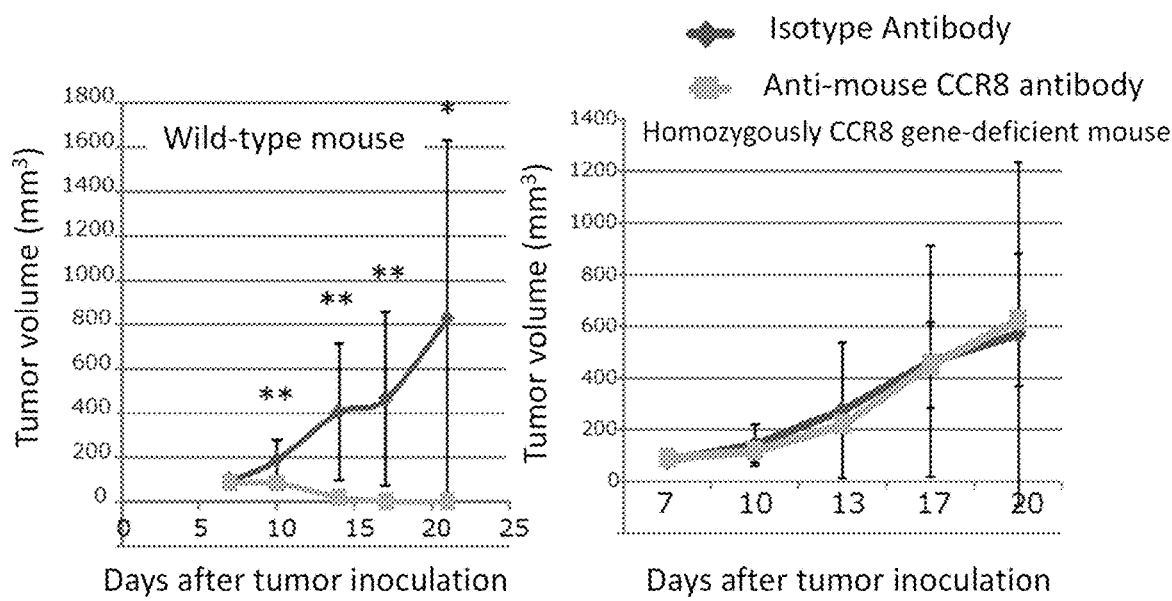

METHOD OF TREATING CANCER WITH AN ANTI-CCR8 THAT BINDS TUMOR INFILTRATING CELLS

TECHNICAL FIELD

The present invention relates to a pharmaceutical composition for cancer treatment comprising an antibody against CCR8.

BACKGROUND ART

Potent negative regulation mechanisms, including immunosuppression, mediated by regulatory T cells (Treg cells) in the tumor microenvironment are major obstacles to the treatment of tumors (Non Patent Literature 1).

For example, CD4-positive Treg cells which infiltrate tumors may be able to strongly inhibit antitumor immune response and may become a major obstacle to effective cancer treatment.

Tumor immunosuppression mediated by CD4-positive FoxP3-positive Treg cells has been sufficiently demonstrated in animal tumor models. It has been reported that systemic (including intratumoral) Treg cell removal produces an antitumor effect, wherein the removal of approximately 50% tumor-infiltrating Treg cells is not effective (Non Patent Literature 2).

It has been reported that the increased ratio of CD4-positive CD25-positive Treg cells (cell population including Treg cells) to the whole CD4-positive T cell population in humans is intratumorally detected in patients with various cancers including lung, breast, and ovary tumors, and the abundance ratio correlates negatively with the survival probabilities of the patients (Non Patent Literatures 3 to 8).

The removal of CD4-positive CD25-positive Treg cells from tumors using an anti-CD25 antibody has been confirmed to produce an antitumor effect. However, this removal is not specific for the Treg cells because CD25 is expressed on the cell surface of the CD4-positive CD25-positive Treg cells as well as newly activated effector T cells. Furthermore, the administration of an anti-CD25 antibody to mice brings about a limited antitumor effect. It has been demonstrated in various tumor models that only the antibody administration before tumor inoculation exhibits a therapeutic effect, whereas the administration of the antibody after tumor engraftment in mice rarely produces a therapeutic effect. The antitumor effect was attenuated in the case of starting the administration of an anti-CD25 antibody at post-transplant day 1, and was rarely observed in the case of starting the administration of an anti-CD25 antibody at post-transplant day 2 or later (Non Patent Literature 9).

Drug efficacy tests have been carried out so far by administering antibodies to mice for the purpose of removing Treg cells. Nonetheless, there are few reports showing an antitumor effect. Thus, it is very difficult to confirm an antitumor therapeutic effect brought about by Treg cell removal by antibody administration before inoculation (Non Patent Literature 10).

CCR8, also previously called CY6, CKR-L1 or TER1, is a G protein-coupled 7-transmembrane CC chemokine receptor protein expressed in the thymus, the spleen, etc. A gene encoding this protein resides on human chromosome 3p21. Human CCR8 consists of 355 amino acids (Non Patent Literature 11). CCL1 is known as an endogenous ligand for CCR8 (Non Patent Literature 12). Human CCR8 cDNA is constituted by the nucleotide sequence represented by Gen-Bank ACC No. M_005201.3, and mouse CCR8 cDNA is constituted by the nucleotide sequence represented by GenBank ACC No. NM_007720.2.

CITATION LIST

Non Patent Literature

[Non Patent Literature 1]
Nat. Rev. Immunol., 2006, Vol. 6, No. 4, p. 295-307
[Non Patent Literature 2]
Eur. J. Immunol., 2010, Vol. 40, p. 3325-3335
[Non Patent Literature 3]
J. Clin. Oncol., 2006, Vol. 24, p. 5373-5380
[Non Patent Literature 4]
Nat. Med., 2004, Vol. 10, p. 942-949
[Non Patent Literature 5]
J. Clin. Oncol., 2007, Vol. 25, p. 2586-2593
[Non Patent Literature 6]
Cancer, 2006, Vol. 107, p. 2866-2872
[Non Patent Literature 7]
Eur. J. Cancer, 2008, Vol. 44, p. 1875-1882
[Non Patent Literature 8]
Cell. Mol. Immunol. 2011, Vol. 8, p. 59-66
[Non Patent Literature 9]
Cancer Res., 1999 July 1; Vol. 59, No. 13, p. 3128-33
[Non Patent Literature 10]
Cancer Res., 2010, Vol. 70, No. 7, p. 2665-74
[Non Patent Literature 11]
J. Immunol., 1996, Vol. 157, No. 7, p. 2759-63
[Non Patent Literature 12]
J. Biol. Chem., 1997, Vol. 272, No. 28, p. 17251-4

SUMMARY OF INVENTION

Technical Problem

An object of the present invention is to activate the immunity by inhibiting immunosuppression mediated by Treg cells or the like and to provide a pharmaceutical composition for cancer treatment via this mechanism.

Solution to Problem

The present inventors have conducted diligent studies and consequently completed the present invention by finding that tumor-infiltrating Treg cells and tumor-infiltrating macrophage cells specifically express CCR8, and the administration of an antibody against CCR8 decreases the cell counts of the tumor-infiltrating Treg cells and the tumor-infiltrating macrophage cells and inhibits tumor growth.

Specifically, the present invention relates to:
(1) a pharmaceutical composition for cancer treatment, comprising an antibody against CCR8;
(2) the pharmaceutical composition according to (1), wherein the antibody against CCR8 is an antibody having ADCC activity;
(3) the pharmaceutical composition according to (1) or (2), wherein the antibody against CCR8 is a CCR8-neutralizing antibody;
(4) the pharmaceutical composition according to any one of (1) to (3), wherein the antibody against CCR8 has an effect of removing tumor-infiltrating Treg cells;
(5) the pharmaceutical composition according to any one of (1) to (4), wherein the antibody against CCR8 has an effect of removing tumor-infiltrating macrophage cells;

(6) the pharmaceutical composition according to any one of (1) to (5), wherein the cancer is breast cancer, colorectal cancer, kidney cancer or sarcoma;
(7) a medicament for cancer treatment, comprising a combination of an antibody against CCR8 and an anti-PD-1 antibody or an anti-PD-L1 antibody;
(8) a method for treating a cancer, comprising administering an antibody against CCR8 according to any of one (1) to (5);
(8-1) a method for treating a cancer, comprising administering an antibody against CCR8;
(8-2) the method according to (8-1), wherein the antibody against CCR8 is an antibody having ADCC activity;
(8-3) the method according to (8-1) or (8-2), wherein the antibody against CCR8 is a CCR8-neutralizing antibody;
(8-4) the method according to any one of (8-1) to (8-3), wherein the antibody against CCR8 has an effect of removing tumor-infiltrating Treg cells;
(8-5) the method according to any one of (8-1) to (8-4), wherein the antibody against CCR8 has an effect of removing tumor-infiltrating macrophage cells;
(8-6) the method according to any one of (8-1) to (8-5), wherein the cancer is breast cancer, colorectal cancer, kidney cancer or sarcoma;
(8-7) the method according to any one of (8-1) to (8-6), further administering an anti-PD-1 antibody or an anti-PD-L1 antibody;
(9) the antibody against CCR8 according to any one of (1) to (5) for treating a cancer;
(9-1) an antibody against CCR8 for treating a cancer;
(9-2) the antibody against CCR8 according to (9-1), wherein the antibody against CCR8 is an antibody having ADCC activity;
(9-3) the antibody against CCR8 according to (9-1) or (9-2), wherein the antibody against CCR8 is a CCR8-neutralizing antibody;
(9-4) the antibody against CCR8 according to any one of (9-1) to (9-3), wherein the antibody against CCR8 has an effect of removing tumor-infiltrating Treg cells;
(9-5) the antibody against CCR8 according to any one of (9-1) to (9-4), wherein the antibody against CCR8 has an effect of removing tumor-infiltrating macrophage cells;
(9-6) the antibody against CCR8 according to any one of (9-1) to (9-5), wherein the cancer is breast cancer, colorectal cancer, kidney cancer or sarcoma; and
(9-7) a combination of an antibody against CCR8 according to any one of (9-1) to (9-6) and an anti-PD-1 antibody or an anti-PD-L1 antibody for use in the treatment of a cancer.

Advantageous Effects of Invention

A pharmaceutical composition comprising the antibody of the present invention is pharmaceutically very useful for the treatment of cancers.

BRIEF DESCRIPTION OF DRAWINGS

FIG. 1 shows results of FACS analysis on kidney cancer tumor-infiltrating CD3+CD4+ T cells. A CD25 molecule and a FoxP3 molecule were each stained with an antibody and evaluated for their expression rates. CD25-expressing cells were found to also express FoxP3.

FIG. 2 shows results of flow cytometry analysis on CD45RA and CD25 expression intensity in peripheral blood mononuclear cells (hereinafter, referred to as PBMCs) of the same patient. CD3+CD4+ T cells were fractionated into 6 fractions (Fr1 to Fr6) as shown in the drawing according to CD45RA and CD25 expression levels, and cells in each fraction were recovered using a sorter. The numeric values denote the cell abundance ratio (%) of each fraction. In this case, Treg fractions are Fr1 and Fr2.

FIG. 3 shows results of flow cytometry analysis on CD45RA and CD25 expression intensity in kidney cancer tumor-infiltrating cells. Tumor-infiltrating CD3+CD4+ T cells were fractionated into 4 fractions (Fr2 to Fr5) as shown in the drawing according to CD45RA and CD25 expression levels, and cells in each fraction were recovered using a sorter. The numeric values denote the cell abundance ratio (%) of each fraction.

FIG. 4 shows results of conducting the RNA-Seq analysis of cells in each of the fractions of FIGS. 2 and 3 and studying whether any of these fractions would contain Treg cells on the basis of the mRNA expression levels of Treg-specific expressed genes FoxP3 and IKZF2. The ordinate depicts a relative mRNA expression level after normalization. The strong intratumoral expression of both the genes was observed in Fr2 and Fr3. The strong expression of IL-2 or IFNγ, which is expressed in effector cells, was observed in Fr4 and Fr5.

FIG. 5 shows results of analysis on a Treg-specific demethylation region (chrX, 49118000-49118500, hg19) at a FoxP3 gene locus in each fraction. Most of tumor-infiltrating CD3+CD4+ T cells in Fr2 and Fr3 fractions were found to be Treg cells.

FIG. 6 shows results analyzing the mRNA expression level of CCR8 in each fraction in the same way as in FIG. 4. Tumor-infiltrating Treg cell fractions Fr2 and Fr3 exhibited the strong expression of CCR8, wherein the expression was rarely observed in Treg cells in peripheral blood mononuclear cells (PBMCs).

FIG. 7 shows results of flow cytometry analysis on HEK293 cells expressing mouse CCR8. HEK293 cells were transfected with a pcDNA3.4 expression vector having an insert of the mouse CCR8 gene and drug-selected using G418. As for the degree of mouse CCR8 expression, the expression was confirmed with a PE-labeled anti-mouse CCR8 antibody. HEK293 cells transfected with a pcDNA3.4 vector and drug-selected in the same way as above were used as a negative control. Almost all the cells were found to express mouse CCR8.

FIG. 8 shows that an anti-mouse CCR8 antibody (SA214G2) has the ability to activate a signaling pathway necessary for antibody-dependent cell mediated cytotoxicity (ADCC).

FIG. 9 shows that the anti-mouse CCR8 antibody (SA214G2) has ADCC activity.

FIG. 10 shows that the anti-mouse CCR8 antibody (SA214G2) has activity of inhibiting intracellular calcium influx mediated by CCR8. An isotype control antibody was used as a negative control.

FIG. 11 shows that the anti-mouse CCR8 antibody (SA214G2) does not recognize CT26 cells. An isotype control antibody was used as a negative control.

FIG. 12 shows results of administering a control antibody at post-transplant day 3 to three BALB/c mice in which mouse colorectal cancer cell line CT26 cells were transplanted, excising tumors at post-administration day 4 or 7, and analyzing the proportion of Treg cells present therein using a flow cytometer.

FIG. 13 shows results of analyzing the proportion of CCR8+ Treg cells using a flow cytometer in the same experiment as in FIG. 12.

FIG. 14 shows results of analyzing the proportion of CCR8-positive cells in intratumoral CD11b+Gr1+CD206+ M2 macrophage cells using a flow cytometer. In both cases, 40 to 50% cells were found to be CCR8-positive M2 macrophage cells.

FIG. 15 shows the flow of an experiment of administering the anti-mouse CCR8 antibody (SA214G2) or an isotype control antibody at post-transplant day 3 to BALB/c mice in which colorectal cancer cell line CT26 cells were transplanted, excising tumors at post-transplant day 7 or 10, and examining the abundance ratios of T lymphocytes and macrophage cells present therein.

FIG. 16 shows the ratio of CD25+ FoxP3+ cells to CD45+CD4+ cells at post-transplant day 7 (d7) or 10 (d10).

FIG. 17 shows the proportion of CD11b+F4/80+ macrophage cells at post-transplant day 7 (d7).

FIG. 18 shows the abundance ratio of IA/IE-positive (IA/IE+) or IA/IE-negative cells (IA/IE−) at post-transplant day 7 (d7).

FIG. 19 shows the flow of an experiment of administering the anti-mouse CCR8 antibody (SA214G2) or an isotype control antibody (rat anti-KLH) at a single dose of 400 μg/mouse at post-transplant day 3 (d3) to BALB/c mice in which colorectal cancer cell line CT26 cells were transplanted, and measuring a tumor size every 3 to 4 days from post-transplant day 7 (d7) up to day 21 (d21).

FIG. 20 shows results of measuring the solid tumor size of each individual after inoculation and calculating a tumor volume.

FIG. 21 shows the mean tumor volume of each mouse group at each point in time after inoculation. A standard deviation is also shown. Significance level * denotes p<0.001, and significance level  denotes p<0.01 (t-test).

FIG. 22 $2 \times 10^5$ colorectal cancer cell line Colon26 cells were intracutaneously transplanted to the back of each BALB/c mouse. At post-transplant day 3 (d3), the anti-mouse CCR8 antibody (SA214G2) or an isotype control antibody was administered at a single dose of 400 μg/mouse. A tumor volume was measured every 3 to 4 days from post-transplant day 3 (d3) up to day 18 (d18). The mean tumor volume of each group at each point in time after inoculation is shown.

FIG. 23 The plot shows the mean fluorescence intensity (MFI) of each individual in FACS analysis. The central horizontal lines depict the mean MFI of 14 cases, and the vertical lines depict standard deviations. Significance level *** denotes P<0.001.

FIG. 24 shows an individual-based plot of the ratio of cells that exhibited CCR8-positive signals (percent positivity) equal to or larger than a background level obtained in an isotype control antibody, to CD3+ CD4+ FoxP3+ T cells or CD3+ CD4+ FoxP3− T cells within the human kidney cancer tumors of 14 cases. The central horizontal lines depict the mean percent positivity of the 14 cases, and the vertical lines depict standard deviations.

FIG. 25 shows a Kaplan-Meier curve as to the survival probability of each group obtained by equally dividing clear cell renal cell carcinoma patients into 2 groups with high expression (High) and with low expression (Low) on the basis of the CCR8 mRNA expression levels of intratumoral cells through the use of The Cancer Genome Atlas (TCGA) database. The ordinate depicts the survival probability, and the abscissa depicts the number of months. The numeric values denote the number of individuals in each group. The P value denotes a log-rank test value.

FIG. 26 shows results of analyzing prostate cancer patients in the same way as in FIG. 25.

FIG. 27 shows results of analyzing bladder cancer patients in the same way as in FIG. 25.

FIG. 28 shows that the anti-mouse CCR8 antibody recognizes neither MethA cells nor LM8 cells, as in FIG. 11. An isotype control antibody (Isotype) was used as a negative control.

FIG. 29 $3 \times 10^5$ osteosarcoma cell line LM8 cells were intracutaneously transplanted to the back of each C3H/He mouse. At post-transplant day 3 (d3), the anti-mouse CCR8 antibody (SA214G2) or an isotype control antibody (Control antibody) was administered at a single dose of 400 μg/mouse. A tumor volume was measured every 3 to 4 days from 7 days up to 35 days after tumor inoculation. The mean tumor volume of each group at each point in time after inoculation is shown. A standard deviation is also shown. Significance level * denotes p<0.001, significance level  denotes p<0.01, and significance level * denotes p<0.05 (t-test).

FIG. 30 $1 \times 10^5$ MethA cells were intracutaneously transplanted to the back of each Balb/c mouse. At post-transplant day 3, the anti-mouse CCR8 antibody (SA214G2) or an isotype control antibody (Control antibody) was administered at a single dose of 400 μg/mouse. A tumor volume was measured every 3 to 4 days from 11 days up to 21 days after tumor inoculation. The mean tumor volume of each group at each point in time after inoculation is shown. Significance level * denotes p<0.05 (t-test).

FIG. 31 $1 \times 10^5$ breast cancer cell line EMT6 cells were intracutaneously transplanted to the back of each Balb/c mouse. At 3 and 10 days after tumor inoculation, the anti-mouse CCR8 antibody (SA214G2) or an isotype control antibody was administered at 100 μg/mouse. A tumor volume was measured every 3 to 4 days from 4 days up to 22 days after tumor inoculation. The mean tumor volume of each group at each point in time after inoculation is shown. Significance level * denotes p<0.001, and significance level  denotes p<0.01 (t-test).

FIG. 32 $2 \times 10^5$ colorectal cancer cell line Colon26 cells were intracutaneously transplanted to the back of each BALB/c mouse. At 3 and 10 days after tumor inoculation, an anti-isotype control antibody (Isotype antibody), the mouse CCR8 antibody (SA214G2) or an anti-PD-1 antibody (RMP1-14) was administered at 400 μg/mouse. A tumor volume was measured every 3 to 4 days from 3 days up to 24 days after tumor inoculation. The mean tumor volume of each group at each point in time after inoculation is shown.

FIG. 33 $4 \times 10^5$ mouse kidney cancer-derived cell line RAG cells were intracutaneously transplanted to the back of each BALB/c mouse. 6 days after tumor inoculation, 100 μg (100 μL) of an isotype control antibody, the anti-mouse CCR8 antibody or an anti-mouse PD-1 antibody (Anti-PD-1 antibody) was intraperitoneally administered thereto. A tumor volume was measured every 3 to 4 days from 6 days up to 21 days after tumor inoculation. The mean tumor volume of each group at each point in time after inoculation is shown.

FIG. 34 $2 \times 10^5$ colorectal cancer cell line Colon26 cells were intracutaneously transplanted to the back of each BALB/c mouse. At 3 and 10 days after tumor inoculation, the anti-mouse CCR8 antibody (SA214G2) or an isotype control antibody (Control antibody) was administered at 400 μg/mouse. 24 days after tumor inoculation, each organ was recovered from the mice, and its weight was measured. The mean of 10 cases in each group is shown.

FIG. 35 $1 \times 10^5$ mouse breast cancer cell line EMT6 cells were intracutaneously transplanted to the back of each BALB/c mouse. The anti-mouse CCR8 antibody was intravenously administered thereto at 3 and 10 days after tumor inoculation, and an anti-mouse PD-1 antibody was intravenously administered thereto at 8 and 13 days after tumor inoculation. An isotype control antibody was intravenously administered to a control group at 3 and 10 days after tumor inoculation. A tumor volume was measured every 3 to 4 days from 6 days up to 27 days after inoculation. The mean tumor volume of each group at each point in time after inoculation is shown.

FIG. 36 shows the proportion of an individual bearing tumor larger than 50 mm$^3$ or smaller at each point in time after inoculation in each group in the same experiment as in FIG. 35.

FIG. 37 4.5×10$^5$ mouse kidney cancer-derived cell line RAG cells were intracutaneously transplanted to the back of each BALB/c mouse. 8 and 15 days after tumor inoculation, 100 μL of physiological saline, the anti-mouse CCR8 antibody or an anti-mouse PD-1 antibody, or the anti-mouse CCR8 antibody and the anti-mouse PD-1 antibody was intravenously administered thereto. A tumor volume was measured every 3 to 4 days from 8 days up to 33 days after tumor inoculation. The median tumor volume of each group at each point in time after inoculation is shown.

FIG. 38 2×10$^5$ CT26 cells were intracutaneously transplanted to the back of each wild-type mouse or homozygously CCR8 gene-deficient mouse of Balb/c lineage (N=5). After inoculation, an isotype control antibody or the anti-mouse CCR8 antibody was intravenously administered thereto. A tumor volume was measured every 3 to 4 days after tumor inoculation. The left diagram shows the mean tumor volume of the wild-type mice in each group at each point in time after inoculation, and the right diagram shows the mean tumor volume of the homozygously CCR8 gene-deficient mice in each group at each point in time after inoculation.

DESCRIPTION OF EMBODIMENTS

The pharmaceutical composition of the present invention comprises an antibody against CCR8.

The CCR8 of the present invention includes those derived from mice, rats, hamsters, guinea pigs, dogs, pigs, and primate mammals including monkeys and humans. Human CCR8 is preferred.

The antibody against CCR8 may be any of a human-derived antibody, a mouse-derived antibody, a rat-derived antibody, a rabbit-derived antibody and a goat-derived antibody as long as the antibody binds to CCR8. The antibody against CCR8 may be a polyclonal or monoclonal antibody thereof and may be any of a complete antibody, an antibody fragment (e.g., a F(ab')2, Fab', Fab or Fv fragment), a chimeric antibody, a humanized antibody and a complete human antibody. A human-derived antibody, a humanized antibody or a complete human antibody is preferred.

The antibody of the present invention can be produced according to an antibody or antiserum production method known in the art using a full-length protein or a partial protein of CCR8 as an antigen. Desirably, the antibody of the present invention binds to CCR8 expressed on cell surface. Therefore, the partial protein is desirably an extracellular region of CCR8. These antigens can be prepared by protein expression and purification methods known in the art.

Examples of the antigen, other than those described above, suitable for the preparation of the antibody against CCR8 include cells forced to express CCR8 by an expression vector or the like, CCR8 expression plasmid vectors, and CCR8 expression virus vectors (adenovirus vectors, etc.).

The polyclonal antibody can be produced by a method known in the art. The polyclonal antibody can be produced, for example, by immunizing an appropriate animal with an antigenic protein or a mixture thereof with a carrier protein, and harvesting a product containing an antibody against the antigenic protein from the immunized animal, followed by the separation and purification of the antibody. Examples of the animal used generally include mice, rats, sheep, goats, rabbits, and guinea pigs. In order to enhance the ability to produce antibodies, a complete Freund's adjuvant or an incomplete Freund's adjuvant can be administered together with the antigenic protein. In general, the administration is performed a total of approximately 3 to 10 times, usually once every approximately 2 weeks. The polyclonal antibody can be harvested from the blood, ascitic fluid, or the like of the animal immunized by the method described above. A polyclonal antibody titer in antiserum can be measured by ELISA. The separation and purification of the polyclonal antibody can be performed according to an immunoglobulin separation and purification method, for example, a purification method using an antigen binding solid phase or an active adsorbent such as protein A or protein G, a salting-out method, an alcohol precipitation method, an isoelectric precipitation method, electrophoresis, an adsorption and desorption method using an ion exchanger, an ultracentrifugation method, or a gel filtration method.

The monoclonal antibody can be prepared by a known general production method. Specifically, a mammal, preferably a mouse, a rat, a hamster, a guinea pig or a rabbit, is immune-sensitized with the antigen of the present invention, if necessary, together with a Freund's adjuvant, by subcutaneous, intramuscular, intravenous, intra-footpad or intraperitoneal injection once to several times. Usually, immunization was performed once to 4 times every approximately 1 to 21 days from initial immunization, and antibody-producing cells can be obtained from the immune-sensitized mammal approximately 1 to 10 days after the final immunization. The number of immunizations and the time interval can be appropriately changed according to the properties, etc. of the immunogen used.

Hybridomas secreting the monoclonal antibody can be prepared according to the method of Kohler and Milstein (Nature, 1975, vol. 256, p. 495-497) and a method equivalent thereto. Specifically, the hybridomas can be prepared by the cell fusion of antibody-producing cells contained in the spleen, the lymph node, the bone marrow or the tonsil, etc., preferably the spleen, obtained from a mammal immune-sensitized as mentioned above, with preferably mouse-, rat-, guinea pig-, hamster-, rabbit- or mammal (e.g. human)-derived, more preferably mouse-, rat- or human-derived myeloma cells lacking the ability to produce autologous antibodies.

In general, an established cell line obtained from mice, for example, P3-U1, NS-1, SP-2, 653, X63, or AP-1, can be used as the myeloma cells for use in the cell fusion.

A hybridoma clone producing the monoclonal antibody is screened for by culturing the hybridomas, for example, in a microtiter plate, measuring the reactivity of a culture supernatant in a well where growth is seen, with the antigen of the present invention used in the mouse immune sensitization mentioned above by a measurement method such as RIA, ELISA, or FACS, and selecting a clone producing the monoclonal antibody that exhibits specific binding to the antigen or hapten. Usually, a method is further used which involves immobilizing the antigen on a solid phase, and detecting an antibody in a culture supernatant binding thereto using a secondary antibody labeled with a radioactive material, a fluorescent material, an enzyme, or the like. In the case of using antigen-expressing cells, the hybridoma culture supernatant is added to the cells, and a fluorescently labeled secondary antibody can then be reacted therewith, followed by the measurement of fluorescence intensity of the cells using a fluorescent detection apparatus such as a flow cytometer to detect a monoclonal antibody capable of binding to the antigen of the present invention on the membranes of the cells.

The monoclonal antibody can be produced from the selected hybridoma by culturing the hybridoma in vitro or culturing the hybridoma in the ascitic fluid or the like of a mouse, a rat, a guinea pig, a hamster or a rabbit, etc., preferably a mouse or a rat, more preferably a mouse, and isolating the monoclonal antibody from the obtained culture supernatant or ascetic fluid of the mammal. For the in vitro culture, the hybridoma is grown, maintained and preserved according to various conditions such as the characteristics of the cell type to be cultured, the purpose of a test and research and a culture method and can be cultured using a known nutrient medium as used for producing monoclonal antibodies into a culture supernatant, or every nutrient medium induced and prepared from a known basal medium.

Examples of the basal medium include low-calcium media such as Ham' F12 medium, MCDB153 medium and low-calcium MEM medium, and high-calcium media such as MCDB104 medium, MEM medium, D-MEM medium, RPMI1640 medium, ASF104 medium and RD medium. The basal medium can contain, for example, serum, hormone, cytokine and/or various inorganic or organic substances, according to a purpose.

The monoclonal antibody can be isolated and purified, for example, by subjecting the culture supernatant or the ascetic fluid mentioned above to saturated ammonium sulfate, ion-exchange chromatography (DEAE or DE52, etc.), or affinity column chromatography using an anti-immunoglobulin column, a protein A column, or the like.

A recombinant antibody obtained by cloning an antibody gene from antibody-producing cells, for example, hybridomas, integrating the antibody gene into an appropriate vector, and transfecting a host with this vector, followed by production by use of a gene recombination technique can be used as the antibody of the present invention (e.g., Carl et al., THERAPEUTIC MONOCLONAL ANTIBODIES, published in 1990).

Specifically, mRNA encoding the variable region (V region) of the antibody is isolated from hybridomas producing the antibody of interest or immunocytes producing the antibody, for example, cells of sensitized lymphocytes immortalized with an oncogene or the like. For the mRNA isolation, total RNA is prepared by a method known in the art, for example, a guanidine ultracentrifugation method (Chirgwin, J. M. et al., Biochemistry (1979) 18, 5294-5299), and the mRNA is prepared using mRNA Purification Kit (manufactured by Pharmacia Inc.) or the like.

cDNA of the antibody V region is synthesized from the obtained mRNA using reverse transcriptase. The synthesis of the cDNA can be performed using AMV Reverse Transcriptase First-strand cDNA Synthesis Kit or the like. 5'-Ampli FINDER RACE Kit (manufactured by Clontech Laboratories, Inc) and PCR-based 5'-RACE (Frohman, M. A. et al., Proc. Natl. Acad. Sci. USA, 1988, Vol. 85, p. 8998, etc.) can be used for cDNA synthesis and amplification. The DNA fragment of interest is purified from the obtained PCR product and ligated with vector DNA. A recombinant vector is further prepared therefrom. E. coli or the like is transfected with the recombinant vector, and a colony is selected to prepare the desired recombinant vector. The nucleotide sequence of the DNA of interest is confirmed by a method known in the art, for example, a deoxy method.

Provided that the DNA encoding the V region of the antibody of interest is successfully obtained, this DNA is linked to DNA encoding the desired antibody constant region (C region) and the resultant is integrated into an expression vector. Alternatively, the DNA encoding the V region of the antibody may be integrated into an expression vector containing the DNA of the antibody C region. In order to produce the antibody used in the present invention, the antibody gene is integrated into an expression vector such that the antibody gene is expressed under the control of an expression control region, for example, enhancer/promoter. Next, host cells can be transformed with this expression vector to express the antibody.

For the expression of the antibody gene, DNA encoding the heavy chain (H chain) and DNA encoding the light chain (L chain) of the antibody may be separately integrated into expression vectors, with which a host is co-transformed, or the DNA encoding the H chain and the DNA encoding the L chain may be integrated into a single expression vector, with which a host is transformed (see WO94/11523).

A so-called phage display technique (Nature Biotechnology 23, 1105 (2005)) can also be used as a method, other than those described above, for preparing the antibody of the present invention. Specifically, for example, an antibody gene library prepared by a method known in the art using human or animal (e.g., rabbit, mouse, rat, or hamster) B lymphocytes as a material, or an antibody gene library completely synthesized by selection and engineering from a human or animal germ line sequence is displayed on, for example, bacteriophages, E. coli, yeast or animal cell surface, or liposomes. In this respect, examples of the form of the antibody to be displayed on the cell surface include IgG molecules, IgM molecules, Fab fragments, and single-strand Fv (scFv) fragments.

The antibody fragment gene thus obtained can be recombined with a corresponding region of an IgG antibody gene by a method known in the art to obtain an antibody gene. Then, the gene thus obtained can be integrated into an appropriate vector, with which a host is transfected, followed by the production of the antibody by use of a gene recombination technique (e.g., Carl et al., THERAPEUTIC MONOCLONAL ANTIBODIES, published in 1990).

The antibody of the present invention includes antibodies artificially engineered for the purpose of, for example, reducing xenoantigenicity against humans, for example, chimeric antibodies, humanized antibodies and complete human antibodies.

The antibody of the present invention may be a conjugated antibody in which the antibody is bound with any of various molecules such as polyethylene glycol (PEG), radioactive substances, toxins, and sugar chains. Such a conjugated antibody can be obtained by chemically modifying the obtained antibody. The method for modifying the antibody has already been established in the art. The antibody according to the present invention also encompasses these conjugated antibodies.

The antibody of the present invention encompasses an antibody having a Fc region bound with N-glycoside-linked sugar chains which are free from a fucose bound with N-acetylglucosamine at their reducing termini. Examples of the antibody having a Fc region bound with N-glycosidelinked sugar chains which are free from a fucose bound with N-acetylglucosamine at their reducing termini include antibodies prepared using α1,6-fucosyltransferase gene-deficient CHO cells (International Publication Nos. WO 2005/035586 and WO 02/31140). The antibody of the present invention having a Fc region bound with N-glycoside-linked sugar chains which are free from a fucose bound with N-acetylglucosamine at their reducing termini has high ADCC activity.

The antibody of the present invention may be fused at its N terminus or C terminus with an additional protein (Clinical Cancer Research, 2004, 10, 1274-1281). The protein to be fused can be appropriately selected by those skilled in the art.

The antibody fragment is a portion of the antibody of the present invention mentioned above and means a fragment having CCR8-specific binding activity as in the antibody. Examples of the antibody fragment can specifically include Fab, F(ab')2, Fab', single-strand antibody (scFv), disulfide-stabilized antibody (dsFv), dimerized V region fragment (diabody), and CDR-containing peptides (Expert Opinion on Therapeutic Patents, Vol. 6, No. 5, p. 441-456, 1996).

Alternatively, the antibody of the present invention may be a bispecific antibody which has two different antigenic determinants and binds to different antigens.

The ADCC (antibody-dependent cell mediated cytotoxicity) activity means in vivo activity of damaging tumor cells or the like by activating effector cells via the binding of the Fc region of the antibody bound with a cell surface antigen or the like on the tumor cells or the like to a Fc receptor present on the effector cell surface. Examples of the effector cells include natural killer cells and activated macrophages.

The antibody of the present invention is preferably an antibody having ADCC activity against cells expressing CCR8 because this antibody can remove Treg cells or macrophage cells. Whether or not the antibody of the present invention has such ADCC activity can be measured by, for example, a method described in Examples mentioned later.

The antibody against CCR8 contained in the pharmaceutical composition of the present invention is preferably a CCR8-neutralizing antibody from the viewpoint of suppressing the intratumoral accumulation of Treg cells or macrophage cells. The CCR8-neutralizing antibody means an antibody having neutralizing activity against CCR8. Whether or not the antibody of the present invention has neutralizing activity against CCR8 can be determined by measuring the presence or absence of suppression of the physiological effect of CCL1 on CCR8. Examples thereof include, but are not limited to, the measurement of the binding of CCL1 to CCR8, the migration of CCR8-expressing cells by CCL1, increase in intracellular $Ca^{++}$ level by CCL1, and variation in the expression of a gene sensitive to CCL1 stimulation. This can also be determined by a method described in Examples mentioned later.

The antibody against CCR8 of the present invention preferably has an effect of removing tumor-infiltrating Treg cells. Whether or not the antibody of the present invention has the effect of removing tumor-infiltrating Treg cells can be determined by, for example, a method described in Examples mentioned later.

The antibody against CCR8 of the present invention preferably has an effect of removing tumor-infiltrating macrophage cells. Whether or not the antibody of the present invention has the effect of removing tumor-infiltrating macrophage cells can be determined by, for example, a method described in Examples mentioned later.

The antibody of the present invention is useful as a pharmaceutical composition. Thus, the pharmaceutical composition comprising the antibody of the present invention can be administered orally or parenterally and systemically or locally. For example, intravenous injection such as infusion, intramuscular injection, intraperitoneal injection, subcutaneous injection, transnasal administration, or inhalation can be selected as parenteral administration.

The "cancer" for the "pharmaceutical composition for cancer treatment" of the present invention includes every solid cancer and blood cancer. Specifically, examples thereof include breast cancer, uterine corpus cancer, cervical cancer, ovary cancer, prostate cancer, lung cancer, stomach cancer (gastric adenocarcinoma), non-small cell lung cancer, spleen cancer, head and neck squamous cell carcinoma, esophageal cancer, bladder cancer, melanoma, colorectal cancer, kidney cancer, non-Hodgkin lymphoma, urothelial cancer, sarcoma, blood cell carcinoma (leukemia, lymphoma etc.), bile duct carcinoma, gallbladder carcinoma, thyroid carcinoma, prostate cancer, testicular carcinoma, thymic carcinoma, and hepatocarcinoma. Preferably, examples thereof include breast cancer, uterine corpus cancer, ovary cancer, lung cancer, colorectal cancer, kidney cancer and sarcoma, and more preferably, examples thereof include breast cancer, colorectal cancer, kidney cancer, and sarcoma.

The "cancer" for the "pharmaceutical composition for cancer treatment" of the present invention is preferably a cancer expressing a tumor-specific antigen.

The "cancer" described in the present specification means not only epithelial malignant tumors such as ovary cancer and stomach cancer but non-epithelial malignant tumors including hematopoietic cancers such as chronic lymphocytic leukemia and Hodgkin lymphoma. In the present specification, terms such as "cancer", "carcinoma", "tumor", and "neoplasm" can be used interchangeably with each other without differentiating thereamong.

The antibody against CCR8 of the present invention may be administered as a concomitant drug in combination with an additional drug in order to (1) complement and/or potentiate the therapeutic effect of the pharmaceutical composition of the present invention,
(2) improve the pharmacokinetics and absorption of the pharmaceutical composition of the present invention, and reduce the dose thereof, and/or
(3) reduce the adverse reaction of the pharmaceutical composition of the present invention.

The concomitant drug of the antibody against CCR8 of the present invention and an additional drug may be administered in the form of a combination drug containing both the ingredients in one preparation or may be administered in the form of separate preparations. This administration as separate preparations includes concurrent administration and staggered administration. For the staggered administration, the antibody of the present invention may be administered first, and the additional drug may be administered later, or the additional drug may be administered first, and the compound of the present invention may be administered later. Their respective administration methods may be the same or different.

Examples of the additional drug that may be used in combination with the antibody against CCR8 of the present invention include anti-PD-1 antibodies, anti-PD-L1 antibodies and anti-CTLA-4 antibodies. An anti-PD-1 antibody or an anti-PD-L1 antibody is preferred, and an anti-PD-1 antibody is more preferred.

In the present invention, examples of the anti-PD-1 antibody include nivolumab and pembrolizumab.

In the present invention, examples of the anti-PD-L1 antibody include atezolizumab, avelumab, and durvalumab.

In the present invention, examples of the anti-CTLA-4 antibody include ipilimumab.

The patient intended by the pharmaceutical composition of the present invention is expected to be a cancer patient or a patient suspected of having a cancer. The effective dose is selected from the range of 0.01 mg to 100 mg per kg of body weight per dose. Alternatively, the dose can be selected from 5 to 5000 mg, preferably 10 to 500 mg, per patient. However, the pharmaceutical composition comprising the antibody of the present invention or an antibody fragment thereof is not limited by these doses. Also, the dosing period can be appropriately selected according to the age and symptoms of the patient. The pharmaceutical composition of the present invention may further contain a pharmaceutically acceptable carrier or additive depending on an administration route. Examples of such a carrier and additive include water, pharmaceutically acceptable organic solvents, collagen, polyvinyl alcohol, polyvinylpyrrolidone, sodium alginate, water-soluble dextran, pectin, methylcellulose, ethylcellulose, casein, diglycerin, propylene glycol, polyethylene glycol, Vaseline, human serum albumin (HSA), mannitol, sorbitol, lactose, and surfactants acceptable as pharmaceutical additives. The additive used is selected appropriately or in combination from among those described above according to a dosage form, though the additive is not limited thereto.

Hereinafter, the present invention will be specifically described with reference to Examples. However, the present invention is not limited by Examples given below. Methods described in Molecular Cloning: A Laboratory Manual, 2nd Edition (Cold Spring Harbor Laboratory) were used as gene manipulation approaches unless otherwise specified.

Example 1

Extraction and Analysis of Kidney Cancer Tumor-Infiltrating Cells and PBMCs

The following analysis was conducted using a portion of primary tumor tissues excised by surgical treatment from clear cell renal cell carcinoma (ccRCC) patients (3 cases) who were not preoperatively treated with an anticancer agent, radiation, or the like. After tumor weight measurement, tumor masses were cut into 2 mm square with scissors, and tumor tissue homogenates were prepared using Tumor Dissociation Kit, human (130-095-929, Miltenyi Biotec) and gentleMACS™ Dissociator (Miltenyi Biotec, 130-093-235) according to the protocol attached to the kit. The homogenates were passed through a 70 um cell strainer and subjected to hemolysis treatment, followed by the removal of debris and dead cells in a solution of 30% Percoll in PBS to obtain tumor tissue single cells.

Peripheral blood mononuclear cells (PBMCs) of the same patient were separated from peripheral blood by the density gradient centrifugation method using Ficoll-Paque PLUS (GE Healthcare Japan Corp.). After cell count measurement, the separated intratumoral cells and PBMCs were treated with Human TruStain FcX™ (BioLegend, Inc., 422-301) and Zombie NIR™ Fixable Viability kit (BioLegend, Inc., 423105) according to the attached protocols and stained 30 minutes in ice. Then, the cells were washed once with 2% FCS/HEPES/HBSS and then stained with the following labeling antibodies according to the protocols attached to the labeling antibodies.

The cell surface of tumor-infiltrating cells was stained through reaction for 30 minutes in ice using an anti-CD3 antibody (BioLegend, Inc., Clone UCHT1), an anti-CD4 antibody (BioLegend, Inc., Clone OKT4), and an anti-CD25 antibody (BioLegend, Inc., Clone BC96). The cells were washed twice with 2% FCS/HEPES/HBSS and then fixed and membrane-permeabilized using Foxp3/Transcription Factor Staining Buffer Set (eBioscience, Inc., 00-5523-00) according to the protocol attached to the kit. FoxP3 was further stained using a PE-labeled anti-FoxP3 antibody (eBioscience, Inc., Clone PCH010). The cells were washed once with a washing solution attached to the kit and then analyzed by flow cytometry (BD Biosciences, BD LSR-Fortessa). Almost all the CD4+CD25+ T cells within the ccRCC tumors were confirmed to express FoxP3, a marker of Treg cells (FIG. 1).

Subsequently, the tumor-infiltrating cells and the PBMCs described above were stained with an anti-CD3 antibody, an anti-CD4 antibody, an anti-CD45RA antibody (BD Biosciences, Clone HI100) and an anti-CD25 antibody. CD3+ CD4+ T cells were two-dimensionally developed on the basis of CD45RA and CD25 expression levels. The results about the PBMCs are shown in FIG. 2, and the results about the tumor-infiltrating cells are shown in FIG. 3. The tumor-infiltrating cells were fractionated into 4 fractions of strongly positive cells (Fr2), weakly positive cells (Fr3), and negative cells (Fr4 and Fr5) as shown in FIG. 1C with CD3+CD4+CD45RA- and CD25 expression intensity as an index using a cell sorter (FACSAria II), and cells contained in each fraction were recovered. The PBMCs were also two-dimensionally developed, as in the tumor-infiltrating cells, and fractionated into Fr1 to Fr6 as shown in FIG. 2 with CD45RA and CD25 expression intensity as an index, and cells contained in each fraction were recovered.

Example 2

Separation of RNA from Fractionated Cells and cDNA Sequence Analysis

The cells separated and recovered from each fraction were lysed in RLT buffer (Qiagen N.V.), and total RNA was extracted using Agencourt RNAClean XP (Beckman Coulter, Inc.). The recovered RNA was prepared into cDNA using SMART-Seq v4 Ultra Low Input RNA kit for Sequencing (Clontech Laboratories, Inc.), and a library was prepared using KAPA Hyper Prep Kit for illumina (Kapa Biosystems, Inc.). For the cDNA synthesis and the library preparation, quality control was constantly performed using Agilent 2100 Bioanalyzer (Agilent Technologies, Inc.) to confirm that these procedures were free from problems. The finished cDNA library was titrated using a KAPA library Quantification kit Illumina Platforms (Kapa Biosystems, Inc.). Then, DNA sequencing was performed by paired end reads using Hiseq 4000 (Illumina, Inc.) to obtain 20,000,000 reads or more of 100-base pair sequence data per sample (Fastq file).

The raw data (Fastq file) was analyzed by FastQC, and adaptor sequences and repeat sequences were removed using CutAdapt. Pairs of each paired end read were matched using cmpfastq_pe program. hg38 was used as a reference sequence in genome mapping, and the reads were mapped onto the genome at default setting using TOPHAT2 program having Bowtie 2. The mapped reads were sequence-sorted using SAMtools program and counted using HTSEQ program. The count data was normalized using Deseq 2 program. Among the obtained fractions, a fraction containing Treg cells was confirmed by the following method.

Treg cells are known to constitutively express FoxP3 and Ikzf2 genes as marker genes and to rarely secrete IFNγ or IL2 even when activated by stimulation. Whether or not to contain Treg cells may be confirmed to some extent by examining the expression levels of these genes. As a result of examining the expression levels of these genes as to each fraction of the tumor-infiltrating cells and the PBMCs on the basis of the RNA-Seq data described above, Ikzf2 and FoxP3 were found to be specifically expressed in Fr2 and Fr3 of the tumor-infiltrating cells and Fr2 of the PBMCs and rarely expressed in the other fractions (FIG. 4). Also, IFNγ (IFN-gamma) and IL2 were found to be specifically expressed in Fr4 and Fr5 of the tumor-infiltrating cells and Fr4 and Fr5 of the PBMC cells and not expressed in the other fractions (FIG. 4). In conclusion, the Treg cells were found to be contained in Fr2 and Fr3 of the tumor-infiltrating cells and Fr2 of the PBMCs and not contained in the other fractions.

Example 3

Measurement of Demethylation Rate of FoxP3 Region

The demethylation rate of a FoxP3 region serves as an index for accurately determining the proportion of Treg cells. Therefore, the cells in Fr2 to Fr5 of the kidney cancer tumor-infiltrating cells obtained as described above were studied for the demethylation rate of the FoxP3 region. A region demethylated in a Treg cell-specific manner resides (chrX, 49118000-49118500, hg19) in a particular CpG region within the first intron of the FoxP3 gene. The cells contained in each fraction of the tumor-infiltrating cells may be analyzed for the demethylation of this region to verify whether the fraction obtained this time consists of only Treg cells or other cells also coexist therewith.

Each fraction (Fr2, Fr3, Fr4, and Fr5) of the tumor-infiltrating CD4+ T cells was recovered, and genome DNA was recovered by use of the phenol extraction method. The genome DNA was treated with bisulfite using MethylEasy Xceed kit (Human Genetic Signatures), and the FOXP3 intron 1 region (chrX, 49118000-49118500, hg19), a Treg cell-specific demethylation region, was subjected to amplicon PCR. DNA methylation was detected using a prepared methylated DNA-specific FAM fluorescent probe and demethylation-specific VIC fluorescent probe and QuantStudio 3D digital PCR system (Applied Biosystems, Inc.). After the amplicon PCR, the numbers of light emissions from the FAM and VIC fluorescent probes were counted, and the DNA methylation rate was calculated from the ratio between these numbers of fluorescence emissions and used as the methylation rate of each fraction (Fr2 to Fr5).

As a result, 95% or more CpG sequences within the FOXP3 intron 1 region (chrX, 49118000-49118500) were demethylated in the cells contained in Fr2 and Fr3 of the tumor-infiltrating cells, whereas the demethylation rates of Fr4 and Fr5 were 50% or less. In conclusion, almost all the cells contained in Fr2 and Fr3 were found to be Treg cells (FIG. 5).

Example 4

Identification of CCR8

In order to identify a gene of one group specifically expressed in the Treg cells (Fr2 of the tumor-infiltrating cells), hierarchical clustering analysis was conducted on the gene expression data on the PBMC-derived CD4+ T cell fraction of the same patient as in each tumor-derived CD4+ T cell fraction. CCR8 was identified as a gene that was expressed in Fr2 of the Treg cells and rarely expressed in tumor-derived Fr5 and Fr4 and Fr5 of the PBMCs (FIG. 6).

Example 5

Preparation of Cells Forced to Express Mouse CCR8

Full-length ORF of mouse CCR8 (hereinafter, also referred to as mCCR8) was inserted to an expression vector (pcDNA3.4) to construct pcDNA3.4-mCCR8 plasmid. The nucleotide sequence was changed to have codons with high usage frequency in mammals without changing the amino acids. HEK293 cells were transfected with pcDNA3.4 or the pcDNA3.4-mCCR8 expression plasmid using Lipofectamine 3000 and drug-selected at a geneticin (G418) concentration of 1 mg/ml for 2 weeks.

Surviving cells were dissociated with trypsin and washed with DMEM/10% FCS medium. Then, a PE-labeled anti-mCCR8 antibody (clone SA214G2) diluted 1/200 was added thereto and reacted on ice for 30 minutes. Then, the cells were washed once with DMEM/10% FCS to label mCCR8 expressed on the cell surface. A cell population expressing mCCR8 was enriched by sorting using a cell sorter (FACSAria II). The positive cell population was cultured at 37° C. for 2 weeks in a CO2 incubator in the presence of DMEM/10% FCS (medium containing 1 mg/ml G418). For the cells transformed with pcDNA3.4, only drug selection was performed, and sorting was not performed. In order to confirm expression, both the cells were stained with a commercially available anti-PE-labeled anti-mouse CCR8 antibody (clone SA214G2) and analyzed using a flow cytometer (FACSAria II). The results are shown (FIG. 7). The expression of mCCR8 was observed in 99% or more of the cells transformed with pcDNA3.4-mCCR8 compared with the cells transformed with pcDNA3.4.

Example 6

Study on Ability of Anti-Mouse CCR8 Antibody (SA214G2) to Stimulate FcγR

An anti-mouse CCR8 antibody (clone SA214G2, purchased from BioLegend, Inc.) was evaluated for the ability to stimulate FcgR, necessary for its ADCC activity, using mFcγRIV ADCC Reporter Bioassays Core kit (Promega Corp.). This kit indicates the activation of FcγR on effector cells by the expression level of luciferase gene linked downstream of NFAT promoter in the cells. The activation of FcγR signals can be quantified by quantifying this expression level.

Hereinafter, the procedures will be briefly described. $1 \times 10^5$ cells/well of mCCR8-expressing HEK293 target cells (target cells) dissociated with trypsin were mixed with FcγR-expressing effector cells attached to the kit at a ratio of 1:1.5 in a 96-well plate. Immediately after the cell mixing, the antibody against mCCR8 was added thereto. The concentration was set to 33 ug/ml to 0.033 ug/ml as shown in FIG. 8 (N=2). Only the effector cells were used as a negative control. 14 hours after the antibody addition, the cells were recovered, and the luciferase activity was measured (FIG. 8). A mean of N=2 is shown.

As a result, the luciferase activity was not observed at any of the antibody concentrations for the negative control, whereas antibody concentration-dependent activity was observed in the target cell addition group. The ordinate depicts a relative value of luminescence intensity. As seen from FIG. 8, the largest activity value was approximately 6000 relative light units (R.L.U), and the EC50 value (approximately 3500 R.L.U) was approximately 0.1 μg/ml (lines in the drawing). These results demonstrated that the anti-mouse CCR8 antibody (SA214G2) can activate FcγRIV.

Example 7

Measurement of ADCC Activity

The anti-mCCR8 antibody (SA214G2) was evaluated for its cytotoxic activity using the stably mCCR8-expressing HEK293 cells prepared in Example 5.

The spleen of a C57BL/6 mouse was separated, and spleen cells were recovered through a cell strainer. The cells were washed and then reacted with a biotinylated anti-CD49b (clone DX5) antibody at 4° C. for 30 minutes. After washing, NK cells were purified using streptavidin microbeads (Miltenyi Biotec) and used as effector cells. The HEK293 cells expressing mouse CCR8 were stained with Cell Trace Violet (CTV) (Thermo Fisher Scientific Inc., C34557) at a final concentration of 2.5 uM and used as target cells. These cells were mixed at a ratio of effector cells:target cells=5:1 (effector cell count: $2.5 \times 10^5$ cells) in a 96-well plate (200 µL/well). The anti-mouse CCR8 antibody or an isotype control antibody (rat IgG2b, clone RTK4530) was added thereto at a final concentration of 1 µg/ml, followed by overnight culture in a CO2 incubator of 37° C. Then, PE-labeled annexin V (Annexin V-PE, Medical & Biological Laboratories Co., Ltd. (MBL), 4696-100) diluted 1/100 was added according to the attached protocol, and the cells were stained at 37° C. for 30 minutes and then washed once. The proportion of annexin V-positive apoptotic cells in the CTV-stained target cells was analyzed using a flow cytometer. The test was carried out in triplicate (N=3), and a mean and a standard deviation thereof are shown. A typical example of two similar experiments is shown (FIG. 9). The addition of the anti-mouse CCR8 antibody compared with the isotype control antibody significantly increased the proportion of annexin V-positive cells in the target cells by approximately 6 times. In conclusion, the anti-mouse CCR8 antibody (SA214G2) was found to have ADCC activity.

Example 8

Measurement of Neutralizing Activity Against CCR8

The anti-mouse CCR8 antibody (SA214G2) was evaluated for its neutralizing activity against CCR8 with intracellular calcium influx mediated by mouse CCL1 (ligand of mouse CCR8) as an index using HEK293 cells stably expressing mouse CCR8.

The following reagents were used in calcium measurement. HEPES (Wako Pure Chemical Industries, Ltd., CAS. NO. 7365-45-9) HBSS(+) without Phenol Red (Wako Pure Chemical Industries, Ltd.) Fluo 3-AM (cat F023, Dojindo Laboratories) Probenecid (CAS-No: 57-66-9, Nacalai Tesque, Inc.) Pluronic F127 (P3000MP; Life Technologies Corp.) 10 mM HEPES/HBSS/0.1% BSA Buffer (HEPES (final concentration: 10 mM) and BSA (final concentration: 0.1%) were added to HBSS)

Fluo 3-AM and Pluronic F127 were dissolved at final concentrations of 4 µmol/L and 0.04%, respectively, in 10 mM HEPES/HBSS Buffer. The cells were suspended in this solution and incubated at 37° C. for 1 hour so that Fluo 3-AM was taken up by the cells. Then, the cells were washed three times with 10 mM HEPES/HBSS/0.1% BSA solution and suspended at a cell concentration of $2 \times 10^5$ cells/ml in 10 mM HEPES/HBSS/0.1% BSA solution containing 1.25 uM probenecid. Then, the cells were incubated at 37° C. for 10 minutes in a CO2 incubator. The anti-mCCR8 antibody (SA214G2) or an isotype control antibody (Clone LTF-2, Bio X Cell) was further added thereto at a concentration of 5 µg/ml. The cells were further incubated at 37° C. for 20 minutes.

2 mL of the solution of the cells was placed in a quartz glass cuvette and loaded in a spectrophotometer HITACHI F7000 with the temperature of a measurement room preset to 35° C. The measurement conditions were as described below.

Excitation wavelength: 508.0 nm, fluorescence (measurement) wavelength: 527.0 nm, excitation-side slit: 5 nm, fluorescence-side slit: 5 nm, photomultiplier voltage: 950 V, response: 0.5 s The cells were incubated with stirring using a stirrer for approximately 30 seconds until the fluorescence wavelength was stabilized. When the wavelength was stabilized, mouse CCL1 was added thereto at a final concentration of 50 nM (4 µL) to start measurement. As a result of the measurement, the administration of the anti-mCCR8 antibody in advance was found to almost completely suppress intracellular calcium influx mediated by mCCL1 (FIG. 10). Such suppression was not observed by the addition of the control antibody. The gaps in the graphs were derived from the opening and closing of the cover of the instrument in order to administer the agonist to the cells. In conclusion, the anti-mCCR8 antibody (SA214G2) was found to have neutralizing activity against mouse CCR8.

Example 9

Confirmation of Expression of mCCR8 in CT26

CT26 cells were cultured in a 6-well dish, and the culture solution was removed when the cells became approximately 50% confluent. 5 ml of 10 mM EDTA/PBS was added thereto, and the cells were incubated at 37° C. for 5 minutes. As a result, almost all the cells were dissociated, suspended using a pipette and were thereby able to be separated into almost single cells. The cells were washed twice with D-MEM/10% FCS, suspended in D-MEM/10% FCS, and stained in ice with LIVE/DEAD® Fixable Near-IR Dead Cell Stain Kit (Thermo Fisher Scientific Inc., L34975) and an APC-labeled anti-mCCR8 (SA214G2) or APC-labeled isotype control antibody. 1 hour later, the cells were washed three times with D-MEM/10% FCS and analyzed for a mCCR8 expression rate using a flow cytometer (FACSCanto II). A background was set using the isotype control antibody, and the proportion of positive cells (P6) equal to or larger than the background level and median APC fluorescence were calculated (FIG. 11). As a result, no difference in median APC fluorescence intensity was observed, and the positive cells were rarely observed (0.2%). In conclusion, the CT26 cells were not recognized by the anti-mCCR8 antibody, and the CT26 cells were confirmed to not express mCCR8.

Example 10

Confirmation of CCR8 Expression in Tumor-Infiltrating Cells Using Colorectal Cancer Cell Line CT26 Cells $3 \times 10^5$ CT26 cells (50 µL) were intracutaneously transplanted to the back of each Balb/c mouse (7 w, female) (N=3). At post-transplant day 3, 400 µg of a rat anti-KLH (keyhole limpet hemocyanin, Clone LTF-2) antibody (IgG2b) was intraperitoneally administered thereto. At post-administration days 4 (4d) and 7 (7d), tumors were recovered from the 3 individuals (N=3). The tumor masses of the CT26 cells were chopped with scissors, and tumor-infiltrating cells were prepared using a commercially available kits (Tumor Dissociation Kit, mouse, Miltenyi Biotec and gentleMACS™ Dissociator, Miltenyi Biotec, cat. 130-095-929) according to the protocols attached to the kits.

The prepared cells were passed through a 70 um cell strainer and then washed twice with 10 mM HEPES/HBSS/ 2% FBS. Then, the cells were treated with an erythrocyte lysis solution (Miltenyi Biotec) for 5 minutes for the removal of erythrocytes and further washed twice with 2% FCS (fetal calf serum)/10 mM HEPES/HBSS buffer. The tumor-infiltrating cells were divided into two parts, one of which was used in the identification of Treg cells and the other of which was used in the identification of myeloid (macrophage) cells. The cells were stained using the following method and antibodies. The antibodies, staining reagents, and assay buffers used were as described below.

The following antibodies were used.
(Antibody set for Treg cell confirmation)
PE anti-mouse/rat FoxP3 (clone FJK-16s), eBioscience, Inc.
Anti-mouse CD4 PerCP/Cy5.5 (clone RM4-5), eBioscience, Inc.
Anti-mouse CD8a FITC (clone 5H10-1), BioLegend, Inc.
Bv421 anti-mouse CD25 (clone PC61), BioLegend, Inc.
Bv510 anti-mouse CD45 (clone 30-F11), BioLegend, Inc.
AF647 Anti-mouse CCR8 (clone SA214G2), BioLegend, Inc.
AF647 Isotype Control (clone RTK4530), BioLegend, Inc. (CCR8-negative control)
(Antibody set for myeloid and macrophage cell confirmation)
AF647 Anti-mouse CCR8 (clone SA214G2), BioLegend, Inc.
AF647 Isotype Control (clone RTK4530), BioLegend, Inc. (CCR8-negative control)
Bv510 anti-mouse CD45 (clone 30-F11), BioLegend, Inc.
FITC anti-mouse Gr-1 (clone RB6-8C5), BioLegend, Inc.
Bv421 anti-mouse F4/80 (clone BM8), BioLegend, Inc.
PECy7 anti-mouse CD11b (clone M1/70), BioLegend, Inc.
PerCP/Cy5.5 Anti-mouse MHC class II IA/IE (clone M5/114.15.2), BioLegend, Inc.
PE anti-mouse CD206 (clone C068C2), BioLegend, Inc.
(Other reagents used)
Zombie NIR Fixable Viability Kit (cat no. 423106), BioLegend, Inc.
BD Pharmingen Transcription Factor buffer Set (cat no. 562574)
BD Pharmingen Lysing Buffer (cat no. 555899)
HBSS(−), Wako Pure Chemical Industries, Ltd., 084-08345
FCS (HyClone Laboratories Inc., cat no. 5H30070.03)

The staining method was as follows: the infiltrating cells were stained in ice for 30 minutes using a reagent of Zombie NIR Fixable Viability Kit. The cells were washed once with 2% FCS/10 mM HEPES/HBSS. Then, Treg- and CCR8-positive cells were stained with Bv510-labeled anti-CD45, PerCP/Cy5.5-labeled anti-mouse CD4, FITC-labeled anti-mouse CD8, Bv421-labeled anti-mouse CD25, and AF647-labeled anti-mouse CCR8 antibody (or AF647-labeled isotype control antibody). Monocytic cells were stained with Bv510-labeled anti-CD45, FITC anti-mouse Gr-1, PECy7 anti-mouse CD11b, Bv421 anti-mouse F4/80, PerCP/Cy5.5-labeled MHC class 2 (IA/IE) antibody, and PE-labeled anti-mouse CD206 antibody.

The staining was carried out in ice for 30 minutes. The cells were washed twice with 2% FCS/HEPES/HBSS and then fixed using a commercially available kit (FoxP3 staining kit, eBioscience, Inc.) according to the attached protocol, and intracellular FoxP3 was stained using a PE-labeled anti-FoxP3 antibody. The cells were washed with a buffer attached to the kit and then analyzed using a flow cytometer.

CD45+CD4+ T cells were analyzed. A negative cell region in the CD45+CD4+ T cells was determined by staining with an isotype control antibody, and cells positive to both anti-mouse CD25 and anti-mouse FoxP3 antibodies were used as Treg cells to calculate the frequency of presence 4 days after administration (7 days after inoculation) and 7 days after administration (10 days after inoculation). As a result, approximately 23% (4d) and approximately 30% (7d) of the CD45+CD4+ cells within the mouse tumors were CD25+ FoxP3+ cells (FIG. 12).

Next, CCR8 expression in the CD45+CD4+CD25+ FoxP3+ T cells was analyzed. A negative cell region in the CD45+CD4+CD25+ FoxP3+ cells was determined by staining with an isotype control antibody, and cells positive to an anti-mouse CCR8 antibody were used as CCR8+ Treg cells to calculate the frequency of presence 4 days after administration (7 days after inoculation) and 7 days after administration (10 days after inoculation) (FIG. 13). As a result, approximately 50% (4d) and approximately 67% (7d) of the CD45+CD4+CD25+ FoxP3+ T cells within the mouse tumors were CCR8+ cells (FIG. 13).

As for myeloid cells, the myeloid population was gated on CD45+ cells and FSC/SSC using a flow cytometer and analyzed for the proportion of CCR8+ cells in CD11b+Gr1+ CD206+ cells. As a result, 40 to 50% cells both 7 days after inoculation (4 days after administration) and 10 days after inoculation (7 days after administration) were found to be CCR8-positive (FIG. 14). Also, the CCR8 expression rate in CD45+CD11b+F4/80+ cells (N=3) as a macrophage cell population different therefrom was measured in the same way as above. As a result, 45.3% (standard deviation: ±8.2%) of the cells were confirmed to express CCR8 at post-transplant day 10 (7d). From these results, at least CD4+CD25+ FoxP3+ T cells and CD11b+Gr1+CD206+ macrophages (called M2 macrophages) as tumor-infiltrating cells were found to express CCR8.

Example 11

Study on Effect of Removing Tumor-Infiltrating Treg Cells or Tumor-Infiltrating Macrophage Cells by Anti-mCCR8 Antibody Administration 3×10⁵ CT26 cells (50 uL) were intracutaneously transplanted to the back of each Balb/c mouse (7 w, female). 3 days after inoculation, 400 μg (liquid volume: 400 μL) of a rat anti-mouse CD198 (CCR8) antibody (clone SA214G2, BioLegend, Inc.) or an isotype control antibody (Clone LTF-2) was administered into the tail vein (each group N=3). 7 days after tumor inoculation (4 days after antibody administration) and 10 days after tumor inoculation (7 days after antibody administration), tumors were recovered, and tumor-infiltrating cells were prepared and analyzed (FIG. 15).

Tumor-infiltrating Treg cells were recovered in the same way as in Example 10. The antibodies used were the same as in Example 10.

First, the infiltrating cells were stained in ice for 30 minutes using Zombie NIR Fixable Viability Kit. The cells were washed once with 2% FCS/10 mM HEPES/HBSS and then stained with Bv510-labeled anti-CD45, PerCP/Cy5.5-labeled anti-mouse CD4, FITC-labeled anti-mouse CD8 antibody, Bv421-labeled anti-mouse CD25, and AF647-labeled anti-mouse CCR8 antibody (or AF647-labeled isotype control antibody). The staining was carried out in ice for 30 minutes. The cells were washed twice with 2%

FCS/HEPES/HBSS and then fixed using a commercially available kit (FoxP3 staining kit, eBioscience, Inc.) according to the attached protocol, and intracellular FoxP3 was stained using a PE-labeled anti-FoxP3 antibody. The cells were washed with a buffer attached to the kit and then analyzed using a flow cytometer.

CD45+CD4+ FoxP3+CD25+ cells were used as mouse Treg cells. A negative cell region in the Treg cells was determined by staining with an AF647-labeled isotype control antibody, and cells positive to an AF647-labeled anti-mouse CCR8 antibody compared with the control were used as CCR8-positive cells to calculate the frequency thereof.

As a result, as shown in FIG. 16, the percent positivity of CD45+CD4+CD25+ FoxP3+ T cells (Treg cells) in the mice given the anti-mouse CCR8 (SA214G2) antibody was approximately 80% 7 days after tumor inoculation (4 days after antibody administration) and approximately 40% 10 days after tumor inoculation (7 days after antibody administration 7) (FIG. 16) when the proportion of intratumoral CD45+CD4+CD25+ FoxP3+ T cells (Treg cells) in the mice given the isotype antibody was defined as 100% (10 days after tumor inoculation). Significance level ** was P<0.01 (t test). These results showed that approximately 60% of the tumor-infiltrating Treg cells were removed by the anti-CCR8 antibody 7 days after anti-CCR8 antibody administration.

In the same way as above, tumor-infiltrating cells were separated from tumors at post-transplant day 7 (d7), and among CD45+ cells, a myeloid population was gated on FSC/SSC (referred to as FSC/SSC+), followed by the analysis of CD11b+F4/80+ cells in the cells. F4/80 (Ly719) is a marker of mouse mature macrophages and monocytes. As shown in FIG. 17, the abundance ratio of CD11b+F4/80+ cells was decreased in the anti-mCCR8 antibody administration group (N=3) compared with the isotype control (N=3) (t test; P=0.062). The graph shows the abundance ratio of F4/80+ cells in a CD45+ FSC/SSC+ mononuclear cell population.

The abundance ratio of IA/IE-positive or class 2 (IA/IE)-negative cells in the F4/80+ cells shown in FIG. 17 is further shown as to MHC (tumor histocompatibility antigen) class 2 molecules. As shown in FIG. 18, in the anti-mCCR8 antibody administration group (N=3) compared with the isotype control (N=3), the IA/IE-negative group exhibited a decreasing trend, and the IA/IE-positive group was significantly decreased (t test; significance level *; P<0.05). In conclusion, the mouse CT26 intratumoral monocyte/macrophage population or a portion of the population was found to have a decreased intratumoral cell count.

Example 12

Evaluation of Antitumor Effect of Anti-mCCR8 Antibody Administration Using Colorectal Cancer-Derived CT26

$3 \times 10^5$ colorectal cancer-derived CT26 cells (50 uL) were intracutaneously transplanted to the back of each Balb/c mouse (7 weeks old, female). 3 days after tumor inoculation, 400 μg (400 μL) of a rat anti-mouse CD198 (CCR8) antibody (clone SA214G2, BioLegend, Inc.) was intravenously administered thereto (N=10). An isotype control antibody was administered to a control (N=10). Tumor volumes were measured every 3 to 4 days from 8 days after tumor inoculation (5 days after antibody administration). The tumor volume (mm³) was calculated according to major axis (mm)×minor axis (mm)×minor axis (mm)/2 (FIG. 19).

As a result, no significant difference was observed in the anti-mCCR8 administration group compared with the isotype control antibody administration group at post-transplant day 7, whereas the tumor volume of the anti-mCCR8 antibody administration group was significantly decreased at 11, 14, 17 and 21 days after tumor inoculation (significance level: *; P<0.001 at days 11 and 14, ; P<0.01 at days 17 and 21). Furthermore, in the anti-mouse CCR8 antibody administration group, the tumor volume was decreased at post-transplant day 14 or later, and the tumors disappeared almost completely at day 17 (individual-based data is shown in FIG. 20, and mean data is shown in FIG. 21). From these results, it was concluded that the anti-mCCR8 antibody administration suppressed the functions of mCCR8 expressed on Treg and monocytes/macrophages pointed out as immunosuppressive cells, or killed (removed) these expressing cells through the ADCC activity of the antibody so that tumor immunity was enhanced, leading to the regression and disappearance of the tumors.

As already reported by many literatures, etc., in the case of administering an antibody specific for mouse CD25 (anti-CD25), a marker of mouse Treg cells, to mice and thereby removing mouse Treg cells, the administration before tumor inoculation exhibits a weak antitumor effect and the administration at post-transplant day 2 or later exhibits no antitumor effect. We also carried out the administration of the anti-CD25 antibody at post-transplant day 3 using the same CT26 cell system as that used this time, but observed no antitumor effect. From these results, it was concluded that the anti-mCCR8 antibody has stronger drug efficacy than that of the anti-CD25 antibody.

Example 13

Next, anti-PD-1 (clone RMP1-14, Bio X Cell), an antibody specific for mouse PD-1, was evaluated for its drug efficacy using CT26 and comparatively studied with anti-mCCR8. $2 \times 10^5$ colorectal cancer-derived CT26 cells (50 μL) were intracutaneously transplanted to the back of each Balb/c mouse (7 weeks old, female). The anti-PD-1 antibody (200 μg/head, i.p.) was administered a total of three times every 3 to 4 days from post-transplant day 7.

As a result, an antitumor effect was observed in the group given the anti-PD-1 antibody (N=8) compared with a group given an isotype control antibody (N=8). The mean tumor volume and standard deviation of the isotype control were 601.7±378.1 mm³, 956.3±467.7 mm³ and 1528.4±774.1 mm³ at 14, 17 and 20 days after tumor inoculation, respectively, while the mean tumor volume and standard deviation of the anti-PD-1 antibody administration group were 175.3±42.6 mm³, 174.7±55.8 mg and 209.6±99.8 mm³ at 14, 17 and 20 days after tumor inoculation, respectively. The anti-PD-1 antibody significantly suppressed increase in tumor volume as compared with the control at all of 14, 17 and 20 days after tumor inoculation. However, an individual whose tumor disappeared completely was 1 out of 8 mice in the observation period (up to post-transplant day 20). On the other hand, the complete disappearance of tumors was observed in all of 10 cases in the same period as above by anti-mCCR8 antibody administration. From these results, it was concluded that the anti-mCCR8 antibody has stronger drug efficacy than that of the anti-PD-1 antibody in the standard administration method.

Example 14

Confirmation of Presence or Absence of Induction of Autoimmune Disease in Mouse Given Anti-mCCR8 Antibody Next, the states of the mice of Example 12 were evaluated up to post-administration day 18. No significant difference in body weight in this period was found between the control antibody administration group and the anti-CCR8 antibody administration group. Piloerection was not observed in both the groups. These mice were dissected at post-administration day 18. Although the presence or absence of enlargement of the lymph node and the intestinal tract was studied in the anti-CCR8 administration group compared with the control, the enlargement was not observed without any difference between the groups. From these findings, it was concluded that any sign of autoimmune disease was not observed in the period when an antitumor effect was exerted on the mice given the anti-CCR8 antibody. Papers have reported that, in general, if Treg is removed from the whole body of a mouse to the extent that an antitumor effect is induced, severe autoimmune disease is induced around 14 days after removal. This is a matter of concern for tumor immunotherapy including Treg suppression therapy. The results obtained this time showed that any autoimmune disease was not induced even at post-antibody administration day 18 in the mice in which a strong anti-tumor immunity effect was observed by anti-CCR8 antibody administration. One of the explanations therefor is the low expression of mouse and human CCR8 in PBMCs, the spleen, and the lymph node compared with tumor tissues according to reports. However, none of the previous reports state whether or not an autoimmune disease is induced by removing or functionally inhibiting CCR8-expressing Treg cells in these peripheral tissues. Here, it was found for the first time that these approaches induce no autoimmune disease. This effect may be unexpectable from the previous findings.

Example 15

Evaluation of Antitumor Effect of Anti-mCCR8 Antibody Administration Using Colorectal Cancer-Derived Colon-26

$2 \times 10^5$ colorectal cancer-derived Colon-26 cells (50 μL) were intracutaneously transplanted to the back of each Balb/c mouse (7 weeks old, female). 3 days after tumor inoculation, 400 μg (400 μL) of a rat anti-mouse CCR8 antibody (clone SA214G2, BioLegend, Inc.) was intravenously administered thereto (N=10). An isotype control antibody was administered to a control (N=10). Tumor volumes were measured every 3 to 4 days from 3 days after tumor inoculation (5 days after antibody administration). The tumor volume (mm³) was calculated according to major axis (mm)×minor axis (mm)×minor axis (mm)/2. The point in time when the tumor reached an endpoint volume (800 mm³) was used as the endpoint of each animal. As a result, increase in tumor volume was suppressed in the anti-mCCR8 administration group compared with the isotype control antibody administration group at 14 and 18 days after tumor inoculation. The mean tumor volume at day 14 was 451.3 mm³ (standard deviation: ±177.5 mm³) in the isotype control antibody administration group and 322.6 mm³ (standard deviation: ±146.0 mm³) in the anti-CCR8 antibody administration group. An individual having a tumor volume of 350 mm³ or larger at day 14 was 9 out of 10 cases in the isotype control group and 4 out of 10 cases in the anti-mCCR8 administration group. There was a significant difference with P=0.019 in the Pearson's chi-square test as to this segregated form. Thus, the difference was observed in the number of individuals whose tumor volume reached 350 mm³ at day 14. Also, the mean tumor volume at post-transplant day 18 was 874.7 mm³ (standard deviation: ±269.2 mm³) in the isotype control antibody administration group and 585.4 mm³ (standard deviation: ±401.7 mm³) in the anti-CCR8 antibody administration group (FIG. 22). An individual having a tumor volume of 600 mm³ or larger at day 18 was 9 out of 10 cases in the isotype control group and, on the other hand, 4 out of 10 cases in the anti-mCCR8 administration group. There was a significant difference with P=0.019 in the Pearson's chi-square test as to this segregated form. Thus, the difference was observed in the number of individuals whose tumor volume reached 600 mm³ at day 18. Further, the point in time when the tumor volume reached 800 mm³ was preset as an endpoint. An individual regarded as being dead with the tumor volume exceeding 800 mm³ was observed in neither of the groups up to day 14 and was 7 out of 10 cases in the isotype control group and 3 out of 10 cases in the anti-CCR8 antibody group at day 18. As a result of studying a difference in the survival probability at day 18 by the Pearson's chi-square test, there was a significant difference in the survival probability with P=0.025.

No antitumor effect was observed in an anti-PD-1 (clone RMP1-14, Bio X Cell) administration group compared with a group given an isotype control antibody in a similar experiment using the same cell line as above. In conclusion, the anti-mCCR8 antibody exhibited a higher antitumor effect on anti-PD-1 antibody-resistant Colon26 cells.

Example 16

Analysis on Expression of CCR8 in Human Kidney Cancer Infiltrating Cells

The expression of CCR8 was analyzed in human kidney cancer tumor-infiltrating cells of 14 cases. The backgrounds of the 14 kidney cancer patients were 11 males and 3 females for sex, a median age of 68.5 years, and pathological stages of T1A for 6 patients, T1B for 2 patients, T3A for 5 patients, and T3b for 1 patient. Specifically, kidney cancer primary tumor-infiltrating cells were isolated from the 14 kidney cancer (clear cell renal cell carcinoma, ccRCC) patients in the same way as in FIG. 1 of Example 1, stained with anti-CD4 (BioLegend, Inc., Clone OKT4), anti-CD3 (BioLegend, Inc., Clone UCHT1), anti-CD45RA (BD Biosciences, Clone HI100), anti-CD8 (BioLegend, Inc., RPA-T8), anti-CCR8 (BioLegend, Inc., Clone L263G8), and anti-FoxP3 (eBioscience, Inc., Clone 236A/E7) or an anti-FoxP3 isotype control antibody, and analyzed by flow cytometry (BD Biosciences, BD LSRFortessa). CD3+CD8+ T cells and CD3+CD4+ T cells were analyzed. The CD3+CD4+ T cells were further divided into 2 groups according to the presence or absence of FoxP3 expression and analyzed. A FoxP3 expression-negative control was prepared by staining with the isotype control antibody. The mean value of FACS analysis (MFI) of each patient sample was used as the expression intensity of CCR8. Table 1 shows mean MFI of staining with the anti-CCR8 antibody or the isotype control antibody thereof, and a standard deviation thereof.

TABLE 1

|  | Cell | | | | | |
|---|---|---|---|---|---|---|
|  | CD8+ T | | FoxP3− CD4+ T | | FoxP3+ CD4+ T | |
|  | Antibody | | | | | |
|  | Isotype | Anti-mCCR8 | Isotype | Anti-mCCR8 | Isotype | Anti-mCCR8 |
| Mean MFI | 84.9 | 267 | 56.9 | 423 | 131.3 | 3507.2 |
| Standard deviation | 26.8 | 159 | 62.1 | 297.5 | 59 | 1466.3 |

The CD8+ T cells were found to rarely express CCR8 (Table 1). The CD4+ FoxP3− T cells slightly expressed CCR8, whereas the CD4+ FoxP3+ T cells had 8 times or more the mean MFI of the CD4+ FoxP3− T cells, revealing that the CD4+ FoxP3+ T cells significantly strongly express CCR8 (Table 1). FIG. 23 shows the results of Table 1 in a graph form. Each plot of the graph shows the mean CCR8 expression level (MFI) of each patient sample in a flow cytometer. The horizontal lines of the graph depict the mean MFI of the samples. The bars depict standard deviations. Significance level *** denotes P<0.001. From these results, the CCR8 protein was found to be specifically expressed on the surface of CD3+CD4+ FoxP3+ T cells which infiltrate tumors in human kidney cancer (ccRCC). These results are also consistent with the results of the mRNA expression analysis by the RNA-Seq analysis.

Tumor-infiltrating CD4+ T cells in the 14 ccRCC samples described above were subjected to flow cytometry analysis using FoxP3 and CCR8. The ratio of CCR8-positive cells to FoxP3-positive cells and the ratio of CCR8-positive cells to FoxP3-negative cells were plotted on a sample basis (FIG. 24). Staining with an isotype control antibody was used as negative standards for both FoxP3 and CCR8, and cells having a value equal to or more than this threshold were used as positive cells. As a result, the CCR8 expression rate of intratumoral CD3+CD4+ FoxP3+ T cells was approximately 75%, and the CCR8 expression rate of CD3+CD4+ FoxP3− T cells was approximately 10%.

From these results, CCR8 was found to be expressed in most of FoxP3-expressing Treg cells among human kidney cancer tumor-infiltrating cells and expressed in approximately 10% of CD4-positive T cells other than the Treg cells. From these results, the CCR8 expression rate of human intratumoral FoxP3-positive Treg cells was similar to that of mouse intratumoral Treg cells, indicating the possibility that the anti-human CCR8-specific antibody can remove most of tumor-infiltrating FoxP3-positive Treg cells, as in mice.

Example 17

Correlation of CCR8 Expression Rate of Tumor-Infiltrating Cells in Various Cancers with Survival Probability FoxP3 gene has been identified as a gene that is specifically expressed in Treg cells and not expressed in tumor cells or most of normal human cells. For example, FoxP3 gene as a marker gene of Treg cells, CD3G gene as a marker gene of T cells and NK cells, and CD8A gene as a marker gene of CD8-positive T cells are known as so-called marker genes, which are expressed only in certain specific cells as mentioned above.

It has also been reported as to the FoxP3 gene, a marker gene of Treg cells, that the mRNA expression level of the FoxP3 gene within each tumor may be measured and thereby used as an index for the abundance ratio of Treg cells within the tumor (Cell, 2015, Vol. 160, p. 48-61).

As also reported in this paper, whether the intratumoral abundance ratio of Treg cells is related to a survival probability may be analyzed by drawing a Kaplan-Meier survival curve as to the intratumoral expression rate (Treg abundance ratio) of the marker gene and patients' survival probabilities through the use of a RNA-Seq database such as TCGA. The RNA-Seq data on tumor masses is mixed data on mRNA expressed in both tumor cells and infiltrating cells present therein (lymphocytes, vascular cells, etc.). However, a gene shown to be not expressed in tumor cells can be regarded as a gene expressed in tumor-infiltrating cells. Through the use thereof, the tumor-infiltrating cells can be identified by the analysis as described above, i.e., analysis on marker gene expression using the RNA-Seq data on tumor masses. Furthermore, the expression level of a marker gene in a tumor mass can be regarded as the product of an expressing cell count of particular cells, corresponding to the marker gene, infiltrating the tumor mass, and the expression level of the marker gene in each expressing cell.

In this context, if the expression level of the marker gene in each cell is almost constant among individuals, the expression level is in direct proportion to an infiltrating cell count. Thus, an intratumoral expressing cell count can be calculated on an individual basis by use of this expression level and can be compared among individuals.

(CCR8 Expression Analysis at Cell Level)

RNA expression data from 1037 different types of human cell lines is registered in a public database CCLE (Cancer Cell Line Encyclopedia). Whether CCR8 or CD3G gene would be expressed in cancer cells other than T cells or normal cells was analyzed using the database.

The mRNA expression of CD3G and CCR8 was analyzed as to kidney cancer-, prostate cancer- and bladder cancer-derived cell lines using the CCLE database.

The cell lines examined were 40 kidney cancer-derived cell lines; VMRCRCW, SKRC20, SNU34, SKRC31, UOK10, SLR20, OSRC2, TUHR14TKB, SLR24, HK2, A498, RCC4, KMRC1, RCC10RGB, ACHN, SLR25, SNU1272, UMRC6, SLR23, 769P, SLR21, HEKTE, CAKI1, TUHR4TKB, KMRC2, VMRCRCZ, KMRC3, KMRC20, CAKI2, BFTC909, 7860, A704, TUHR10TKB, SLR26, UMRC2, CAL54, FURPNT1, FURPNT2, HEK293, and G402; 8 prostate cancer-derived cell lines; VCAP, LNCAPCLONEFGC, DU145, PC3, 22RV1, PRECLH, MDAPCA2B, and NCIH660; and 2 bladder cancer-derived cell lines; TCBC14TK and TCBC2TKB. In all of these solid cancer cell lines examined, the expression of CCR8 and CD3G was at the same level as the background level, and no mRNA expression was observed (even the largest value indicating expression was $1/500$ or less of the expression level of G3PDH, and all the other values were $1/1000$ or less of the expression level of G3PDH). In short, CCR8 and CD3G were able to be confirmed to be rarely expressed on solid cancer cells. Primary normal cells derived from each human tissue were also analyzed in the same way as above. CCR8 and CD3G were found to be expressed only in some hematopoietic cells and rarely expressed in the other tissues-derived primary normal cells.

These results showed that the cells of these 3 cancers express neither CCR8 nor CD3G. Thus, it was concluded that TCGA RNA expression data used for tumor masses of kidney cancer, prostate cancer and bladder cancer reflects the mRNA expression of CCR8 and CD3G in infiltrating normal cells, other than cancer cells, present in the tumor masses.

(Analysis Using Public TCGA Database)

Next, the ratio of the CCR8 gene to the CD3G gene (CCR8/CD3G) expressed in the tumor of kidney cancer, prostate cancer, or bladder cancer, and patients' survival probabilities were analyzed through the use of the public TCGA database. A gene that most highly correlated (Pearson's correlation) in terms of expression with the CCR8 and CD3G genes within these 3 tumors was found to be various genes specifically expressed in T cells (FoxP3, CD5, IL7R, etc. with correlation coefficient r of 0.7 or more). These results indicate that CCR8 or CD3G is not expressed on tumor cells themselves and is specifically expressed on tumor-infiltrating expressing cells (particularly, T cells). However, a CCR8-expressing cell population was used here because this does not deny that CCR8 is expressed on infiltrating cells other than T cells. CD3G, as already reported in papers, etc., is specifically expressed on T cells and NK cells. Also, T cells are major tumor-infiltrating cells. Therefore, an infiltrating T cell count can be hypothesized from a CD3G expression level. Thus, the CCR8/CD3G value can be defined as a CCR8-expressing cell count per T cell count present within a tumor.

The CCR8/CD3G ratio and patients' survival probabilities were analyzed as to these 3 carcinomas using a Kaplan-Meier curve. For kidney cancer, Kidney Renal Clear Cell Carcinoma (TCGA, Provisional) data in the TCGA data was used, and 523 cases having complete RNA expression data and patients' survival probability data were used. Likewise, for prostate cancer, Prostate Adenocarcinoma (TCGA, Provisional) data in the TCGA data was used, and 490 cases having complete RNA expression data and patients' survival probability data were used.

Also, for bladder cancer, Bladder Urothelial Carcinoma (TCGA, Provisional) data in the TCGA data was used, and 392 cases having complete RNA expression data and patients' survival probability data were used.

Patients of each cancer were equally divided into 2 groups (the kidney cancer patients were odd-numbered and therefore divided into 261:262) with high CCR8/CD3G expression values and with low CCR8/CD3G expression values, followed by Kaplan-Meier survival curve analysis using analytical software R (R-Studio). The log-rank test was conducted as a significant difference test. The results about the kidney cancer are shown in FIG. 25, the results about the prostate cancer are shown in FIG. 26, and the results about the bladder cancer are shown in FIG. 27. The vertical lines in the graphs show that the patients survived but were treated as dropouts (corresponding to so-called censors) at the point in this time because the evaluation period was terminated at this point in time. The values on the abscissa depict the number of months in all the graphs.

As a result, in all the 3 carcinomas, the groups with high CCR8/CD3G values had significantly low patients' survival probabilities. The groups with a high ratio of human tumor-infiltrating CCR8-expressing cells to T cells were found to have a reduced survival probability. This suggests that in humans as well, CCR8-expressing cells have a suppressive effect on tumor immunity. This suggests the possibility that, as in the antitumor effect of the anti-mCCR8 antibody administered to mice, intratumoral CCR8-expressing cells in humans are specifically removed or killed by some method to thereby enhance tumor immunity and elevate a survival probability.

Example 18

Confirmation of Expression of Mouse CCR8 in LM8 Cells and MethA Cells

Osteosarcoma-derived LM8 cells or skin fibrosarcoma-derived MethA cells were cultured in a 6-well dish, and the culture solution was removed when the cells became approximately 50% confluent. 5 ml of 10 mM EDTA/PBS was added thereto, and the cells were incubated at 37° C. for 5 minutes. As a result, almost all the cells were dissociated, suspended using a pipette and were thereby able to be separated into almost single cells. The cells were washed twice with D-MEM/10% FCS, suspended in D-MEM/10% FCS, and stained in ice with LIVE/DEAD® Fixable Near-IR Dead Cell Stain Kit (Thermo Fisher Scientific Inc., L34975) and an anti-mouse CCR8 (SA214G2) or isotype control antibody. 1 hour later, the cells were washed three times with D-MEM/10% FCS and analyzed for a mouse CCR8 expression rate using a flow cytometer (FACSCanto II). A background was set using the isotype control antibody, and the proportion of positive cells equal to or larger than the background level and median fluorescence were calculated (FIG. 28). As a result, no difference in median PE fluorescence intensity was observed in both the cells, and the positive cells were not observed. In conclusion, these cells were not recognized by the anti-mouse CCR8 antibody and were confirmed to neither express mouse CCR8 nor retain an epitope reactive with the antibody.

Example 19

Evaluation of Antitumor Effect of Anti-Mouse CCR8 Antibody Administration Using Osteosarcoma-Derived LM8

$3 \times 10^5$ mouse osteosarcoma-derived LM8 cells (50 uL) were intracutaneously transplanted to the back of each C3H/He mouse (7 weeks old, male). 3 days after tumor inoculation, 400 μg (400 μL) of a rat anti-mouse CCR8 antibody (clone SA214G2, BioLegend, Inc.) was intraperitoneally administered thereto (N=11). An isotype control antibody was administered to a control (N=10). Tumor volumes were measured every 3 to 4 days from 7 days after tumor inoculation (4 days after antibody administration). The tumor volume ($mm^3$) was calculated according to major axis (mm)×minor axis (mm)×minor axis (mm)/2 (FIG. 29). As a result, the mean tumor volume of the anti-mCCR8 administration group compared with the isotype control antibody administration group was significantly decreased at all the points in time of measurement at post-transplant day 18 or later (significance level: *; P<0.05 at day 18, ; P<0.01 at days 21, 24, 27 and 31, *; P<0.001 at day 35). Furthermore, the tumors disappeared in 6 out of 11 mice in the anti-mouse CCR8 antibody administration group and 1 out of 10 mice in the isotype control antibody administration group at post-antibody administration day 31. There was a significant difference (P=0.031) in the Pearson's chi-square test conducted as to this segregated form.

Example 20

Evaluation of Antitumor Effect of Anti-Mouse CCR8 Antibody Administration Using Skin Fibrosarcoma-Derived MethA $1 \times 10^5$ skin fibrosarcoma-derived MethA cells (50 uL) were intracutaneously transplanted to the back of each Balb/c mouse (7 weeks old, female). 3 days after tumor inoculation, 400 μg (400 μL) of a rat anti-mouse CCR8 antibody (clone SA214G2, BioLegend, Inc.) was intraperitoneally administered thereto (N=5). An isotype control antibody was administered to a control (N=5). Tumor volumes were measured every 3 to 4 days from 11 days after tumor inoculation (8 days after antibody administration). The tumor volume ($mm^3$) was calculated according to major axis (mm)×minor axis (mm)×minor axis (mm)/2 (FIG. 30).

As a result, the mean tumor volume of the anti-mouse CCR8 administration group compared with the isotype control antibody administration group was significantly decreased at all the points in time of measurement at post-transplant day 11 or later (significance level: *; P<0.05 at all the points in time). Furthermore, the tumors disappeared in 5 out of 5 mice in the anti-mouse CCR8 antibody administration group and 0 out of 5 mice in the isotype control antibody administration group at post-antibody administration day 21. There was a significant difference (P=0.0016) in the Pearson's chi-square test conducted as to this segregated form.

Example 21

Evaluation of Antitumor Effect of Anti-Mouse CCR8 Antibody Administration Using Breast Cancer-Derived EMT6

$1\times10^5$ breast cancer-derived EMT6 cells (50 uL) were intracutaneously transplanted to the back of each Balb/c mouse (7 weeks old, female). 3 and 10 days after tumor inoculation, 100 μg (100 μL) of a rat anti-mouse CCR8 antibody (clone SA214G2, BioLegend, Inc.) was intraperitoneally administered thereto (N=20). An isotype control antibody was administered to a control (N=20). Tumor volumes were measured every 3 to 4 days from 4 days after tumor inoculation (1 day after antibody administration). The tumor volume ($mm^3$) was calculated according to major axis (mm)×minor axis (mm)×minor axis (mm)/2 (FIG. 31).

As a result, the mean tumor volume of the anti-mouse CCR8 administration group compared with the isotype control antibody administration group was significantly decreased at all the points in time of measurement at post-transplant day 10 or later (significance level: ; P<0.01 at day 10, *; P<0.001 at days 14, 17 and 21). Furthermore, the tumors disappeared in 19 out of 20 mice in the anti-mouse CCR8 antibody administration group and 2 out of 20 mice in the isotype control antibody administration group at post-antibody administration day 21. There was a significant difference (P<0.0001) in the Pearson's chi-square test conducted as to this segregated form.

Example 22

Confirmation of Superiority of Anti-Mouse CCR8 Antibody Over Anti-PD-1 Antibody $2\times10^5$ colorectal cancer-derived Colon26 cells (50 uL) were intracutaneously transplanted to the back of each Balb/c mouse (7 weeks old, female). 3 and 10 days after tumor inoculation, 400 μg (400 μL) of an isotype control antibody, a rat anti-mouse CCR8 antibody (clone SA214G2, BioLegend, Inc.) or an anti-mouse PD-1 antibody (RMP1-14, Bio X Cell) was intravenously administered thereto (N=10). Tumor volumes were measured every 3 to 4 days from 3 days after tumor inoculation. The tumor volume ($mm^3$) was calculated according to major axis (mm)×minor axis (mm)×minor axis (mm)/2 (FIG. 32). As a result, the tumor volume of the anti-mouse CCR8 administration group compared with the isotype antibody administration group was significantly decreased at days 17, 20, and 24 (Steel's nonparametric test: significance level P<0.05). No significant difference was observed in the anti-PD-1 antibody administration group compared with the isotype antibody administration group at any point in time.

A mouse individual bearing a tumor with a volume of 1000 mm3 or larger at post-antibody administration day 24 was 7 out of 10 mice in the isotype antibody administration group, 2 out of 10 mice in the anti-mouse CCR8 antibody administration group, and 7 out of 10 mice in the anti-PD-1 administration group. The anti-CCR8 administration group had a significant difference from both the isotype antibody administration group and the anti-PD-1 antibody administration group in the Pearson's chi-square test as to the segregated form (P=0.025 for both). In conclusion, the anti-mouse CCR8 antibody administration was confirmed to produce an antitumor therapeutic effect on the colorectal cancer cell line Colon26.

Furthermore, the tumor volume of the anti-mouse CCR8 administration group compared with the anti-mouse PD-1 antibody administration group was significantly decreased at 20 and 24 days after tumor inoculation (Steel-Dwass nonparametric test; significance level P<0.05). In conclusion, a stronger antitumor therapeutic effect on the mouse colorectal cell line was observed in the anti-mouse CCR8 antibody administration group compared with the anti-PD-1 antibody administration group.

Example 23

Evaluation of Antitumor Effect of Anti-Mouse CCR8 Antibody Administration Using Kidney Cancer-Derived Cell Line RAG A similar study was conducted using a mouse kidney cancer-derived cell line RAG. $4\times10^5$ kidney cancer-derived RAG cells (50 uL) were intracutaneously transplanted to the back of each Balb/c mouse (8 weeks old, female). 6 days after tumor inoculation, 100 μg (100 μL) of an isotype control antibody (N=10 except for N=9 at day 21), a rat anti-mouse CCR8 antibody (N=10) (clone SA214G2, BioLegend, Inc.) or an anti-mouse PD-1 antibody (N=10) (RMP1-14, Bio X Cell) was intraperitoneally administered thereto. Tumor volumes were measured every 3 to 4 days from 6 days after tumor inoculation. The tumor volume ($mm^3$) was calculated according to major axis (mm)×minor axis (mm)×minor axis (mm)/2 (FIG. 33). As a result, the tumor volume of the anti-mouse CCR8 administration group compared with the isotype antibody administration group was significantly decreased at 14, 17, and 21 days after tumor inoculation (Steel's nonparametric test: significance level P<0.05). No significant difference was observed in the anti-mouse PD-1 antibody administration group compared with the isotype antibody administration group. In conclusion, the anti-mouse CCR8 antibody administration was confirmed to produce an antitumor therapeutic effect on the kidney cancer cell line. Furthermore, the tumor volume of the anti-mouse CCR8 administration group compared with the anti-mouse PD-1 antibody administration group was significantly decreased at post-transplant day 14 (Steel-Dwass nonparametric test; significance level P<0.05). In conclusion, a stronger antitumor therapeutic effect on the mouse kidney cancer cell line was observed in the anti-mouse CCR8 antibody administration group compared with the anti-mouse PD-1 antibody administration group.

Example 24

Analysis on Presence or Absence of Inflammatory Response in Mouse Given Anti-Mouse CCR8

$2\times10^5$ colorectal cancer-derived Colon26 cells (50 uL) were intracutaneously transplanted to the back of each Balb/c mouse (7 weeks old, female). 3 and 10 days after tumor inoculation, 400 μg (400 μL) of a rat anti-mouse CD198 (CCR8) antibody (clone SA214G2, BioLegend, Inc.) or an isotype control antibody (LTF-2, Bio X Cell) was intravenously administered thereto (N=10). The body weight and the weight of each mouse organ (lung, liver, spleen, small intestine, and inguinal node) were measured at post-transplant day 24 (FIG. 34). As a result, as shown in FIG. 34, no significant difference in body weight and each organ weight was observed between the control administration group (N=10) and the anti-mouse CCR8 antibody administration group (N=10). From these results, it was concluded that the anti-mouse CCR8 antibody administration induced neither inflammatory response nor an autoimmune disease.

Example 25

Analysis on Expression of CCR8 in Various Clinical Tumor-Infiltrating Cells

The expression of CCR8 was analyzed in tumor-infiltrating cells of human kidney cancer, ovary cancer, uterine corpus cancer, colorectal cancer, and lung cancer. The numbers of patients with various clinical tumors used in the expression analysis were 12 kidney cancer patients, 14 ovary cancer patients, 21 uterine corpus cancer patients, 10 colorectal cancer patients, and 4 lung cancer patients. Various clinical tumor-infiltrating cells were isolated in the same way as in FIG. 1 of Example 1 and stained with anti-CD45 (BioLegend, Inc., Clone H130) and anti-CCR8 (BioLegend, Inc., Clone L263G8) antibodies, followed by measurement by flow cytometry (BD Biosciences, BD LSRFortessa). A CCR8-positive cell count per tumor weight and the ratio of CCR8-positive cells to CD45-positive leukocytes were analyzed.

Table 2 shows a mean CCR8-positive cell count per tumor weight and a standard deviation thereof. Table 3 shows a mean ratio of CCR8-positive cells to CD45-positive leukocytes and a standard deviation thereof.

TABLE 2

| Cancer type | CCR8-positive cell count ($\times 10^5$) per tumor weight (g) | |
|---|---|---|
| | Mean | Standard deviation |
| Kidney cancer | 8.9 | 22.7 |
| Ovary cancer | 1.7 | 2.6 |
| Uterine corpus cancer | 13.1 | 28.5 |
| Colorectal cancer | 2.9 | 5.4 |
| Lung cancer | 21.8 | 36.9 |

TABLE 3

| Cancer type | Ratio (%) of CCR8-positive cells to CD45-positive leukocytes | |
|---|---|---|
| | Mean | Standard deviation |
| Kidney cancer | 5.6 | 5.2 |
| Ovary cancer | 5.2 | 6.6 |
| Uterine corpus cancer | 9.0 | 9.2 |
| Colorectal cancer | 6.2 | 6.5 |
| Lung cancer | 2.9 | 2.3 |

In the various clinical tumors with kidney cancer as a reference, as for the CCR8-positive cell count per tumor weight, ovary cancer and colorectal cancer exhibited a lower mean than that of kidney cancer, and uterine corpus cancer and lung cancer exhibited a higher mean than that of kidney cancer. As for the ratio of CCR8-positive cells to CD45-positive leukocytes, ovary cancer exhibited a mean equivalent to that of kidney cancer, and lung cancer exhibited a lower mean than that of kidney cancer. Also, uterine corpus cancer and colorectal cancer exhibited a higher mean than that of kidney cancer. The expression of CCR8 was confirmed in the tumor-infiltrating cells of ovary cancer, uterine corpus cancer, colorectal cancer and lung cancer, in addition to the human kidney cancer tumor-infiltrating cells. These results indicated the possibility that in kidney cancer as well as ovary cancer, uterine corpus cancer, colorectal cancer and lung cancer, CCR8-positive tumor-infiltrating cells can be removed using the anti-human CCR8-specific antibody.

Example 26

Evaluation of Antitumor Effect of Combined Administration of Anti-Mouse CCR8 Antibody and Anti-PD-1 Antibody Using Breast Cancer-Derived EMT6

$1 \times 10^5$ breast cancer-derived EMT6 cells (50 uL) were intracutaneously transplanted to the back of each Balb/c mouse (7 weeks old, female).

To an anti-mouse CCR8 antibody alone administration group, 15 µg of a rat anti-mouse CCR8 antibody (clone SA214G2, BioLegend, Inc.) was intravenously administered (100 µL) 3 and 10 days after tumor inoculation, and 200 µg (100 µL) of an isotype control antibody was administered at 8 and 13 days after tumor inoculation (N=10). To an anti-PD-1 antibody alone administration group, 15 µg (100 µL) of an isotype control antibody was intravenously administered 3 and 10 days after tumor inoculation, and 200 µg (100 µL) of an anti-mouse PD-1 antibody (RMP1-14, Bio X Cell) was intravenously administered at 8 and 13 days after tumor inoculation (N=10). To an anti-PD-1 antibody and anti-mouse CCR8 antibody combined administration group, 15 µg (100 µL) of the rat anti-mouse CCR8 antibody was intravenously administered 3 and 10 days after tumor inoculation, and 200 µg (100 µL) of the anti-PD-1 antibody was intravenously administered at 8 and 13 days after tumor inoculation (N=10). To a control group, 15 µg (100 µL) of an isotype control antibody was intravenously administered 3 and 10 days after tumor inoculation, and 100 µL. of PBS was intravenously administered at 8 and 13 days after tumor inoculation (N=10). Tumor volumes were measured every 3 to 4 days from 3 days after tumor inoculation (1 day after antibody administration). The tumor volume (mm$^3$) was calculated according to major axis (mm)×minor axis (mm)× minor axis (mm)/2 (FIG. 35).

In the comparison of a mean tumor volume between the alone administration groups, the mean tumor volume was significantly small in the anti-mouse CCR8 antibody administration group compared with the anti-PD-1 antibody administration group at days 10, 14, 17, 20, 23 and 27 (Dunnett method, significance level: P<0.05). Also, the tumors were small in the combined administration group compared with each alone administration group.

A complete remission rate of the tumors at 17 and 27 days after tumor inoculation was also compared. At post-transplant day 17, the complete remission of the tumors was exhibited in 0 out of 10 mice in the control group and the anti-PD-1 antibody administration group and 1 out of 10 mice in the anti-mouse CCR8 antibody administration group, whereas the tumors remitted completely in 6 out of 10 mice in the anti-PD-1 antibody and anti-mouse CCR8 antibody combined administration group. At post-transplant day 27, the complete remission of the tumors was exhibited in 2 and 3 out of 10 mice in the control group and the anti-PD-1 antibody administration group, respectively, and 7 out of 10 mice in the anti-mouse CCR8 antibody administration group, whereas the tumors remitted completely in 9 out of 10 mice in the anti-PD-1 antibody and anti-mouse CCR8 antibody combined administration group.

The proportion of an individual bearing tumor larger than 50 mm$^3$ or smaller was further calculated (FIG. 36). Tue tumors larger than 50 mm$^3$ or smaller in all the individuals in the anti-PD-1 antibody and anti-mouse CCR8 antibody combined administration group (100%) at post-transplant day 17 and then were 50 mm$^3$ or smaller up to day 27, whereas the proportion was 10% and 30% in the anti-PD-1 antibody administration group at days 17 and 27, respectively, and 70% in the anti-mouse CCR8 antibody administration group at both 17 and 27 days after tumor inoculation.

These results demonstrated that the combined administration group requires a short time to tumor regression and has a strong regressing effect, as compared with other alone administration groups.

Example 27

Evaluation of Antitumor Effect of Combined Administration of Anti-Mouse CCR8 Antibody and Anti-PD-1 Antibody Using Mouse Kidney Cancer-Derived Cell Line RAG $4.5 \times 10^5$ kidney cancer-derived RAG cells (50 uL) were intracutaneously transplanted to the back of each Balb/c mouse (6 weeks old, female). The RAG cells used were RAG cells (acclimatized cell line) with mouse subcutaneous engraftment efficiency elevated by transplanting, again to a mouse, a tumor successfully engrafted in advance by subcutaneous inoculation to a Balb/c mouse and repeating this operation twice.

To an anti-PD-1 antibody alone administration group, 50 μg (100 μL) of an anti-PD-1 antibody (RMP1-14, Bio X Cell) was intravenously administered 8 and 15 days after tumor inoculation (N=10). To an anti-mouse CCR8 antibody alone administration group, 25 μg (100 μL) of a rat anti-mouse CCR8 antibody (clone SA214G2, BioLegend, Inc.) was intravenously administered 8 and 15 days after tumor inoculation (N=10). To an anti-PD-1 antibody and anti-mouse CCR8 antibody combined administration group, 50 μg of an anti-PD-1 antibody (RMP1-14, Bio X Cell) and 25 μg of a rat anti-mouse CCR8 antibody (clone SA214G2, BioLegend, Inc.) were mixed (100 μL) and intravenously administered 8 and 15 days after tumor inoculation (N=10). To a control group, 100 μL of physiological saline was intravenously administered 8 and 15 days after tumor inoculation (N=10).

Tumor volumes were measured every 3 to 4 days from 8 days after tumor inoculation. The tumor volume (mm³) was calculated according to major axis (mm)×minor axis (mm)× minor axis (mm)/2 (FIG. 37).

As a result, the tumors were found to be reduced in size in the anti-PD-1 antibody and anti-mouse CCR8 antibody combined administration group compared with the anti-PD-1 antibody or anti-mouse CCR8 antibody alone administration group.

Example 28

Analysis on Specificity of Anti-Mouse CCR8 Antibody Using Homozygously CCR8 Gene-Deficient Mouse $3 \times 10^5$ colorectal cancer-derived Colon26 cells (50 uL) were intracutaneously transplanted to the back of each wild-type mouse (N=10) or homozygously CCR8 gene-deficient mouse (N=5) of Balb/c lineage. To the wild-type mouse, 100 μg (100 μL) of a rat anti-mouse CCR8 antibody (clone SA214G2, BioLegend, Inc.) or an isotype control antibody (LTF-2, Bio X Cell) was intravenously administered 3 and 10 days after tumor inoculation (N=5). To the homozygously CCR8 gene-deficient mouse, 100 μg (100 μL) of a rat anti-mouse CCR8 antibody (clone SA214G2, BioLegend, Inc.) or an isotype control antibody (LTF-2, Bio X Cell) was also intravenously administered 3 and 10 days after tumor inoculation (N=5). Tumor sizes were measured from post-administration day 7.

As a result, significant tumor regression and final complete tumor regression were observed in all the wild-type mice by the anti-mouse CCR8 antibody administration compared with the isotype control antibody administration. On the other hand, neither change in tumor volume nor tumor regression was observed in the homozygously CCR8 gene-deficient mice in the anti-mouse CCR8 antibody administration group compared with the isotype antibody administration group (FIG. 38).

The antitumor effect of the anti-mouse CCR8 antibody disappeared completely in the homozygously CCR8 gene-deficient mice, demonstrating that the anti-mouse CCR8 antibody (SA214G2) used exerts an antitumor effect via CCR8.

INDUSTRIAL APPLICABILITY

The antibody against CCR8 of the present invention has an effect of activating the immunity by decreasing the number of tumor-infiltrating Treg cells or the like and is thus pharmaceutically useful for the treatment of cancers.

The invention claimed is:

1. A method for treating a solid cancer in a patient having cancer, said method comprising:
   administering to the patient a therapeutically effective amount of an IgG antibody against CCR8 having antibody-dependent cell-mediated cytotoxicity (ADCC) activity against cells expressing CCR8,
   wherein the antibody against CCR8 binds to CCR8 on tumor infiltrating Treg cells or tumor infiltrating macrophage cells, and removes these cells by the ADCC activity of this antibody,
   in the administering step, the only antibody administered is the IgG antibody against CCR8,
   the IgG antibody against CCR8 is a CCR8-neutralizing antibody, and
   the solid cancer excludes CCR8+cancer cells.

2. The method according to claim 1, comprising further administration of an anti-PD-1 antibody or an anti-PD-L1 antibody.

3. The method according to claim 1, wherein an Fc region of the antibody is free from a fucose bound with N-acetylglucosamine.

4. The method according to claim 1, wherein the antibody is administered as a composition further comprising a carrier.

5. The method according to claim 4, wherein the composition is administered intravenously.

6. The method according to claim 4, wherein the composition is administered intraperitoneally.

7. The method according to claim 1, wherein the solid cancer is a cancer selected from the group consisting of breast cancer, uterine corpus cancer, ovary cancer, lung cancer, colorectal cancer, kidney cancer and sarcoma.

* * * * *